United States Patent
Abbitt et al.

(10) Patent No.: US 9,725,729 B2
(45) Date of Patent: Aug. 8, 2017

(54) SB-ACTIN TERMINATOR SEQUENCE FOR GENE EXPRESSION IN PLANTS

(71) Applicant: PIONEER HI-BRED INTERNATIONAL, INC., Des Moines, IA (US)

(72) Inventors: Shane E. Abbitt, Ankeny, IA (US); Rudolf Jung, Lohr am Main (DE)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 193 days.

(21) Appl. No.: 14/438,054

(22) PCT Filed: Jun. 3, 2013

(86) PCT No.: PCT/US2013/043818
§ 371 (c)(1),
(2) Date: Apr. 23, 2015

(87) PCT Pub. No.: WO2013/184537
PCT Pub. Date: Dec. 12, 2013

(65) Prior Publication Data
US 2015/0291968 A1    Oct. 15, 2015

Related U.S. Application Data

(60) Provisional application No. 61/655,087, filed on Jun. 4, 2012.

(51) Int. Cl.
| | | |
|---|---|---|
| *A01H 5/00* | (2006.01) | |
| *A01H 1/00* | (2006.01) | |
| *C12N 15/82* | (2006.01) | |
| *C07H 21/04* | (2006.01) | |
| *C12N 15/00* | (2006.01) | |

(52) U.S. Cl.
CPC .............................. *C12N 15/8216* (2013.01)

(58) Field of Classification Search
None
See application file for complete search history.

(56) References Cited

U.S. PATENT DOCUMENTS

2004/0172684 A1\* 9/2004 Kovalic ................ C07H 21/04
                                                              800/284
2009/0089897 A1    4/2009 Abbitt et al.

FOREIGN PATENT DOCUMENTS

WO    2006/013072 A2    2/2006

OTHER PUBLICATIONS

Shahjahan Ali et al., Quantitative regulation of the Flaveria Me1 gene is controlled by the 3'-untranslated region and sequences near the amino terminus, Plant Molecular Biology, 2001, pp. 251-261, vol. 46.
Gynheung An et al., Functional Analysis of the 3' Control Region of the Potato Wound-Inducible Proteinase Inhibitor II Gene, The Plant Cell, Jan. 1989, pp. 115-122, vol. 1.
Stephane Bieri et al., Geminivirus sequences as bidirectional transcription termination/polyadenylation signals for economic construction of stably expressed transgenes, Molecular Breeding, 2002, pp. 107-117, vol. 10.
Ivan L.W. Ingelbrecht et al., Different 3' End Regions Strongly Influence the Level of Gene Expression in Plant Cells, The Plant Cell, Jul. 1989, pp. 671-680, vol. 1.
A. H. Paterson et al., Sorghum bicolor hypothetical protein, mRNA, National Center for Biotechnology Information No. 242090680, Database Accession No. 002441128, Jul. 13, 2009.
Anonymous: A report by a deliberative committee modifying the approval application of the first-class use official regulations, such as genetically-modified creature—e-Gov Japan—Feb. 15, 2013, XP002709689—Reference in Japanese.
Anonymous: Corn harmful to insect resistance of butterfly eyes and in weed killer glufosinate tolerance, DuPont, Feb. 14, 2013, XP002709690—Reference not available.
International Search Report—PCT/US2013/043818—mailed Sep. 10, 2013.

\* cited by examiner

*Primary Examiner* — Phuong Bui

(57) ABSTRACT

The present invention discloses polynucleotide sequences that can be used to regulate gene expression in plants. Terminator sequences from *Sorghum bicolor* that are functional in plants are disclosed. Nucleic acid molecules, recombinant expression constructs, plants and seed comprising these terminator sequences are further disclosed.

10 Claims, 7 Drawing Sheets

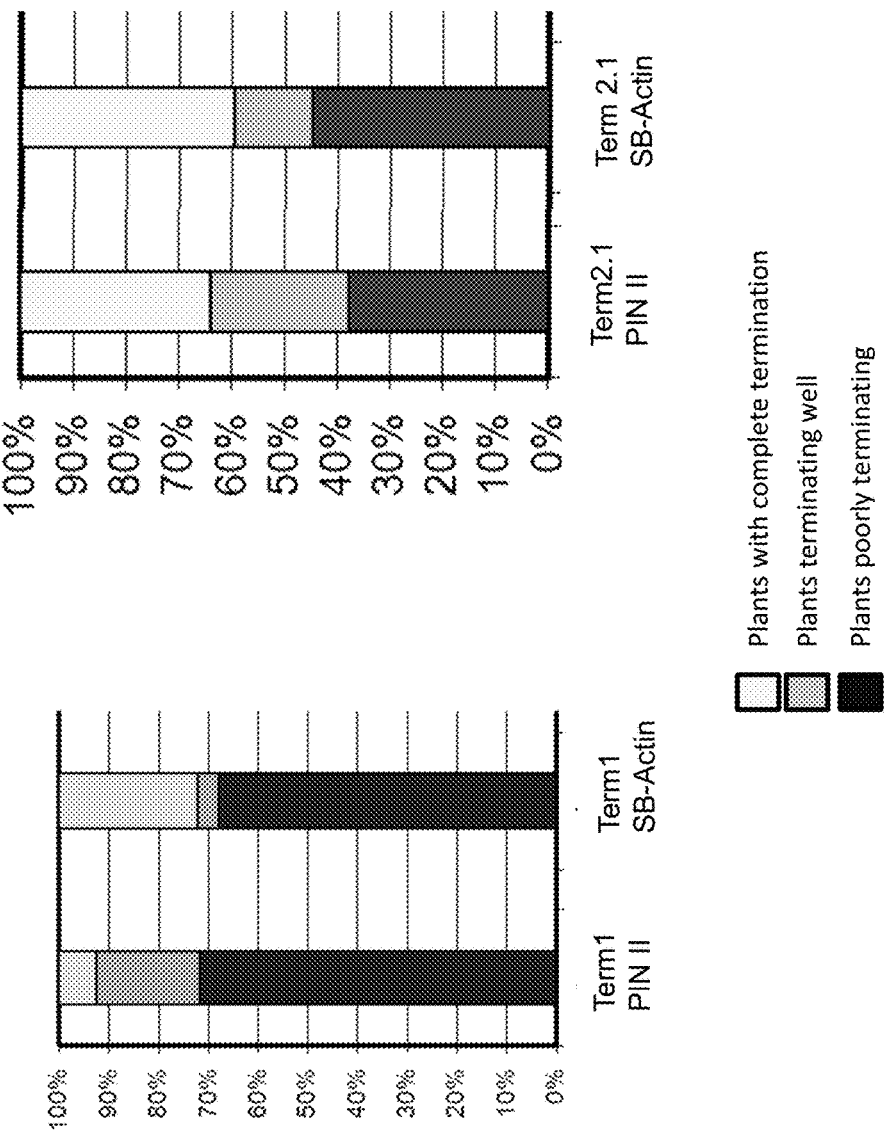

FIG 6A

| | | | | | | |
|---|---|---|---|---|---|---|
| Majority | GTTTTTCTCAGACAGTTTTCTAAAAAAGGGCGTTTCTGGGGAAGTTCGAGATGGTTCGT | | | | | |
| | | 10 | 20 | 30 | 40 | 50 | 60 |
| SEQ ID NO-1.seq | GTTTTTCTCAGACAGTTTTCTAAAAAAGGGCGTTTCTGGGGAAGTTCGAGATGGTTCGT | 60 |
| SEQIDNO-19.seq | GTTTTTCTCAGACAGTTTTCTAAAAAAGGGCGTTTCTGGGGAAGTTCGAGATGGTTCGT | 60 |

| | |
|---|---|
| Majority | AAGGTGTTACTGGCTCCTGTGAACCAATACATGATACTGCCATGATAAGGGTTATAATTA |
| | 70    80    90    100    110    120 |
| SEQ ID NO-1.seq | AAGGTGTTACTGGCTCCTGTGAACCAATACATGATACTGCCATGATAAGGGTTATAATTA  120 |
| SEQIDNO-19.seq  | AAGGTGTTACTGGCTCCTGTGAACCAATACATGATACTGCCATGATAAGGGTTATAATTA  120 |

| | |
|---|---|
| Majority | GTCAAGCAGAGTAAGAAGAAAXAACAGTAGCAGTGACTCCGATTCCTGAAGATGAGTCAT |
| | 130    140    150    160    170    180 |
| SEQ ID NO-1.seq | GTCAAGCAGAGTAAGAAGAAACAACAGTAGCAGTGACTCCGATTCCTGAAGATGAGTCAT  180 |
| SEQIDNO-19.seq  | GTCAAGCAGAGTAAGAAGAAATAACAGTAGCAGTGACTCCGATTCCTGAAGATGAGTCAT  180 |

| | |
|---|---|
| Majority | ATTTGTCTTGTGCTCCTGCTGTATGAAATGGATCGCATGTGTATATTCGTCGCCGGCCG |
| | 190    200    210    220    230    240 |
| SEQ ID NO-1.seq | ATTTGTCTTGTGCTCCTGCTGTATGAAATGGATCGCATGTGTATATTCGTCGCCGGCCG  240 |
| SEQIDNO-19.seq  | ATTTGTCTTGTGCTCCTGCTGTATGAAATGGATCGCATGTGTATATTCGTCGCCGGCCG  240 |

FIG. 6B

| | | |
|---|---|---|
| Majority | CACTGGTGTAACCTGTTGCCTCAGAGTTTGCTTTTAGCTGGTTCTGTTTTAAAAATAAGT | |
| | 250　260　270　280　290　300 | |
| SEQ ID NO-1.seq | CACTGGTGTAACCTGTTGCCTCAGAGTTTGCTTTTAGCTGGTTCTGTTTTAAAAATAAGT | 300 |
| SEQIDNO-19.seq | CACTGGTGTAACCTGTTGCCTCAGAGTTTGCTTTTAGCTGGTTCTGTTTTAAAAATAAGT | 300 |
| Majority | ACTGTTTTTTGGTTGGCTGCAAGCCATTCTGAACTTCAGTTTACCAATTGTTTTTATGTT | |
| | 310　320　330　340　350　360 | |
| SEQ ID NO-1.seq | ACTGTTTTTTGGTTGGCTGCAAGCCATTCTGAACTTCAGTTTACCAATTGTTTTATGTT | 360 |
| SEQIDNO-19.seq | ACTGTTTTTTGGTTGGCTGCAAGCCATTCTGAACTTCAGTTTACCAATTGTTTTTATGTT | 360 |
| Majority | GTGGTTGAATATTTTAATTTTTATTTAATGTTTGGTTCTTTTTXXXXXXXXXXXXXXXXX | |
| | 370　380　390　400　410　420 | |
| SEQ ID NO-1.seq | GTGGTTGAATATTTTAATTTTTATTTAATGTTTGGTTCTTTTTATATATATTTGCAA | 420 |
| SEQIDNO-19.seq | GTGGTTGAATATTTTAATTTTTATTTAATGTTTGGTTCTTTTTT | 406 |

SB-ACTIN TERMINATOR SEQUENCE FOR GENE EXPRESSION IN PLANTS

This application claims the benefit of U.S. Provisional Application No. 61/655,087, filed Jun. 4, 2012; the entire content of which is herein incorporated by reference.

FIELD OF INVENTION

The present invention relates to the field of plant molecular biology and plant genetic engineering. More specifically, it relates to novel plant terminator sequences and their use to regulate gene expression in plants.

BACKGROUND

Recent advances in plant genetic engineering have opened new doors to engineer plants to have improved characteristics or traits. These transgenic plants characteristically have recombinant DNA constructs in their genome that have protein coding region operably linked to multiple regulatory regions that allow accurate expression of the transgene. A few examples of regulatory elements that help regulate gene expression in transgenic plants are promoters, introns, terminators, enhancers and silencers.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes. But it is important to modulate or control the expression of each transgene optimally. The regulatory elements need to be diverse, to avoid introducing into the same transgenic plant repetitive sequences, which has been correlated with undesirable negative effects on transgene expression and stability (Peremarti et al (2010) *Plant Mol Biol* 73:363-378; Mette et al (1999) EMBO J 18:241-248; Mette et al (2000) EMBO J 19:5194-5201; Mourrain et al (2007) Planta 225:365-379, U.S. Pat. No. 7,632,982, U.S. Pat. No. 7,491,813, U.S. Pat. No. 7,674,950, PCT Application No. PCT/US2009/046968). Therefore it is important to discover and characterize novel regulatory elements that can be used to express heterologous nucleic acids in important crop species. Diverse regulatory regions can be used to control the expression of each transgene optimally.

Regulatory sequences located downstream of coding regions contain signals required for transcription termination and 3' mRNA processing, and are called terminator sequences. The terminator sequences play a key role in mRNA processing, localization, stability and translation (Proudfoot, N. (2004) *Curr. Op. Cell Biol* 16:272-278; Gilmartin, 2005). The 3' regulatory sequences contained in terminator sequences can affect the level of expression of a gene. Optimal expression of a chimeric gene in plant cells has been found to be dependent on the presence of appropriate 3' sequences (Ingelbrecht, I. L. W. et al (1989) *Plant Cell* 1:671-680). Read through transcription through leaky terminator of a gene can cause unwanted transcription of one transgene from promoter of another one. Also, bidirectional, convergent transcription of transgenes in transgenic plants can occur due to leaky transcription termination of separate convergent genes or from genomic promoters. Convergent, overlapping transcription can decrease transgene expression, or generate antisense RNA (Bieri, S. et al (2002) *Molecular Breeding* 10:107-117). This underlines the importance of discovering novel and efficient transcriptional terminators.

SUMMARY

The present invention relates to regulatory sequences for modulating gene expression in plants. Specifically, the present invention relates to terminator sequences. Recombinant DNA constructs comprising terminator sequences are provided.

An embodiment of this invention is an isolated polynucleotide sequence comprising: (a) the sequence set forth in SEQ ID NO:2, SEQ ID NO:1 or SEQ ID NO: 19; (b) a sequence with at least 95% sequence identity to SEQ ID NO:2, SEQ ID NO:1 or SEQ ID NO: 19; or (c) a sequence comprising a functional fragment of (a) or (b), wherein the isolated polynucleotide sequence functions as a terminator in a plant cell. Another embodiment of this invention is a recombinant construct comprising an isolated polynucleotide sequence comprising: (a) the sequence set forth in SEQ ID NO:2, SEQ ID NO:1 or SEQ ID NO: 19; (b) a sequence with at least 95% sequence identity to SEQ ID NO:2, SEQ ID NO:1 or SEQ ID NO: 19; or (c) a sequence comprising a functional fragment of (a) or (b), wherein the isolated polynucleotide sequence functions as a terminator in a plant cell. This recombinant construct may further comprise a promoter and a heterologous polynucleotide, wherein the promoter and the heterologous polynucleotide are operably linked to the isolated polynucleotide sequence.

Another embodiment of this invention is a method of expressing a heterologous polynucleotide in a plant, comprising the steps of (a) introducing into a regenerable plant cell the recombinant DNA construct described above; (b) regenerating a transgenic plant from the regenerable plant cell of (a); and (c) obtaining a progeny plant from the transgenic plant of step (b), wherein the transgenic plant and the progeny plant comprises the recombinant DNA construct and exhibits expression of the heterologous polynucleotide.

In a fourth embodiment, this invention concerns a vector, cell, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described in the present invention is a monocotyledenous plant. In another embodiment, the plant comprising the terminator sequences described in the present invention is a maize plant.

BRIEF DESCRIPTION OF DRAWINGS AND SEQUENCE LISTING

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1A) shows the map of PHP32622, the vector used for cloning the SB-ACTIN (1.0 kb) and B) the map of PHP32497, the vector used for cloning the SB-ACTIN (0.6 kb) terminator.

FIG. 4A shows GUS reporter gene expression assayed at protein level, and FIG. 4B shows GUS reporter gene expression assayed with qRT-PCR.

Figure 1:
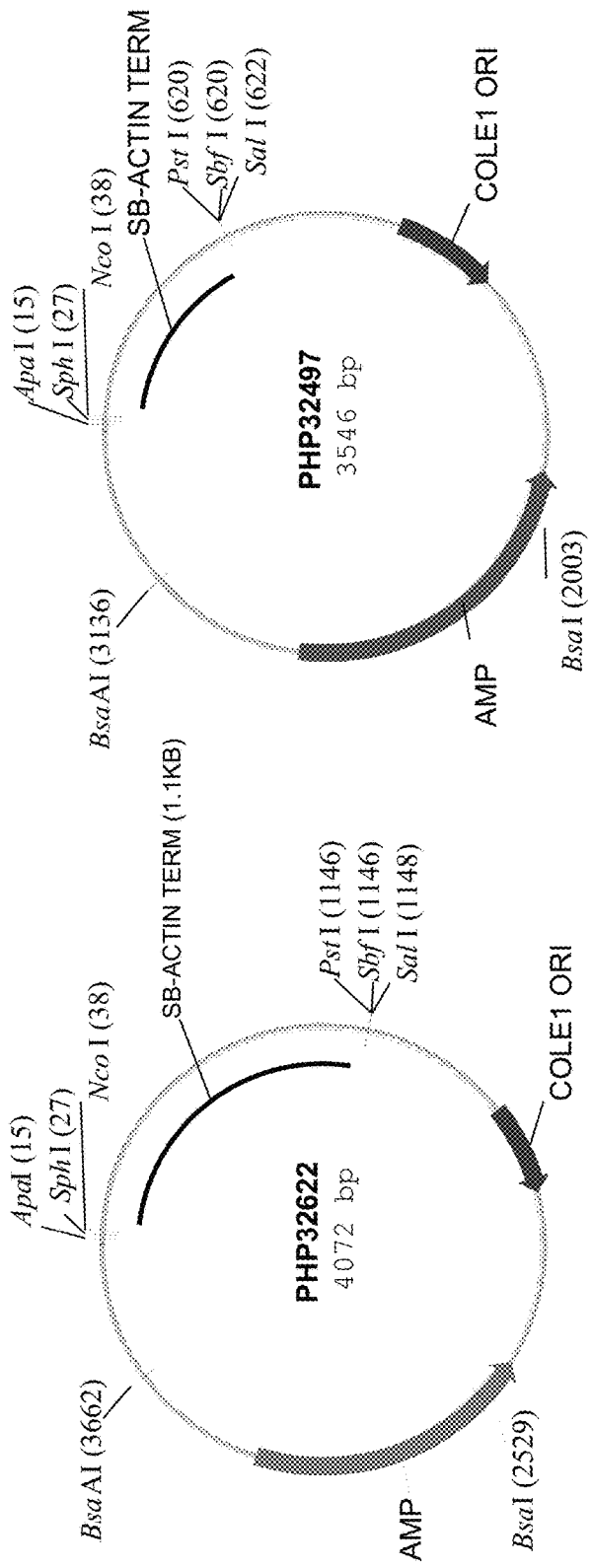

FIGS. 5A and 5B show the results of qRT-PCR assays with stably transformed Gaspe Flint derived maize lines, using two sets of primers (set 1 in 5A and set 2 in 5B) downstream of the 1.0 kb SB-ACTIN terminator and the PINII terminator.

FIGS. 6A-6B shows the alignment between the cloned SB-ACTIN terminator (nucleotides 1-420 of SEQ ID NO: 1) and the nucleotides 1430 to 1835 of NCBI GI NO: 242090680 (SEQ ID NO: 19).

SEQ ID NO: 1 is the nucleotide sequence of the 1043 bp SB-ACTIN terminator.

SEQ ID NO: 2 is the nucleotide sequence of the 517 bp SB-ACTIN terminator.

SEQ ID NO: 3 is the nucleotide sequences of the forward primer TMS2120 used to amplify SB-ACTIN terminator.

SEQ ID NO: 4 is the nucleotide sequences of the reverse primer TMS2132 used to amplify SB-ACTIN terminator.

SEQ ID NO: 5 is the nucleotide sequence of PHP32622, the vector used for cloning the 1.0 kb SB-ACTIN terminator after PCR amplification.

SEQ ID NO: 6 is the nucleotide sequence of PHP34007, the vector used for testing the 1.0 kb SB-ACTIN terminator.

SEQ ID NO: 7 is the nucleotide sequence of PHP34005, the test vector used as a control with PINII terminator.

SEQ ID NOS: 8, 9, 10 are the sequences of the forward primer, reverse primer and probe used for assessing GUS expression by qRT-PCR in transgenic maize plants, as described in Table 2.

SEQ ID NOS: 11-18 are the sequences of the primers used for quantitating read through transcription through SB-ACTIN and PINII terminators, by qRT-PCR in transgenic maize plants, as described in Table 3.

SEQ ID NO: 19 corresponds to nucleotides 1430 to 1835 of NCBI GI NO: 242090680

SEQ ID NO: 20) is the nucleotide sequence from NCBI GI NO: 242090680.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not found together in nature. Accordingly, a recombinant DNA construct may comprise regulatory sequences and coding sequences that are derived from different sources, or regulatory sequences and coding sequences derived from the same source, but arranged in a manner different than that found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"Transcription terminator", "termination sequences", or "terminator" refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence. Transcription termination is the process by which RNA synthesis by RNA polymerase is stopped and both the RNA and the enzyme are released from the DNA template. Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117).

As used herein, "SB-ACTIN terminator" or "SB-actin" refers to a nucleotide sequence from the *Sorghum bicolor* actin gene that functions as a terminator. The SB-ACTIN terminator can be the full length 1043 bp (1.0 kb) SB-ACTIN terminator, which comprises a sequence encoding the 3' untranslated region (3' UTR) (about 392 bp) of the *Sorghum Bicolor* actin gene and about 651 bp of sequence downstream from the 3' UTR. The sequence of the 1.0 kb SB-ACTIN terminator is given in SEQ ID NO: 1. The SB-ACTIN terminator can also be any functional fragment of SEQ ID NO:1, including but not limited to SEQ ID NO:2, SEQ ID NO:19, or a derivative of SEQ ID NO:1 obtained by deletion, substitution or addition of one or more nucleotides, wherein the fragment contains terminator activity.

The *Sorghum bicolor* actin gene encodes a microfilament, and the sequence for this gene is given in NCBI GI NO: 242090680 (SEQ ID NO: 20). The *sorghum* actin is one of three major components of the cytoskeleton which are used throughout the plant. Actin plays an important role in cell division and cytokinesis.

The present invention encompasses functional fragments and variants of the terminator sequences disclosed herein.

A "functional fragment" of the terminator is defined as any subset of contiguous nucleotides of the terminator sequence disclosed herein, that can perform the same, or substantially similar function as the full length terminator sequence disclosed herein. A "functional fragment" with substantially similar function to the full length terminator disclosed herein refers to a functional fragment that retains the ability to terminate transcription largely at the same level as the full-length terminator sequence. A recombinant construct comprising a heterologous polynucleotide operably linked to a "functional fragment" of the terminator sequence disclosed herein exhibits levels of heterologous polynucleotide expression substantially similar to a corresponding recombinant construct comprising a heterologous polynucleotide operably linked to the full length terminator sequence.

A "variant", as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments will comprise at least about 20 contiguous nucleotides, preferably at least about 50 contiguous nucleotides, more preferably at least about 75 contiguous nucleotides, even more preferably at least about 100 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms "substantially similar" and "corresponding substantially" as used herein refer to nucleic acid fragments, particularly terminator sequences, wherein changes in one or more nucleotide bases do not substantially alter the ability of the terminator to terminate transcription. These terms also refer to modifications, including deletions and variants, of the nucleic acid sequences of the instant invention by way of deletion or insertion of one or more nucleotides that do not substantially alter the functional properties of the resulting terminator relative to the initial, unmodified terminator. It is therefore understood, as those skilled in the art will appreciate, that the invention encompasses more than the specific exemplary sequences.

As will be evident to one of skill in the art, any heterologous polynucleotide of interest can be operably linked to the terminator sequences described in the current invention. Examples of polynucleotides of interest that can be operably linked to the terminator sequences described in this invention include, but are not limited to, polynucleotides comprising regulatory elements such as introns, enhancers, promoters, translation leader sequences, protein coding regions such as disease and insect resistance genes, genes conferring nutritional value, genes conferring yield and heterosis increase, genes that confer male and/or female sterility, antifungal, antibacterial or antiviral genes, and the like. Likewise, the terminator sequences described in the current invention can be used to terminate transcription of any nucleic acid that controls gene expression. Examples of nucleic acids that could be used to control gene expression include, but are not limited to, antisense oligonucleotides, suppression DNA constructs, or nucleic acids encoding transcription factors.

Regulatory Sequences:

A recombinant DNA construct (including a suppression DNA construct) of the present invention may comprise at least one regulatory sequence. In an embodiment of the present invention, the regulatory sequences disclosed herein can be operably linked to any other regulatory sequence.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

The terms "real-time PCR", "quantitative PCR", "quantitative real-time PCR" and "QPCR" are used interchangeably herein, and represent a variation of the standard polymerase chain reaction (PCR) technique used to quantify DNA or RNA in a sample. Using sequence-specific primers and a probe, the relative number or copies of a particular DNA or RNA sequence are determined. The term relative is used since this technique compares relative copy numbers between different genes with respect to a specific reference gene. The quantification arises by measuring the amount of amplified product at each cycle during the PCR process. Quantification of amplified product is obtained using fluorescent hydrolysis probes that measure increasing fluorescence for each subsequent PCR cycle. The Ct (cycle threshold) is defined as the number of cycles required for the fluorescent signal to cross the threshold (i.e., exceeds background level). DNA/RNA from genes with higher copy numbers will appear after fewer PCR cycles; so the lower a Ct value, the more copies are present in the specific sample. To quantify RNA, QPCR or real-time PCR is preceded by the step of reverse transcribing mRNA into cDNA. This is referred to herein as "real-time RT-PCR" or "quantitative RT-PCR" or "qRT-PCR".

The Taqman method of PCR product quantification uses a fluorescent reporter probe. This is more accurate since the probe is designed to be sequence-specific and will only bind to the specific PCR product. The probe specificity allows for quantification even in the presence of non-specific DNA amplification. This allows for multiplexing, which quantitates several genes in the same tube, by using probes with different emission spectra. Breakdown of the probe by the 5' to 3' exonuclease activity of Taq polymerase removes the quencher and allows the PCR product to be detected.

When plotted on a linear scale, the fluorescent emission increase with PCR cycle number has a sigmoidal shape with an exponential phase and a plateau phase. The plateau phase is determined by the amount of primer in the master mix rather than the nucleotide template. Usually the vertical scale is plotted in a logarithmic fashion, allowing the intersection of the plot with the threshold to be linear and more easily visualized. Theoretically, the amount of DNA doubles every cycle during the exponential phase, but this is affected by the efficiency of the primers used. A positive control using a reference gene, e.g., a "housekeeping" gene that is relatively abundant in all cell types, is also performed to allow for comparisons between samples. The amount of DNA/RNA is determined by comparing the results to a standard curve produced by serial dilutions of a known concentration of DNA/RNA.

The present invention includes a polynucleotide comprising: (i) a nucleic acid sequence of at least 90%, 91%, 92%, 93%, 94%, 95%, 96%, 97%, 98%, 99%, or 100% sequence identity, based on the Clustal V method of alignment, when compared to SEQ ID NO:2, SEQ ID NO:1 or SEQ ID NO: 19; or (ii) a nucleic acid sequence of at least 90%, 91%, 92%, 93%, 94%, 95%, 96%, 97%, 98%, 99% or 100% sequence identity, based on the Clustal V method of alignment, when compared to a functional fragment of SEQ ID NO:2, SEQ ID NO:1 or SEQ ID NO: 19; or (iii) a full complement of the nucleic acid sequence of (i) or (ii), wherein the polynucleotide acts as a terminator in a plant cell.

Embodiments of the invention include:

The present invention relates to terminator sequences. Recombinant DNA constructs comprising terminator sequences are provided.

An embodiment of this invention is an isolated polynucleotide sequence comprising (a) the sequence set forth in SEQ ID NO:2, SEQ ID NO:1 or SEQ ID NO: 19; (b) a sequence with at least 95% sequence identity to SEQ ID NO:2, SEQ ID NO:1 or SEQ ID NO: 19; or (c) a sequence comprising a functional fragment of (a) or (b), wherein the isolated polynucleotide sequence functions as a terminator in a plant cell. In another aspect, this invention concerns a recombinant DNA construct comprising a promoter, at least one heterologous nucleic acid fragment, and any terminator, or combination of terminator elements, of the present invention, wherein the promoter, at least one heterologous nucleic acid fragment, and terminator(s) are operably linked.

Recombinant DNA constructs can be constructed by operably linking the nucleic acid fragment of the invention, the terminator sequences set forth SEQ ID NO:2, SEQ ID NO:1 or SEQ ID NO: 19 or a functional fragment of the nucleotide sequence set forth in SEQ ID NO:2, SEQ ID NO:1 or SEQ ID NO: 19 to a heterologous nucleic acid fragment.

Another embodiment of this invention is a method of expressing a heterologous polynucleotide in a plant, comprising the steps of introducing into a regenerable plant cell the recombinant DNA construct described above and regenerating a transgenic plant from the transformed regenerable plant cell, wherein the transgenic plant comprises the recombinant DNA construct and exhibits expression of the heterologous polynucleotide.

Another embodiment of this invention is a method of expressing a heterologous polynucleotide in a plant, comprising the steps of introducing into a regenerable plant cell the recombinant DNA construct described above; regenerating a transgenic plant from the regenerable plant cell described above; and obtaining a progeny plant from the transgenic plant, wherein the transgenic plant and the progeny plant comprises the recombinant DNA construct and exhibits expression of the heterologous polynucleotide.

In another embodiment, this invention concerns a vector, cell, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described in the present invention is a monocotyledenous plant. In another embodiment, the plant comprising the terminator sequences described in the present invention is a maize plant.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Amplification and Cloning of a *Sorghum bicolor* Actin Terminator Sequence

Primers (SEQ ID NOS: 3 and 4) were designed for amplifying the terminator of actin gene from *Sorghum bicolor* (SB-ACTIN) based on the *Sorghum bicolor* genomic sequence database. The primer sequences are given below, the underlined region is not homologous with genomic template:

```
TMS2120 (forward primer; SEQ ID NO: 3):
ACTAGTGTTTTCTCAGACAGTTTTCTAAAAAAAGGGCG TMS2132 (reverse primer; SEQ ID NO: 4):
GAATTCCCATAAGTGCTTGATTAGGTCTTC
```

Figure 2:
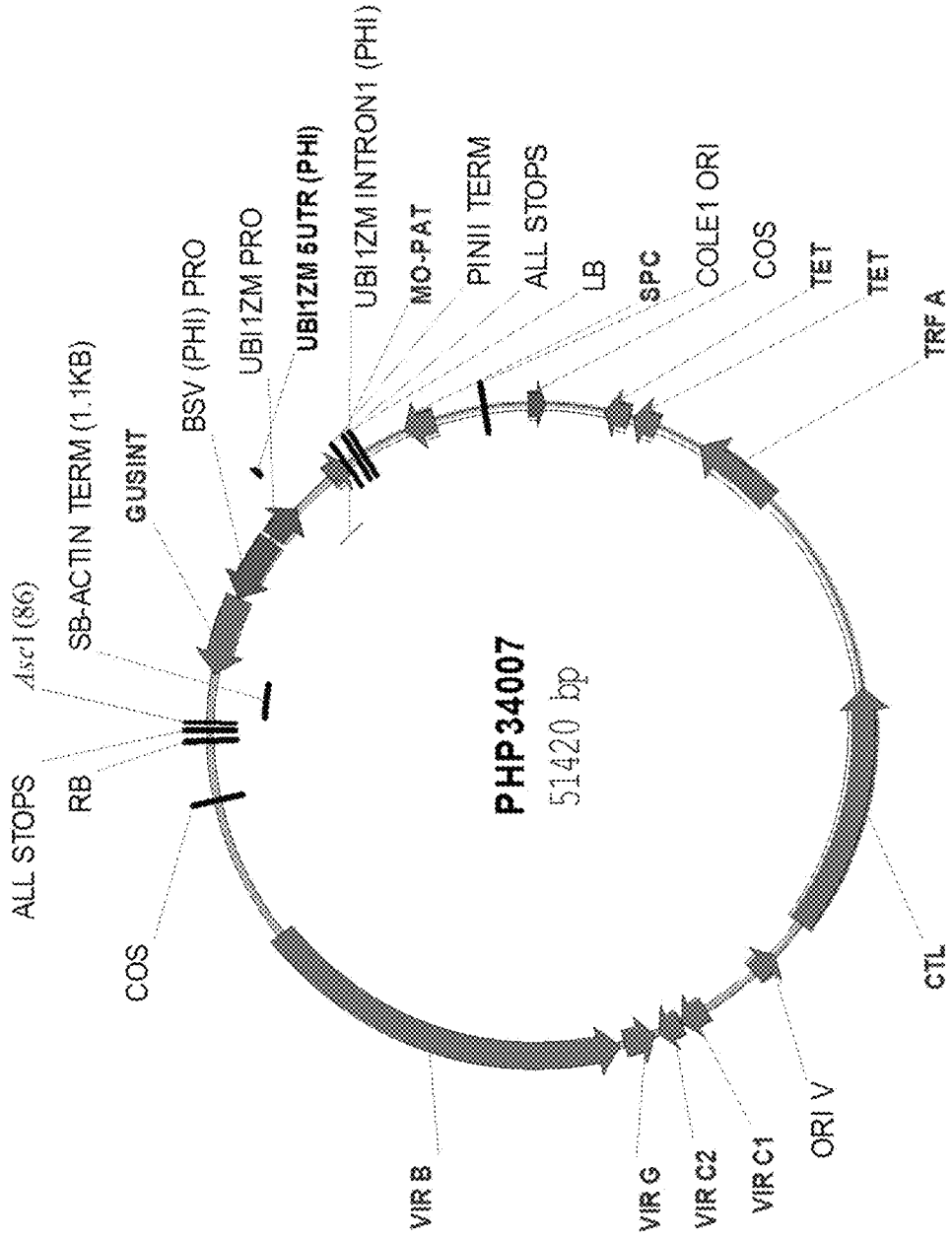
FIG. 2 shows the map of PHP34007, the vector used for testing the 1.0 kb SB-ACTIN terminator.

A 1043-bp product comprising the 1.0 kb SB-ACTIN terminator sequence (SEQ ID NO: 1) was amplified by PCR using these primers. The product was cloned into pGEMTeasy (Promega) (PHP32622; FIG. 1; SEQ ID NO: 5) and the sequence was confirmed. The cloned SB-ACTIN terminator included about 392 bp of the predicted 3' UTR of SB-ACTIN along with about 651 bp of downstream sequence. The amplified sequence of the 1.0 kb SB-ACTIN terminator (SEQ ID NO: 1) was then cloned into an *Agrobacterium* transformation vector (PHP34007; FIG. 2; SEQ ID NO: 6), which had the following expression cassettes in divergent orientation:

SB-ACTIN TERMINATOR: GUSINT: BSV PRO and

UBI-PRO:UBI INTRON:MOPAT:PINII TERM.

BSV PRO is Banana Streak Virus promoter, which is a strong constitutive promoter. A construct with a potato PINII terminator (Keil et al. 1986 Nucleic Acids Res. 14:5641-5650) in place of the SB-ACTIN terminator was used as a control (PHP34005; SEQ ID NO: 7).

A 517 bp fragment of the SB-ACTIN terminator, referred to as the 0.6 kb SB-ACTIN terminator (SEQ ID NO:2) was also obtained by Genomic PCR.

Example 2

Transient Transformation to Test Efficacy of a SB-ACTIN Terminator

Figure 3:
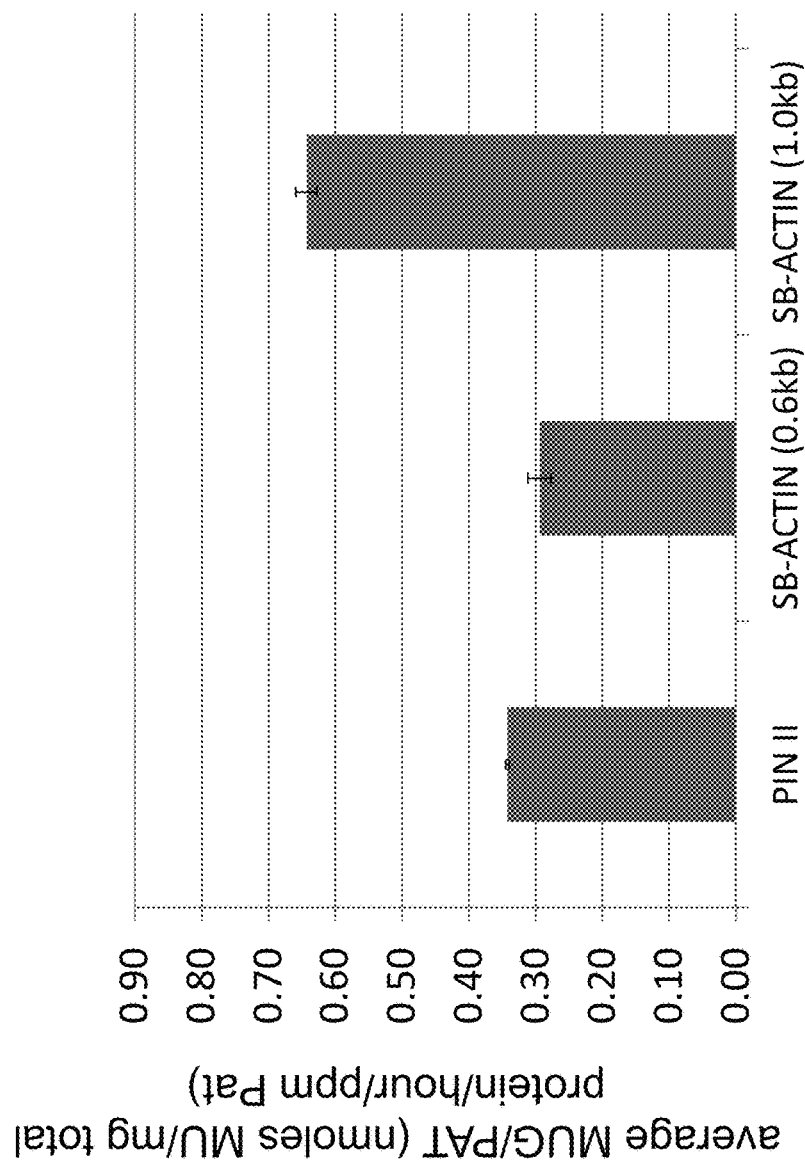
FIG. 3 shows the results of testing the 0.6 kb and 1.0 kb SB-ACTIN terminator compared to PINII terminator in transient assays. It shows quantitative analysis of GUS reporter gene expression in BMS cells transformed with PHP34007 (1.0 kb SB-ACTIN terminator) and PHP34005 (PINII terminator).

The isolated SB-ACTIN terminator sequences (SEQ ID NO: 1 and SEQ ID NO:2) were tested for their ability to act efficiently as a terminator in a recombinant construct. Its efficacy as a terminator was tested by its ability to stop transcription and by its ability to increase expression of a protein. Since improper termination can lead to improper processing of the 3' end of mRNA, and hence affect RNA stability, terminators have been found to affect protein expression levels. It has been shown that different terminators can cause up to 100 fold variation in the efficiency of transgene expression (Bieri et al, (2002) *Molecular Breeding* 10: 107-117; An et al (1989) *Plant Cell* 1: 115-122; Ingelbrecht et al (1989), *Plant Cell,* 1:671-680; Ali and Taylor (2001) *Plant Mol. Bio.,* 46:251-261). SB-ACTIN sequences (SEQ ID NO: 1 and SEQ ID NO:2) were tested for their ability to increase expression of a protein compared to the well-known PINII terminator. The *Agrobacterium* transformation vectors PHP34007 (SEQ ID NO: 6) and PHP34005 (SEQ ID NO: 7) described in example 1 were used for transient transformation of BMS (Black Mexican Sweet) cells. The cells were harvested 5 days after transformation and sent for a quantification of the GUS activity (MUG assay). The SB-ACTIN (1.0 kb) terminator (PHP34007; SEQ ID NO: 6) had ~88% more expression than that of the PINII construct (PHP34005, SEQ ID NO: 7) when the GUS expression was normalized to the MOPAT expression (FIG. 3; Table 1), whereas the SB-ACTIN (0.6 kb) construct had similar expression than that of the of the PINII construct. This information was indicative of the ability of the isolated SB-ACTIN sequences (SEQ ID NO: 1 and SEQ ID NO:2) to act efficiently as terminators, by allowing protein expression equal to or above that of the PINII terminator.

TABLE 1

| Construct | Sequence Tested | Average MUG/PAT* | Standard Deviation |
| --- | --- | --- | --- |
| BSV PRO:GUSINT:PINII TERM | PIN II TERM | 0.34 | 0.00 |
| BSV PRO:GUSINT:SB-ACTIN TERM | SB-ACTIN (1.0 kb) TERM | 0.64 | 0.02 |
| BSV PRO:GUSINT:SB-ACTIN TERM | SB-ACTIN (0.6 kb) TERM | 0.29 | 0.02 |

*Measured as: nmoles MU/mg total protein/hour/ppm PAT

Example 3

Stable Transformation Assays to Test SB-ACTIN Terminator Activity

The *Agrobacterium* transformation vectors PHP34007 (SEQ ID NO: 6) and PHP 34005 (SEQ ID NO: 7) described in Example 1, that were used for transient transformation assays as described in Example 2, were also used in Gaspe-Flint derived maize lines for stable transformation to generate transgenic maize plants.

Quantitative Reverse Transcriptase-PCR (qRT-PCR) and GUS assays were done from stably transformed plant tissues to test the ability of isolated 1.0 kb SB-ACTIN terminator sequence (SEQ ID NO:1) to stop transcription (that is prevent transcription read-through transcription) and to compare GUS expression as compared to that with PINII terminator.

GUS Expression Analysis:

The expression of the GUS gene in the transgenic plants was assessed at the protein as well as transcript levels. To assess the expression at the protein level, MUG assay was performed on seedling leaf material. To assess the expression at the transcript level, qRT-PCR was done using primers shown in Table 2.

TABLE 2

| Primer/Probe | Type | Sequence | Fluor | qPCR Assay |
| --- | --- | --- | --- | --- |
| GUS-1482F | Forward | CGGAAGCAACGCGTAAACTC (SEQ ID NO: 8) | - | Taqman |
| GUS-1553R | Reverse | TGTGAGCGTCGCAGAACATTA (SEQ ID NO: 9) | - | Taqman |
| GUS-1509P | Probe | CGCGTCCGATCACCTGCGTC (SEQ ID NO: 10) | FAM | Taqman |

Figure 4B:
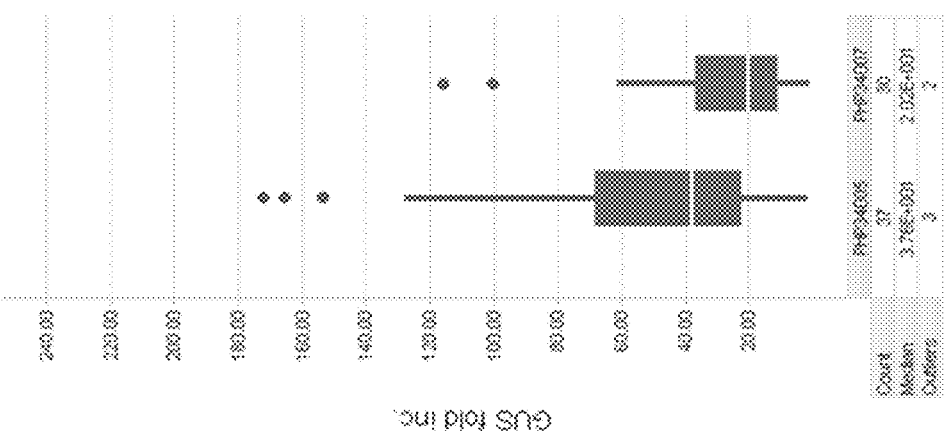
FIG. 4A and FIG. 4B show quantitative analysis of GUS reporter gene expression in Gaspe Flint derived maize lines stably transformed with 1.0 kb SB-ACTIN (PHP34007) and PINII (PHP34005) terminator constructs.
Figure 4A:
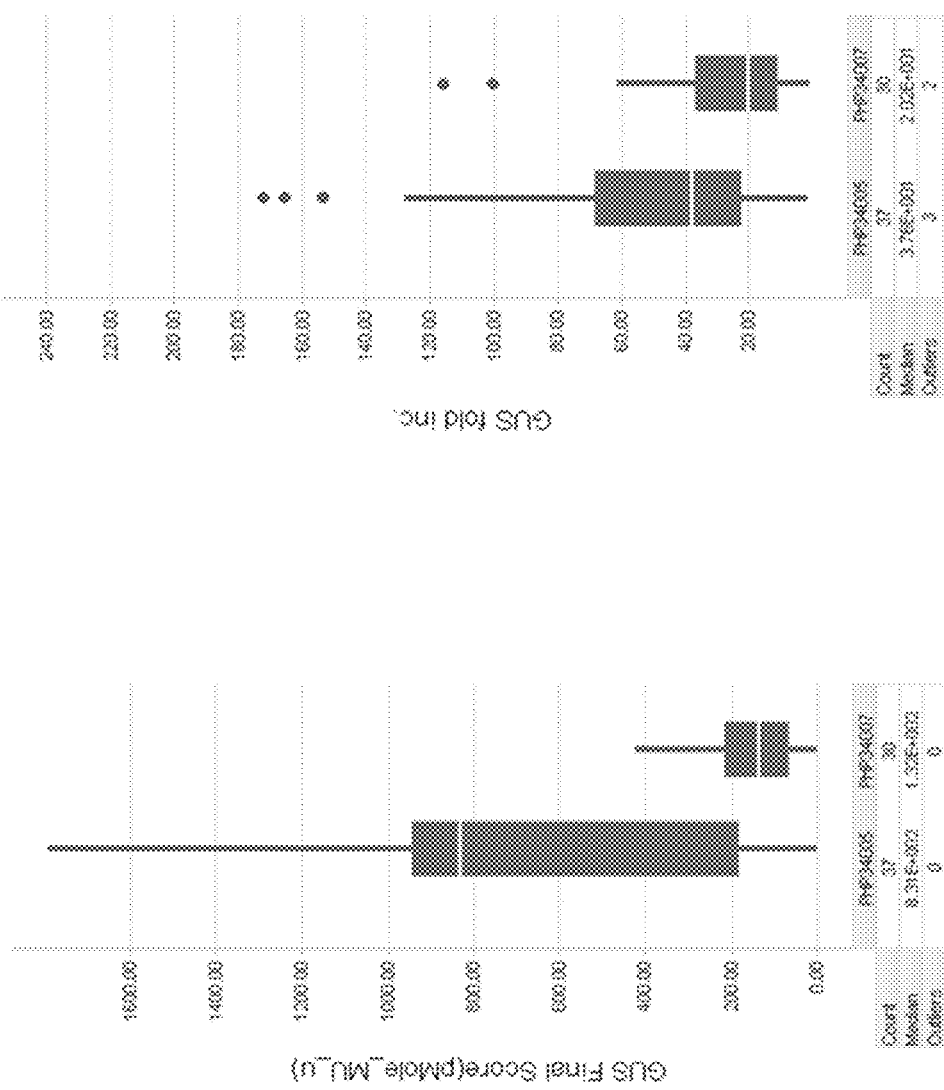

Plants were grown in the greenhouse and leaves were sampled at the R1 stage of development for expression analysis. Multiple plants were tested for each construct. Each plant was analyzed for expression of the GUS gene. GUS gene with the 1.0 kb SB-ACTIN terminator had GUS expression in the same range as that of PINII terminator at both the protein (FIG. 4A) and transcript (FIG. 4B) level.

Quantitative Reverse Transcriptase PCR (qRT-PCR) to Determine Read-Through Transcription Through the SB-ACTIN Terminator:

qRT-PCR assays were performed with leaf tissue from the stable transformants generated using PHP34007 and PHP34005. Each plant was tested for the presence of read-through transcript that had passed through the PINII terminator and the 1.0 kb SB-ACTIN terminator (SEQ ID NO: 1). To assess presence of products that would indicate that transcription was continuing past the terminator, amplification was targeted downstream of the terminator being tested. Two primer sets were designed downstream of the tested terminators.

Primer set Term1~100 nt from the terminator

Primer set Term2.1~500 nt from the terminator

Multiple plants were tested for each construct. The primers are shown in Table 3.

TABLE 3

| Primer/Probe | Name | Type | Sequence | FluorqPCR Assay |
|---|---|---|---|---|
| Term2.1[1] | Term2.1F | fwd | CTGTCAGTTCCAAACGTAAAACG (SEQ ID NO: 11) | - SYBR |
| Term2.1[1] | Term2.1R | rev | AATCTGATCATGAGCGGAGAATTAA (SEQ ID NO: 12) | - SYBR |
| Term1[1] | Term 1F | fwd | TCCCGGGTCCTTAGGAAGAC (SEQ ID NO: 13) | - Taqman |
| Term1[1] | Term 1R | rev | TGGATTCAGCAGGCCTAGAAG (SEQ ID NO: 14) | - Taqman |
| Term1[1] | Term_1P | probe | TCCTCAGGATTTAAATGG (SEQ ID NO: 15) | FAM Taqman |
| Actin[2] | Actin_MGB_F | fwd | CTTCGAATGCCCAGCAATGT (SEQ ID NO: 16) | - Taqman |
| Actin[2] | Actin_MGB_R | rev | GTTCGCCCACTAGCGTACAAC (SEQ ID NO: 17) | - Taqman |
| Actin[2] | Actin_VIC_P | probe | TCGAGGCTGTTCTTT (SEQ ID NO: 18) | VIC Taqman |

[1]Post-Terminator Primer Set
[2]Reference Gene

The test plants were classified into 3 categories depending on the qRT-PCR results:

1. Plants showing complete termination: where all GUS transcripts are completely terminated before they reached the specific primer set location;

2. Plants showing a high degree of termination: where a large portion of the GUS transcripts are terminated before they reached the specific primer set location, also defined as:

Primer set Term1—ΔCT>13
Primer set Term2.1—ΔCT>9; and

3. Plants showing poor termination.

As can be see from FIG. 5, the 1.0 kb SB-ACTIN terminator proved to have fewer "poorly terminating" plants than the PINII terminator (FIG. 5). Thus the qRT-PCR score for presence of transcripts that had proceeded through the terminator was lower for the SB-ACTIN terminator than that for the PINII terminator.

---

What is claimed is:

1. A recombinant DNA construct comprising an isolated polynucleotide sequence and a terminator sequence set forth in SEQ ID NO:2 or SEQ ID NO:1, wherein said terminator sequence functions as a transcriptional terminator in a plant cell, and wherein said polynucleotide sequence is heterologous to said terminator sequence.

2. A plant comprising the recombinant DNA construct of claim 1.

3. The plant of claim 2 wherein the plant is a monocot.

4. The plant of claim 2 wherein the plant is a maize plant.

5. A seed comprising the recombinant DNA construct of claim 1.

6. The seed of claim 5 wherein the seed is from a monocot plant.

7. The seed of claim 5 wherein the seed is from a maize plant.

8. A method of expressing a polynucleotide sequence in a plant, comprising the steps of:

(a) introducing into a regenerable plant cell the recombinant DNA construct of claim 1, wherein said polynucleotide sequence is heterologous to said terminator sequence;
(b) regenerating a transgenic plant from the regenerable plant cell of step (a), wherein the transgenic plant comprises the recombinant DNA construct of claim 1; and
(c) obtaining a progeny plant or seed from the transgenic plant of step (b), wherein the progeny plant or seed comprises the recombinant DNA construct of claim 1 and exhibits expression of the heterologous polynucleotide.

9. The method of claim 8, wherein the plant is a monocot plant.

10. The method of claim 8, wherein the plant is a maize plant.

\* \* \* \* \*

SEQUENCE LISTING

<160> NUMBER OF SEQ ID NOS: 20

<210> SEQ ID NO 1
<211> LENGTH: 1043
<212> TYPE: DNA
<213> ORGANISM: Sorghum bicolor

<400> SEQUENCE: 1

```
gttttctca gacagttttc taaaaaaagg gcgtttctgg ggaagttcga gatggttcgt      60
aaggtgttac tggctcctgt gaaccaatac atgatactgc catgataagg gttataatta     120
gtcaagcaga gtaagaagaa acaacagtag cagtgactcc gattcctgaa gatgagtcat     180
atttgtcttg tgctcctgct gtatgaaatg gatcgcatgt gtatattcgt cgccgcgccg     240
cactggtgta acctgttgcc tcagagtttg cttttagctg gttctgtttt aaaaataagt     300
actgtttttt ggttggctgc aagccattct gaacttcagt ttaccaattg tttttatgtt     360
gtggttgaat attttaattt tttatttaat gtttggttct ttttttatat atatttgcaa     420
aaatgataca agtggtcaag ttttcatata gtatgggctc tatttcctag agctctacct     480
ctaggaacga attttgtgga ggttttcttt tggctagtta ggcaaagtcc ccatatcttg     540
caggctaaat caagaagaag ctctgtcaaa cagttttttt tactgaaaag tgattaaaga     600
gtagtttctc ctagatcact tcagagttta tcctagagaa tcatgggaat caaattcagt     660
tagaggatca tttcttacaa agaatcaact ttcgtagaga atctaaagca gaaagagctt     720
tgacaaactt acccttagag caattccaac attctcgcgt gagtttcttc gcgccgttgt     780
```

-continued

```
tttgcggtga cttcatctgg acgtcccgcg acatagagac gcttgtattg atcatgagag      840
cttgtgtggt catacacaat ataattgtta aagatgaaag agatgtggac cttaatgagc      900
gattcgactt tgatggtgaa aatgtgcaac cttctcatgg tatttctact cgcacactag      960
ctgaatttat tgaagctcat aaaaagatcc gagacaaaga aatacatttt caattgaaag     1020
aagacctaat caagcactta tgg                                             1043
```

<210> SEQ ID NO 2
<211> LENGTH: 517
<212> TYPE: DNA
<213> ORGANISM: Sorghum bicolor

<400> SEQUENCE: 2

```
gttttttctca gacagttttc taaaaaaagg gcgtttctgg ggaagttcga gatggttcgt       60
aaggtgttac tggctcctgt gaaccaatac atgatactgc catgataagg gttataatta      120
gtcaagcaga gtaagaagaa acaacagtag cagtgactcc gattcctgaa gatgagtcat      180
atttgtcttg tgctcctgct gtatgaaatg gatcgcatgt gtatattcgt cgccgcgccg      240
cactggtgta acctgttgcc tcagagtttg cttttagctg gttctgtttt aaaaataagt      300 actgttttt ggttggctgc aagccattct gaacttcagt ttaccaattg tttttatgtt      360
gtggttgaat atttaatttt tttatttaat gtttggttct tttttatat atatttgcaa      420 aaatgataca agtggtcaag ttttcatata gtatgggctc tatttcctag agctctacct      480
ctaggaacga attttgtgga ggttttcttt tggctag                               517
```

<210> SEQ ID NO 3
<211> LENGTH: 39
<212> TYPE: DNA
<213> ORGANISM: artificial sequence
<220> FEATURE:
<223> OTHER INFORMATION: forward primer TMS2120

<400> SEQUENCE: 3

```
actagtgttt ttctcagaca gttttctaaa aaagggcg                               39
```

<210> SEQ ID NO 4
<211> LENGTH: 30
<212> TYPE: DNA
<213> ORGANISM: artificial sequence
<220> FEATURE:
<223> OTHER INFORMATION: reverse primer TMS2132

<400> SEQUENCE: 4

```
gaattcccat aagtgcttga ttaggtcttc                                        30
```

<210> SEQ ID NO 5
<211> LENGTH: 4072
<212> TYPE: DNA
<213> ORGANISM: artificial sequence
<220> FEATURE:
<223> OTHER INFORMATION: plasmid PHP32622

<400> SEQUENCE: 5

```
gggcgaattg ggcccgacgt cgcatgctcc cggccgccat ggcggccgcg ggaattccat       60
tactagtgtt tttctcagac agttttctaa aaagggcg tttctgggga agttcgagat       120
ggttcgtaag gtgttactgg ctcctgtgaa ccaatacatg atactgccat gataagggtt      180
ataattagtc aagcagagta agaagaaaca acagtagcag tgactccgat tcctgaagat      240
```

```
gagtcatatt tgtcttgtgc tcctgctgta tgaaatggat cgcatgtgta tattcgtcgc    300
cgcgccgcac tggtgtaacc tgttgcctca gagtttgctt ttagctggtt ctgttttaaa    360
aataagtact gttttttggt tggctgcaag ccattctgaa cttcagttta ccaattgttt    420
ttatgttgtg gttgaatatt ttaattttt atttaatgtt tggttctttt tttatatata    480
tttgcaaaaa tgatacaagt ggtcaagttt tcatatagta tgggctctat ttcctagagc    540
tctacctcta ggaacgaatt tgtggaggt tttcttttgg ctagttaggc aaagtcccca    600
tatcttgcag gctaaatcaa gaagaagctc tgtcaaacag ttttttttac tgaaaagtga    660
ttaaagagta gtttctccta gatcacttca gagtttatcc tagagaatca tgggaatcaa    720
attcagttag aggatcattt cttacaaaga atcaactttc gtagagaatc taaagcagaa    780
agagctttga caaacttacc cttagagcaa ttccaacatt ctcgcgtgag tttcttcgcg    840
ccgttgtttt gcggtgactt catctggacg tcccgcgaca tagagacgct tgtattgatc    900
atgagagctt gtgtggtcat acacaatata attgttaaag atgaaagaga tgtggacctt    960
aatgagcgat tcgactttga tggtgaaaat gtgcaacctt ctcatggtat ttctactcgc   1020
acactagctg aatttattga agctcataaa aagatccgag acaaagaaat acattttcaa   1080
ttgaaagaag acctaatcaa gcacttatgg gaattcaatc actagtgaat tcgcggccgc   1140
ctgcaggtcg accatatggg agagctccca acgcgttgga tgcatagctt gagtattcta   1200
tagtgtcacc taaatagctt ggcgtaatca tggtcatagc tgtttcctgt gtgaaattgt   1260
tatccgctca caattccaca acatacga gccggaagca taaagtgtaa agcctggggt   1320
gcctaatgag tgagctaact cacattaatt gcgttgcgct cactgcccgc tttccagtcg   1380
ggaaacctgt cgtgccagct gcattaatga atcggccaac gcgcgggag aggcggtttg   1440 cgtattgggc gctcttccgc ttcctcgctc actgactcgc tgcgctcggt cgttcggctg   1500
cggcgagcgg tatcagctca ctcaaaggcg gtaatacggt tatccacaga atcagggat    1560 aacgcaggaa agaacatgtg agcaaaaggc cagcaaaagg ccaggaaccg taaaaaggcc   1620
gcgttgctgg cgttttcca taggctccgc cccctgacg agcatcacaa aaatcgacgc    1680
tcaagtcaga ggtggcgaaa cccgacagga ctataaagat accaggcgtt ccccctgga    1740 agctccctcg tgcgctctcc tgttccgacc ctgccgctta ccggatacct gtccgccttt   1800
ctcccttcgg gaagcgtggc gctttctcat agctcacgct gtaggtatct cagttcggtg   1860
taggtcgttc gctccaagct gggctgtgtg cacgaacccc ccgttcagcc cgaccgctgc   1920
gccttatccg gtaactatcg tcttgagtcc aacccggtaa gacacgactt atcgccactg   1980
gcagcagcca ctggtaacag gattagcaga gcgaggtatg taggcggtgc tacagagttc   2040
ttgaagtggt ggcctaacta cggctacact agaagaacag tatttggtat ctgcgctctg   2100
ctgaagccag ttaccttcgg aaaaagagtt ggtagctctt gatccggcaa acaaaccacc   2160
gctggtagcg gtggtttttt tgtttgcaag cagcagatta cgcgcagaaa aaaggatct    2220 caagaagatc ctttgatctt ttctacgggg tctgacgctc agtggaacga aaactcacgt   2280
taagggattt tggtcatgag attatcaaaa aggatcttca cctagatcct tttaaattaa   2340
aaatgaagtt ttaaatcaat ctaaagtata tatgagtaaa cttggtctga cagttaccaa   2400
tgcttaatca gtgaggcacc tatctcagcg atctgtctat ttcgttcatc catagttgcc   2460 tgactcccg tcgtgtagat aactacgata cgggagggct taccatctgg ccccagtgct   2520
gcaatgatac cgcgagaccc acgctcaccg gctccagatt tatcagcaat aaaccagcca   2580
gccggaaggg ccgagcgcag aagtggtcct gcaactttat ccgcctccat ccagtctatt   2640
```

```
aattgttgcc gggaagctag agtaagtagt tcgccagtta atagtttgcg caacgttgtt      2700
gccattgcta caggcatcgt ggtgtcacgc tcgtcgtttg gtatggcttc attcagctcc      2760
ggttcccaac gatcaaggcg agttacatga tcccccatgt tgtgcaaaaa agcggttagc      2820
tccttcggtc ctccgatcgt tgtcagaagt aagttggccg cagtgttatc actcatggtt      2880
atggcagcac tgcataattc tcttactgtc atgccatccg taagatgctt ttctgtgact      2940
ggtgagtact caaccaagtc attctgagaa tagtgtatgc ggcgaccgag ttgctcttgc      3000
ccggcgtcaa tacgggataa taccgcgcca catagcagaa ctttaaaagt gctcatcatt      3060
ggaaaacgtt cttcggggcg aaaactctca aggatcttac cgctgttgag atccagttcg      3120
atgtaaccca ctcgtgcacc caactgatct tcagcatctt ttactttcac cagcgtttct      3180
gggtgagcaa aaacaggaag gcaaaatgcc gcaaaaaagg gaataagggc gacacggaaa      3240
tgttgaatac tcatactctt ccttttttcaa tattattgaa gcatttatca gggttattgt      3300
ctcatgagcg gatacatatt tgaatgtatt tagaaaaata acaaataggg gttccgcgc      3360 acatttcccc gaaaagtgcc acctgatgcg gtgtgaaata ccgcacagat gcgtaaggag      3420
aaaataccgc atcaggaaat tgtaagcgtt aatattttgt taaaattcgc gttaaatttt      3480
tgttaaatca gctcattttt taaccaatag gccgaaatcg gcaaaatccc ttataaatca      3540
aaagaataga ccgagatagg gttgagtgtt gttccagttt ggaacaagag tccactatta      3600
aagaacgtgg actccaacgt caaagggcga aaaccgtct atcagggcga tggcccacta      3660
cgtgaaccat caccctaatc aagttttttg gggtcgaggt gccgtaaagc actaaatcgg      3720
aaccctaaag ggagccccccg atttagagct tgacggggaa agccggcgaa cgtggcgaga      3780
aaggaaggga agaaagcgaa aggagcgggc gctagggcgc tggcaagtgt agcggtcacg      3840
ctgcgcgtaa ccaccacacc cgccgcgctt aatgcgccgc tacagggcgc gtccattcgc      3900
cattcaggct gcgcaactgt tgggaagggc gatcggtgcg ggcctcttcg ctattacgcc      3960
agctggcgaa aggggggatgt gctgcaaggc gattaagttg ggtaacgcca gggttttccc      4020
agtcacgacg ttgtaaaacg acggccagtg aattgtaata cgactcacta ta              4072
```

<210> SEQ ID NO 6
<211> LENGTH: 51420
<212> TYPE: DNA
<213> ORGANISM: artificial sequence
<220> FEATURE:
<223> OTHER INFORMATION: plasmid PHP34007

<400> SEQUENCE: 6

```
acgtgaccct agtcacttag gttaccagag ctggtcacct ttgtccacca agatggaact        60
gcggccgctc attaattaag tcaggcgcgc ctctagttga agacacgttc atgtcttcat       120
cgtaagaaga cactcagtag tcttcggcca gaatggccat ctggattcag caggcctaga       180
aggccattta atcctgagg atctggtctt cctaaggacc cggatatcg ctatcaactt       240 tgtatagaaa agttgggccg aattcccata agtgcttgat taggtcttct ttcaattgaa       300
aatgtatttc tttgtctcgg atcttttat gagcttcaat aaattcagct agtgtgcgag       360
tagaaatacc atgagaaggt tgcacatttt caccatcaaa gtcgaatcgc tcattaaggt       420
ccacatctct ttcatcttta acaattatat tgtgtatgac cacacaagct ctcatgatca       480
atacaagcgt ctctatgtcg cgggacgtcc agatgaagtc accgcaaaac aacggcgcga       540
agaaactcac gcgagaatgt tggaattgct ctaagggtaa gtttgtcaaa gctctttctg       600
```

```
ctttagattc tctacgaaag ttgattcttt gtaagaaatg atcctctaac tgaatttgat      660
tcccatgatt ctctaggata aactctgaag tgatctagga gaaactactc tttaatcact      720
tttcagtaaa aaaaactgtt tgacagagct tcttcttgat ttagcctgca agatatgggg      780
actttgccta actagccaaa agaaaacctc cacaaaattc gttcctagag gtagagctct      840
aggaaataga gcccatacta tatgaaaact tgaccacttg tatcattttt gcaaatatat      900
ataaaaaaag aaccaaacat taaataaaaa attaaaatat tcaaccacaa cataaaaaca      960
attggtaaac tgaagttcag aatggcttgc agccaaccaa aaaacagtac ttattttttaa    1020 aacagaacca gctaaaagca aactctgagg caacaggtta caccagtgcg gcgcggcgac     1080
gaatatacac atgcgatcca tttcatacag caggagcaca agacaaatat gactcatctt     1140
caggaatcgg agtcactgct actgttgttt cttcttactc tgcttgacta attataaccc     1200
ttatcatggc agtatcatgt attggttcac aggagccagt aacaccttac gaaccatctc     1260
gaacttcccc agaaacgccc tttttttaga aaactgtctg agaaaaacac tagtaagctt     1320
agatcttcat tgtttgcctc cctgctgcgg ttttcaccg aagttcatgc cagtccagcg      1380
tttttgcagc agaaaagccg ccgacttcgg tttgcggtcg cgagtgaaga tccctttctt     1440
gttaccgcca acgcgcaata tgccttgcga ggtcgcaaaa tcggcgaaat tccatacctg     1500 ttaccgacg acggcgctga cgcgatcaaa gacgcggtga tacatatcca gccatgcaca      1560
ctgatactct tcactccaca tgtcggtgta cattgagtgc agcccggcta acgtatccac     1620
gccgtattcg gtgatgataa tcggctgatg cagtttctcc tgccaggcca gaagttcttt     1680
ttccagtacc ttctctgccg tttccaaatc gccgctttgg acataccatc cgtaataacg     1740
gttcaggcac agcacatcaa agagatcgct aatggtatcg gtgtgagcgt cgcagaacat     1800
tacattgacg caggtgatcg gacgcgtcgg gtcgagtta cgcgttgctt ccgccagtgg      1860
cgcgaaatat tcccgtgcac cttgcggacg ggtatccggt tcgttggcaa tactccacat     1920
caccacgctt gggtggtttt tgtcacgcgc tatcagctct ttaatcgcct gtaagtgcgc     1980
ttgctgagtt tccccgttga ctgcctcttc gctgtacagt tctttcggct tgttgcccgc     2040
ttcgaaacca atccctaaag agaggttaaa gccgacagca gcagtttcat caatcaccac     2100
gatgccatgt tcatctgccc agtcgagcat ctcttcagcg taagggtaat gcgaggtacg     2160
gtaggagttg gccccaatcc agtccattaa tgcgtggtcg tgcaccatca gcacgttatc     2220
gaatcctttg ccacgcaagt ccgcatcttc atgacgacca aagccagtaa agtagaacgg     2280
tttgtggtta atcaggaact gttggcccctt cactgccact gaccggatgc cgacgcgaag    2340
cgggtagata tcacactctg tctggctttt ggctgtgacg cacagttcat agagataacc     2400
ttcacccggt tgccagaggt gcggattcac cacttgcaaa gtcccgctag tgccttgtcc     2460
agttgcaacc acctgttgat ccgcatcacg cagttcaacg ctgacatcac cattggccac     2520
cacctgccag tcaacagacg cgtggttaca gtcttgcgcg acatgcgtca ccacggtgat     2580
atcgtccacc caggtgttcg gcgtggtgta gagcattacg ctgcgatgga ttccggcata     2640
gttaaagaaa tcatggaagt aagactgctt tttcttgccg ttttcgtcgg taatcaccat     2700
tcccggcggg atagtctgcc agttcagttc gttgttcaca caaacggtga tacctgcaca     2760
tcaacaaatt ttggtcatat attagaaaag ttataaatta aaatatacac acttataaac     2820
tacagaaaag caattgctat atactacatt cttttatttt gaaaaaaata tttgaaatat     2880
tatattacta ctaattaatg ataattatta tatatatatc aaaggtagaa gcagaaactt     2940
acgtacactt ttcccggcaa taacatacgg cgtgacatcg gcttcaaatg gcgtatagcc     3000
```

```
gccctgatgc tccatcactt cctgattatt gacccacact ttgccgtaat gagtgaccgc    3060
atcgaaacgc agcacgatac gctggcctgc ccaaccttttc ggtataaaga cttcgcgctg    3120
ataccagacg ttgcccgcat aattacgaat atctgcatcg gcgaactgat cgttaaaact    3180
gcctggcaca gcaattgccc ggcttttctg taacgcgctt tcccaccaac gctgatcaat    3240
tccacagttt tcgcgatcca gactgaatgc ccacaggccg tcgagttttt tgatttcacg    3300
ggttggggtt tctacaggac ggaccatggt gtcgtgtgga tccaaattgt atgcaaggtg    3360
aatgactttc ttttcgtaaa ctagatagga gtactcctcc aggatgctta acccgtattg    3420
acgtacagag gtctatgatc cttttgttta taaaggagct tgtagttcag tcagtcttat    3480
acttcacgat gcccatgttt ctatatagga tattatcttg gctttgtaag tacttcacgc    3540
aggttatgtt ctgtttctag gatattatcc tcatacatgc gaagaaccaa ttttccccc    3600 attctcttcg ggtacttttt cttgggtagg catgctctct tggaccaact agcataaaac    3660
ataatcattt ttccctacag ccttgaccag ctataatcga aatcatgctc attttctaa    3720 gaaagactga atacagctcc aatttaaaca atttaaatca taaacttgta actcaattag    3780
agaaaagcag agcccttcgg ctcctatcta aaggaattac cccatgaaag ccataaaaac    3840
gaaccttgct ctgataccag acgggtctac gctcgcggaa ctaggatctt gcgctctact    3900
cgcacaaagt gaactcgcac aaagtgtgtt tcaagcacag aagtttttat ttctcaaatc    3960
aggagtaaac tcgcgttgtg gtgcgtgttt gcaacctgaa tacaaggctc cttatataga    4020
gagttgtgga gctttctggc atcgttaggt ggcatccacc aataatgcag ataagcatca    4080
tcacatgtct ctggcctaac aactttgcgt aagaatcctg caaagttact aaaggtcatc    4140
gtgcgtgact agacaacgca caccgacaaa cttaaaataa agagacatta tactttgtct    4200 cctcttttaca taaagtgagt ggtatccagc tcactccgca tcttatcagt cttcacaccg    4260
gttggtatca acacgtggta ggggtccgcc acttccgctt cagtcatcat tactgatatc    4320
cagcagatct agagcatctt caataagata ttcttgttct gcacgcagat tttcttgctc    4380
cctcagtaat tcctcccaca gtgagtcttc tgatatttct tcaagtttct tctcccatct    4440
gatcttttcc tgcacaaacg agtcaatttg gtctttccag acccaagtaa aacaagtgtt    4500
agtttcacag gagtaaaact ccctgtcagg atttctggat gttctggaga tcttcagttt    4560
tgctggttta ttgcatccac atttgaaaac cggctcttca cttagtgtta gcacattgat    4620
ttgatgcaac ctgtagcctt tgctcaacca gtcttcatat ctttttacaa catcattaac    4680
tctctgtttt gcatcggtgt ttcccttgtg aaatacctcc tccactgcat tgatcaacac    4740
accttcagat tgatgctttt ccggatggag aataatcttt accagtcttg acagagtgtc    4800
tgctaaaacg ttgtccttttc cgtcaatgtg ttcaaactta atctcaagac ctgtcccggt    4860
aatgtaatct gtgaaggcaa gccatctgac tcttgatggt ttatgatcac tgcttttctt    4920
gtaaaagctc actattgctt gactgtcagt tctgattatg agctctttgt aagcttggtc    4980
acccggtccg ggcctagaag gccagcttcg gccgccccgg gcaactttat tatacaaagt    5040
tgatagatat cggaccgatt aaactttaat tcggtccgaa gcttgcatgc ctgcagtgca    5100
gcgtgacccg tcgtgccccc tctctagaga taatgagcat tgcatgtcta agttataaaa    5160
aattaccaca tatttttttt gtcacacttg tttgaagtgc agtttatcta tctttataca    5220
tatatttaaa cttactctca cgaataatat aatctatagt actacaataa tatcagtgtt    5280
ttagagaatc atataaatga acagttagac atggtctaaa ggacaattga gtattttgac    5340
```

-continued

| | | | | | |
|---|---|---|---|---|---|
| aacaggactc | tacagtttta | tcttttagt | gtgcatgtgt | tctcctttt | ttttgcaaat | 5400 |
| agcttcacct | atataatact | tcatccattt | tattagtaca | tccatttagg | gtttagggtt | 5460 |
| aatggttttt | atagactaat | tttttagta | catctatttt | attctatttt | agcctctaaa | 5520 |
| ttaagaaaac | taaaactcta | ttttagtttt | tttatttaat | aatttagata | taaaatagaa | 5580 |
| taaaataaag | tgactaaaaa | ttaaacaaat | acccttaag | aaattaaaaa | aactaaggaa | 5640 |
| acatttttct | tgtttcgagt | agataatgcc | agcctgttaa | acgccgtcga | cgagtctaac | 5700 |
| ggacaccaac | cagcgaacca | gcagcgtcgc | gtcgggccaa | gcgaagcaga | cggcacggca | 5760 |
| tctctgtcgc | tgcctctgga | cccctctcga | gagttccgct | ccaccgttgg | acttgctccg | 5820 |
| ctgtcggcat | ccagaaattg | cgtggcggag | cggcagacgt | gagccggcac | ggcaggcggc | 5880 |
| ctcctcctcc | tctcacggca | ccggcagcta | cgggggattc | ctttcccacc | gctccttcgc | 5940 |
| tttcccttcc | tcgcccgccg | taataaatag | acaccccctc | cacaccctct | ttccccaacc | 6000 |
| tcgtgttgtt | cggagcgcac | acacacacaa | ccagatctcc | cccaaatcca | cccgtcggca | 6060 |
| cctccgcttc | aaggtacgcc | gctcgtcctc | cccccccccc | ctctctacct | tctctagatc | 6120 |
| ggcgttccgg | tccatgcatg | gttagggccc | ggtagttcta | cttctgttca | tgtttgtgtt | 6180 |
| agatccgtgt | ttgtgttaga | tccgtgctgc | tagcgttcgt | acacggatgc | gacctgtacg | 6240 |
| tcagacacgt | tctgattgct | aacttgccag | tgtttctctt | tggggaatcc | tgggatggct | 6300 |
| ctagccgttc | cgcagacggg | atcgatttca | tgatttttt | tgtttcgttg | catagggttt | 6360 |
| ggtttgccct | tttcctttat | ttcaatatat | gccgtgcact | tgtttgtcgg | gtcatctttt | 6420 |
| catgcttttt | tttgtcttgg | ttgtgatgat | gtggtctggt | tgggcggtcg | ttctagatcg | 6480 |
| gagtagaatt | ctgtttcaaa | ctacctggtg | gatttattaa | ttttggatct | gtatgtgtgt | 6540 |
| gccatacata | ttcatagtta | cgaattgaag | atgatggatg | gaaatatcga | tctaggatag | 6600 |
| gtatacatgt | tgatgcgggt | tttactgatg | catatacaga | gatgctttt | gttcgcttgg | 6660 |
| ttgtgatgat | gtggtgtggt | tgggcggtcg | ttcattcgtt | ctagatcgga | gtagaatact | 6720 |
| gtttcaaact | acctggtgta | tttattaatt | ttggaactgt | atgtgtgtgt | catacatctt | 6780 |
| catagttacg | agtttaagat | ggatggaaat | atcgatctag | gataggtata | catgttgatg | 6840 |
| tgggttttac | tgatgcatat | acatgatggc | atatgcagca | tctattcata | tgctctaacc | 6900 |
| ttgagtacct | atctattata | ataaacaagt | atgttttata | attattttga | tcttgatata | 6960 |
| cttggatgat | ggcatatgca | gcagctatat | gtggattttt | ttagccctgc | cttcatacgc | 7020 |
| tatttatttg | cttggtactg | tttctttgt | cgatgctcac | cctgttgttt | ggtgttactt | 7080 |
| ctgcaggtcg | actttaactt | agcctaggat | ccacacgaca | ccatgtcccc | cgagcgccgc | 7140 |
| cccgtcgaga | tccgcccggc | caccgccgcc | gacatggccg | ccgtgtgcga | catcgtgaac | 7200 |
| cactacatcg | agacctccac | cgtgaacttc | cgcaccgagc | cgcagacccc | gcaggagtgg | 7260 |
| atcgacgacc | tggagcgcct | ccaggaccgc | tacccgtggc | tcgtggccga | ggtgagggc | 7320 |
| gtggtggccg | gcatcgccta | cgccggcccg | tggaaggccc | gcaacgccta | cgactggacc | 7380 |
| gtggagtcca | ccgtgtacgt | gtcccaccgc | caccagcgcc | tcggcctcgg | ctccaccctc | 7440 |
| tacacccacc | tcctcaagag | catgaggcc | cagggcttca | agtccgtggt | ggccgtgatc | 7500 |
| ggcctcccga | acgacccgtc | cgtgcgcctc | cacgaggccc | tcggctacac | cgcccgcggc | 7560 |
| accctccgcg | ccgccggcta | caagcacggc | ggctggcacg | acgtcggctt | ctggcagcgc | 7620 |
| gacttcgagc | tgccggcccc | gccgcgcccg | gtgcgcccgg | tgacgcagat | ctgagtcgaa | 7680 |
| acctagactt | gtccatcttc | tggattggcc | aacttaatta | atgtatgaaa | taaaaggatg | 7740 |

```
cacacatagt gacatgctaa tcactataat gtgggcatca aagttgtgtg ttatgtgtaa   7800
ttactagtta tctgaataaa agagaaagag atcatccata tttcttatcc taaatgaatg   7860
tcacgtgtct ttataattct ttgatgaacc agatgcattt cattaaccaa atccatatac   7920
atataaatat taatcatata taattaatat caattgggtt agcaaaacaa atctagtcta   7980
ggtgtgtttt gcgaatgcgg ccgataagtg actagggtca cgtgacccta gtcacttagg   8040
taccgagctc gaattcattc cgattaatcg tggcctcttg ctcttcagga tgaagagcta   8100
tgtttaaacg tgcaagcgct actagacaat tcagtacatt aaaaacgtcc gcaatgtgtt   8160
attaagttgt ctaagcgtca atttgtttac accacaatat atcctgccac cagccagcca   8220
acagctcccc gaccggcagc tcggcacaaa atcaccactc gatacaggca gcccatcagt   8280
ccgggacggc gtcagcggga gagccgttgt aaggcggcag actttgctca tgttaccgat   8340
gctattcgga agaacggcaa ctaagctgcc gggtttgaaa cacggatgat ctcgcggagg   8400
gtagcatgtt gattgtaacg atgacagagc gttgctgcct gtgatcaaat atcatctccc   8460
tcgcagagat ccgaattatc agccttctta ttcatttctc gcttaaccgt gacaggctgt   8520
cgatcttgag aactatgccg acataatagg aaatcgctgg ataaagccgc tgaggaagct   8580
gagtggcgct atttctttag aagtgaacgt tgacgatcgt cgaccgtacc ccgatgaatt   8640
aattcggacg tacgttctga acacagctgg atacttactt gggcgattgt catacatgac   8700
atcaacaatg tacccgtttg tgtaaccgtc tcttggaggt tcgtatgaca ctagtggttc   8760
ccctcagctt gcgactagat gttgaggcct aacattttat tagagagcag gctagttgct   8820
tagatacatg atcttcaggc cgttatctgt cagggcaagc gaaaattggc catttatgac   8880
gaccaatgcc ccgcagaagc tcccatcttt gccgccatag acgccgcgcc ccccttttgg   8940
ggtgtagaac atccttttgc cagatgtgga aaagaagttc gttgtcccat tgttggcaat   9000
gacgtagtag ccggcgaaag tgcgagaccc atttgcgcta tatataagcc tacgatttcc   9060
gttgcgacta ttgtcgtaat tggatgaact attatcgtag ttgctctcag agttgtcgta   9120
atttgatgga ctattgtcgt aattgcttat ggagttgtcg tagttgcttg gagaaatgtc   9180
gtagttggat ggggagtagt catagggaag acgagcttca tccactaaaa caattggcag   9240
gtcagcaagt gcctgccccg atgccatcgc aagtacgagg cttagaacca ccttcaacag   9300
atcgcgcata gtcttcccca gctctctaac gcttgagtta agccgcgccg cgaagcggcg   9360
tcggcttgaa cgaattgtta gacattattt gccgactacc ttggtgatct cgcctttcac   9420
gtagtgaaca aattcttcca actgatctgc gcgcgaggcc aagcgatctt cttgtccaag   9480
ataagcctgc ctagcttcaa gtatgacggg ctgatactgg gccggcaggc gctccattgc   9540
ccagtcggca gcgacatcct tcggcgcgat tttgccggtt actgcgctgt accaaatgcg   9600
ggacaacgta agcactacat ttcgctcatc gccagcccag tcgggcggcg agttccatag   9660
cgttaaggtt tcatttagcg cctcaaatag atcctgttca ggaaccggat caaagagttc   9720
ctccgccgct ggacctacca aggcaacgct atgttctctt gcttttgtca gcaagatagc   9780
cagatcaatg tcgatcgtgg ctggctcgaa gatacctgca agaatgtcat tgcgctgcca   9840
ttctccaaat tgcagttcgc gcttagctgg ataacgccac ggaatgatgt cgtcgtgcac   9900
aacaatggtg acttctacag cgcggagaat ctcgctctct ccaggggaag ccgaagtttc   9960
caaaaggtcg ttgatcaaag ctcgccgcgt tgtttcatca agccttacag tcaccgtaac  10020
cagcaaatca atatcactgt gtggcttcag gccgccatcc actgcggagc cgtacaaatg  10080
```

```
tacggccagc aacgtcggtt cgagatggcg ctcgatgacg ccaactacct ctgatagttg   10140
agtcgatact tcggcgatca ccgcttccct catgatgttt aactcctgaa ttaagccgcg   10200
ccgcgaagcg gtgtcggctt gaatgaattg ttaggcgtca tcctgtgctc ccgagaacca   10260
gtaccagtac atcgctgttt cgttcgagac ttgaggtcta gttttatacg tgaacaggtc   10320
aatgccgccg agagtaaagc cacattttgc gtacaaattg caggcaggta cattgttcgt   10380
ttgtgtctct aatcgtatgc caaggagctg tctgcttagt gcccactttt tcgcaaattc   10440
gatgagactg tgcgcgactc ctttgcctcg gtgcgtgtgc gacacaacaa tgtgttcgat   10500
agaggctaga tcgttccatg ttgagttgag ttcaatcttc ccgacaagct cttggtcgat   10560
gaatgcgcca tagcaagcag agtcttcatc agagtcatca tccgagatgt aatccttccg   10620
gtaggggctc acacttctgg tagatagttc aaagccttgg tcggataggt gcacatcgaa   10680
cacttcacga acaatgaaat ggttctcagc atccaatgtt tccgccacct gctcagggat   10740
caccgaaatc ttcatatgac gcctaacgcc tggcacagcg gatcgcaaac ctggcgcggc   10800
ttttggcaca aaaggcgtga caggtttgcg aatccgttgc tgccacttgt taacccttttt   10860 gccagatttg gtaactataa tttatgttag aggcgaagtc ttgggtaaaa actggcctaa   10920
aattgctggg gatttcagga aagtaaacat caccttccgg ctcgatgtct attgtagata   10980
tatgtagtgt atctacttga tcggggggatc tgctgcctcg cgcgtttcgg tgatgacggt   11040
gaaaacctct gacacatgca gctcccggag acggtcacag cttgtctgta agcggatgcc   11100
gggagcagac aagcccgtca gggcgcgtca gcgggtgttg gcgggtgtcg gggcgcagcc   11160
atgacccagt cacgtagcga tagcggagtg tatactggct taactatgcg gcatcagagc   11220
agattgtact gagagtgcac catatgcggt gtgaaatacc gcacagatgc gtaaggagaa   11280
aataccgcat caggcgctct tccgcttcct cgctcactga ctcgctgcgc tcggtcgttc   11340
ggctgcggcg agcggtatca gctcactcaa aggcggtaat acggttatcc acagaatcag   11400
gggataacgc aggaaagaac atgtgagcaa aaggccagca aaaggccagg aaccgtaaaa   11460
aggccgcgtt gctggcgttt ttccataggc tccgccccccc tgacgagcat cacaaaaatc   11520
gacgctcaag tcagaggtgg cgaaacccga caggactata aagataccag gcgtttcccc   11580
ctggaagctc cctcgtgcgc tctcctgttc cgaccctgcc gcttaccgga tacctgtccg   11640
cctttctccc ttcgggaagc gtggcgcttt ctcatagctc acgctgtagg tatctcagtt   11700
cggtgtaggt cgttcgctcc aagctgggct gtgtgcacga accccccgtt cagcccgacc   11760
gctgcgcctt atccggtaac tatcgtcttg agtccaaccc ggtaagacac gacttatcgc   11820
cactggcagc agccactggt aacaggatta gcagagcgag gtatgtaggc ggtgctacag   11880
agttcttgaa gtggtggcct aactacggct acactagaag gacagtattt ggtatctgcg   11940
ctctgctgaa gccagttacc ttcggaaaaa gagttggtag ctcttgatcc ggcaaacaaa   12000
ccaccgctgg tagcggtggt ttttttgttt gcaagcagca gattacgcgc agaaaaaaag   12060
gatctcaaga agatcctttg atcttttcta cggggtctga cgctcagtgg aacgaaaact   12120
cacgttaagg gattttggtc atgagattat caaaaaggat cttcacctag atccttttaa   12180
attaaaaatg aagttttaaa tcaatctaaa gtatatatga gtaaacttgg tctgacagtt   12240
accaatgctt aatcagtgag gcacctatct cagcgatctg tctatttcgt tcatccatag   12300
ttgcctgact ccccgtcgtg tagataacta cgatacggga gggcttacca tctggcccca   12360
gtgctgcaat gataccgcga gacccacgct caccggctcc agatttatca gcaataaacc   12420
agccagccgg aagggccgag cgcagaagtg gtcctgcaac tttatccgcc tccatccagt   12480
```

```
ctattaattg ttgccgggaa gctagagtaa gtagttcgcc agttaatagt ttgcgcaacg    12540
ttgttgccat tgctgcaggg ggggggggggg gggggttcca ttgttcattc cacgacaaa    12600 aacagagaaa ggaaacgaca gaggccaaaa agctcgcttt cagcacctgt cgtttccttt    12660
cttttcagag ggtattttaa ataaaaacat taagttatga cgaagaagaa cggaaacgcc    12720
ttaaaccgga aaattttcat aaatagcgaa aacccgcgag gtcgccgccc cgtaacctgt    12780
cggatcaccg gaaaggaccc gtaaagtgat aatgattatc atctacatat cacaacgtgc    12840
gtggaggcca tcaaaccacg tcaaataatc aattatgacg caggtatcgt attaattgat    12900
ctgcatcaac ttaacgtaaa aacaacttca gacaatacaa atcagcgaca ctgaatacgg    12960
ggcaacctca tgtcccccc cccccccccc ctgcaggcat cgtggtgtca cgctcgtcgt    13020
ttggtatggc ttcattcagc tccggttccc aacgatcaag gcgagttaca tgatccccca    13080
tgttgtgcaa aaaagcggtt agctccttcg gtcctccgat cgttgtcaga agtaagttgg    13140
ccgcagtgtt atcactcatg gttatggcag cactgcataa ttctcttact gtcatgccat    13200
ccgtaagatg cttttctgtg actggtgagt actcaaccaa gtcattctga aatagtgta    13260 tgcggcgacc gagttgctct tgcccggcgt caacacggga taataccgcg ccacatagca    13320
gaactttaaa agtgctcatc attggaaaac gttcttcggg gcgaaaactc tcaaggatct    13380
taccgctgtt gagatccagt tcgatgtaac ccactcgtgc acccaactga tcttcagcat    13440
cttttacttt caccagcgtt tctgggtgag caaaaacagg aaggcaaaat gccgcaaaaa    13500
agggaataag ggcgacacgg aaatgttgaa tactcatact cttccttttt caatattatt    13560
gaagcattta tcagggttat tgtctcatga gcggatacat atttgaatgt atttagaaaa    13620
ataaacaaat aggggttccg cgcacatttc cccgaaaagt gccacctgac gtctaagaaa    13680
ccattattat catgacatta acctataaaa ataggcgtat cacgaggccc tttcgtcttc    13740
aagaattcgg agcttttgcc attctcaccg gattcagtcg tcactcatgg tgatttctca    13800
cttgataacc ttatttttga cgaggggaaa ttaataggtt gtattgatgt tggacgagtc    13860
ggaatcgcag accgatacca ggatcttgcc atcctatgga actgcctcgg tgagttttct    13920
ccttcattac agaaacggct ttttcaaaaa tatggtattg ataatcctga tatgaataaa    13980
ttgcagtttc atttgatgct cgatgagttt ttctaatcag aattggttaa ttggttgtaa    14040
cactggcaga gcattacgct gacttgacgg gacggcggct ttgttgaata aatcgaactt    14100
ttgctgagtt gaaggatcag atcacgcatc ttcccgacaa cgcagaccgt tccgtggcaa    14160
agcaaaagtt caaaatcacc aactggtcca cctacaacaa agctctcatc aaccgtggct    14220
ccctcacttt ctggctggat gatggggcga ttcaggcctg gtatgagtca gcaacaccttt    14280 cttcacgagg cagacctcag cgccagaagg ccgccagaga ggccgagcgc ggccgtgagg    14340
cttggacgct agggcagggc atgaaaaagc ccgtagcggg ctgctacggg cgtctgacgc    14400 ggtgaaagg gggaggggat gttgtctaca tggctctgct gtagtgagtg ggttgcgctc    14460
cggcagcggt cctgatcaat cgtcacccctt tctcggtcct tcaacgttcc tgacaacgag    14520
cctccttttc gccaatccat cgacaatcac cgcgagtccc tgctcgaacg ctgcgtccgg    14580
accggcttcg tcgaaggcgt ctatcgcggc ccgcaacagc ggcgagagcg gagcctgttc    14640
aacggtgccg ccgcgctcgc cggcatcgct gtcgccggcc tgctcctcaa gcacggcccc    14700
aacagtgaag tagctgattg tcatcagcgc attgacggcg tccccggccg aaaaacccgc    14760
ctcgcagagg aagcgaagct gcgcgtcggc cgtttccatc tgcggtgcgc ccggtcgcgt    14820
```

```
gccggcatgg atgcgcgcgc catcgcggta ggcgagcagc gcctgcctga agctgcgggc    14880
attcccgatc agaaatgagc gccagtcgtc gtcggctctc ggcaccgaat gcgtatgatt    14940
ctccgccagc atggcttcgg ccagtgcgtc gagcagcgcc cgcttgttcc tgaagtgcca    15000
gtaaagcgcc ggctgctgaa cccccaaccg ttccgccagt ttgcgtgtcg tcagaccgtc    15060
tacgccgacc tcgttcaaca ggtccagggc ggcacggatc actgtattcg gctgcaactt    15120
tgtcatgctt gacactttat cactgataaa cataatatgt ccaccaactt atcagtgata    15180
aagaatccgc gcgttcaatc ggaccagcgg aggctggtcc ggaggccaga cgtgaaaccc    15240
aacatacccc tgatcgtaat tctgagcact gtcgcgctcg acgctgtcgg catcggcctg    15300
attatgccgg tgctgccggg cctcctgcgc gatctggttc actcgaacga cgtcaccgcc    15360
cactatggca ttctgctggc gctgtatgcg ttggtgcaat ttgcctgcgc acctgtgctg    15420
ggcgcgctgt cggatcgttt cgggcggcgg ccaatcttgc tcgtctcgct ggccggcgcc    15480
actgtcgact acgccatcat ggcgacagcg cctttccttt gggttctcta tcgggcgg    15540 atcgtggccg gcatcaccgg ggcgactggg gcggtagccg gcgcttatat tgccgatatc    15600
actgatggcg atgagcgcgc cggcacttc ggcttcatga gcgcctgttt cgggttcggg    15660
atggtcgcgg gacctgtgct cggtgggctg atgggcggtt tctcccccca cgctccgttc    15720
ttcgccgcgg cagccttgaa cggcctcaat ttcctgacgg gctgttttcct tttgccggag    15780 tcgcacaaag gcgaacgccg gccgttacgc cgggaggctc tcaacccgct cgcttcgttc    15840
cggtgggccc ggggcatgac cgtcgtcgcc gccctgatgg cggtcttctt catcatgcaa    15900
cttgtcggac aggtgccggc cgcgcttttgg gtcattttcg gcgaggatcg ctttcactgg    15960
gacgcgacca cgatcggcat ttcgcttgcc gcatttggca ttctgcattc actcgcccag    16020
gcaatgatca ccgccctgt agccgcccgg ctcggcgaaa gcgggcact catgctcgga    16080 atgattgccg acggcacagg ctacatcctg cttgccttcg cgacacgggg atggatggcg    16140
ttcccgatca tggtcctgct tgcttcgggt ggcatcggaa tgccggcgct gcaagcaatg    16200
ttgtccaggc aggtggatga ggaacgtcag gggcagctgc aaggctcact ggcggcgctc    16260
accagcctga cctcgatcgt cggacccctc ctcttcacgg cgatctatgc ggcttctata    16320
acaacgtgga acgggtgggc atggattgca ggcgctgccc tctacttgct ctgcctgccg    16380
gcgctgcgtc gcgggctttg gagcggcgca gggcaacgag ccgatcgctg atcgtggaaa    16440
cgataggcct atgccatgcg ggtcaaggcg acttccggca agctatacgc gccctaggag    16500
tgcggttgga acgttggccc agccagatac tcccgatcac gagcaggacg ccgatgattt    16560
gaagcgcact cagcgtctga tccaagaaca accatcctag caacacggcg gtccccgggc    16620
tgagaaagcc cagtaaggaa acaactgtag gttcgagtcg cgagatcccc cggaaccaaa    16680
ggaagtaggt taaacccgct ccgatcaggc cgagccacgc caggccgaga acattggttc    16740
ctgtaggcat cgggattggc ggatcaaaca ctaaagctac tggaacgagc agaagtcctc    16800
cggccgccag ttgccaggcg gtaaaggtga gcagaggcac gggaggttgc cacttgcggg    16860
tcagcacggt tccgaacgcc atggaaaccg ccccgccag gccgctgcg acgccgacag    16920 gatctagcgc tgcgtttggt gtcaacacca acagcgccac gccgcagtt ccgcaaatag    16980 cccccaggac cgccatcaat cgtatcgggc tacctagcag agcggcagag atgaacacga    17040
ccatcagcgg ctgcacagcg cctaccgtcg ccgcgacccc gccggcagg cggtagaccg    17100 aaataaacaa caagctccag aatagcgaaa tattaagtgc gccgaggatg aagatgcgca    17160
tccaccagat tcccgttgga atctgtcgga cgatcatcac gagcaataaa cccgccggca    17220
```

```
acgcccgcag cagcataccg gcgacccctc ggcctcgctg ttcgggctcc acgaaaacgc    17280
cggacagatg cgccttgtga gcgtccttgg ggccgtcctc ctgtttgaag accgacagcc    17340
caatgatctc gccgtcgatg taggcgccga atgccacggc atctcgcaac cgttcagcga    17400
acgcctccat gggcttttc  tcctcgtgct cgtaaacgga cccgaacatc tctggagctt    17460
tcttcagggc cgacaatcgg atctcgcgga aatcctgcac gtcggccgct ccaagccgtc    17520
gaatctgagc cttaatcaca attgtcaatt ttaatcctct gtttatcggc agttcgtaga    17580
gcgcgccgtg cgtcccgagc gatactgagc gaagcaagtg cgtcgagcag tgcccgcttg    17640
ttcctgaaat gccagtaaag cgctggctgc tgaaccccca gccggaactg accccacaag    17700
gccctagcgt ttgcaatgca ccaggtcatc attgacccag gcgtgttcca ccaggccgct    17760
gcctcgcaac tcttcgcagg cttcgccgac ctgctcgcgc cacttcttca cgcgggtgga    17820
atccgatccg cacatgaggc ggaaggtttc cagcttgagc gggtacggct cccggtgcga    17880
gctgaaatag tcgaacatcc gtcgggccgt cggcgacagc ttgcggtact tctcccatat    17940
gaatttcgtg tagtggtcgc cagcaaacag cacgacgatt tcctcgtcga tcaggacctg    18000
gcaacgggac gttttcttgc cacggtccag gacgcggaag cggtgcagca gcgacaccga    18060
ttccaggtgc ccaacgcggt cggacgtgaa gcccatcgcc gtcgcctgta ggcgcgacag    18120
gcattcctcg gccttcgtgt aataccggcc attgatcgac cagcccaggt cctggcaaag    18180
ctcgtagaac gtgaaggtga tcggctcgcc gatagggtg  cgcttcgcgt actccaacac    18240
ctgctgccac accagttcgt catcgtcggc ccgcagctcg acgccggtgt aggtgatctt    18300
cacgtccttg ttgacgtgga aaatgacctt gttttgcagc gcctcgcgcg ggattttctt    18360
gttgcgcgtg gtgaacaggg cagagcgggc cgtgtcgttt ggcatcgctc gcatcgtgtc    18420
cggccacggc gcaatatcga acaaggaaag ctgcatttcc ttgatctgct gcttcgtgtg    18480
tttcagcaac gcggcctgct tggcctcgct gacctgtttt gccaggtcct cgccggcggt    18540
ttttcgcttc ttggtcgtca tagttcctcg cgtgtcgatg gtcatcgact tcgccaaacc    18600
tgccgcctcc tgttcgagac gacgcgaacg ctccacggcg gccgatggcg cgggcagggc    18660 aggggggagcc agttgcacgc tgtcgcgctc gatcttggcc gtagcttgct ggaccatcga    18720
gccgacggac tggaaggttt cgcggggcgc acgcatgacg gtgcggcttg cgatggtttc    18780
ggcatcctcg gcggaaaacc ccgcgtcgat cagttcttgc ctgtatgcct tccggtcaaa    18840
cgtccgattc attcaccctc cttgcgggat tgccccgact cacgccgggg caatgtgccc    18900
ttattcctga tttgacccgc ctggtgcctt ggtgtccaga taatccacct tatcggcaat    18960
gaagtcggtc ccgtagaccg tctggccgtc cttctcgtac ttggtattcc gaatcttgcc    19020
ctgcacgaat accagcgacc ccttgcccaa atacttgccg tgggcctcgg cctgagagcc    19080
aaaacacttg atgcggaaga agtcggtgcg ctcctgcttg tcgccggcat cgttgcgcca    19140
ctcttcatta accgctatat cgaaaattgc ttgcggcttg ttagaattgc catgacgtac    19200
ctcggtgtca cgggtaagat taccgataaa ctggaactga ttatggctca tatcgaaagt    19260
ctccttgaga aaggagactc tagtttagct aaacattggt tccgctgtca agaactttag    19320
cggctaaaat tttgcgggcc gcgaccaaag gtgcgagggg cggcttccgc tgtgtacaac    19380
cagatatttt tcaccaacat ccttcgtctg ctcgatgagc ggggcatgac gaaacatgag    19440
ctgtcggaga gggcaggggt ttcaatttcg tttttatcag acttaaccaa cggtaaggcc    19500 aaccccctcgt tgaaggtgat ggaggccatt gccgacgccc tggaaactcc cctacctctt    19560
```

```
ctcctggagt ccaccgacct tgaccgcgag gcactcgcgg agattgcggg tcatcctttc    19620
aagagcagcg tgccgcccgg atacgaacgc atcagtgtgg ttttgccgtc acataaggcg    19680
tttatcgtaa agaaatgggg cgacgacacc cgaaaaaagc tgcgtggaag gctctgacgc    19740
caagggttag ggcttgcact tccttcttta gccgctaaaa cggccccttc tctgcgggcc    19800
gtcggctcgc gcatcatatc gacatcctca acggaagccg tgccgcgaat ggcatcgggc    19860
gggtgcgctt tgacagttgt tttctatcag aacccctacg tcgtgcggtt cgattagctg    19920
tttgtcttgc aggctaaaca ctttcggtat atcgtttgcc tgtgcgataa tgttgctaat    19980
gatttgttgc gtaggggtta ctgaaaagtg agcgggaaag aagagtttca gaccatcaag    20040
gagcgggcca agcgcaagct ggaacgcgac atgggtgcgg acctgttggc cgcgctcaac    20100
gacccgaaaa ccgttgaagt catgctcaac gcggacggca aggtgtggca cgaacgcctt    20160
ggcgagccga tgcggtacat ctgcgacatg cggcccagcc agtcgcaggc gattatagaa    20220
acggtggccg gattcacggg caaagaggtc acgcggcatt cgcccatcct ggaaggcgag    20280
ttccccttgg atgcagccg ctttgccggc caattgccgc cggtcgtggc cgcgccaacc    20340
tttgcgatcc gcaagcgcgc ggtcgccatc ttcacgctgg aacagtacgt cgaggcgggc    20400
atcatgaccc gcgagcaata cgaggtcatt aaaagcgccg tcgcggcgca tcgaaacatc    20460
ctcgtcattg gcggtactgg ctcgggcaag accacgctcg tcaacgcgat catcaatgaa    20520
atggtcgcct tcaacccgtc tgagcgcgtc gtcatcatcg aggacaccgg cgaaatccag    20580
tgcgccgcag agaacgccgt ccaataccac accagcatcg acgtctcgat gacgctgctg    20640
ctcaagacaa cgctgcgtat gcgccccgac cgcatcctgg tcggtgaggt acgtggcccc    20700
gaagcccttg atctgttgat ggcctggaac accgggcatg aaggaggtgc cgccaccctg    20760
cacgcaaaca accccaaagc gggcctgagc cggctcgcca tgcttatcag catgcacccg    20820
gattcaccga aacccattga ccgctgatt ggcgaggcgg ttcatgtggt cgtccatatc    20880
gccaggaccc ctagcggccg tcgagtgcaa gaaattctcg aagttcttgg ttacgagaac    20940
ggccagtaca tcaccaaaac cctgtaagga gtatttccaa tgacaacggc tgttccgttc    21000
cgtctgacca tgaatcgcgg catttttgttc taccttgccg tgttcttcgt tctcgctctc    21060
gcgttatccg cgcatccggc gatggcctcg gaaggcaccg gcggcagctt gccatatgag    21120
agctggctga cgaacctgcg caactccgta accggcccgg tggccttcgc gctgtccatc    21180
atcggcatcg tcgtcgccgg cggcgtgctg atcttcggcg gcgaactcaa cgccttcttc    21240
cgaaccctga tcttcctggt tctggtgatg gcgctgctgg tcggcgcgca gaacgtgatg    21300
agcaccttct tcggtcgtgg tgccgaaatc gcggccctcg gcaacggggc gctgcaccag    21360
gtgcaagtcg cggcggcgga tgccgtgcgt gcggtagcgg ctggacggct cgcctaatca    21420
tggctctgcg cacgatcccc atccgtcgcg caggcaaccg agaaaacctg ttcatgggtg    21480
gtgatcgtga actggtgatg ttctcggggcc tgatggcgtt tgcgctgatt ttcagcgccc    21540
aagagctgcg ggccaccgtg gtcggtctga tcctgtggtt cggggcgctc tatgcgttcc    21600
gaatcatggc gaaggccgat ccgaagatgc ggttcgtgta cctgcgtcac cgccggtaca    21660
agccgtatta cccggcccgc tcgacccccgt tccgcgagaa caccaatagc caagggaagc    21720
aataccgatg atccaagcaa ttgcgattgc aatcgcgggc ctcggcgcgc ttctgttgtt    21780
catcctcttt gcccgcatcc gcgcggtcga tgccgaactg aaactgaaaa agcatcgttc    21840
caaggacgcc ggcctggccg atctgctcaa ctacgccgct gtcgtcgatg acggcgtaat    21900
cgtgggcaag aacggcagct ttatggctgc ctggctgtac aagggcgatg acaacgcaag    21960
```

```
cagcaccgac cagcagcgcg aagtagtgtc cgcccgcatc aaccaggccc tcgcgggcct   22020
gggaagtggg tggatgatcc atgtggacgc cgtgcggcgt cctgctccga actacgcgga   22080
gcggggcctg tcggcgttcc ctgaccgtct gacggcagcg attgaagaag agcgctcggt   22140
cttgccttgc tcgtcggtga tgtacttcac cagctccgcg aagtcgctct tcttgatgga   22200
gcgcatgggg acgtgcttgg caatcacgcg caccccccgg ccgttttagc ggctaaaaaa   22260
gtcatggctc tgccctcggg cggaccacgc ccatcatgac cttgccaagc tcgtcctgct   22320
tctcttcgat cttcgccagc agggcgagga tcgtggcatc accgaaccgc gccgtgcgcg   22380
ggtcgtcggt gagccagagt ttcagcaggc cgcccaggcg gcccaggtcg ccattgatgc   22440
gggccagctc gcggacgtgc tcatagtcca cgacgcccgt gattttgtag ccctggccga   22500
cggccagcag gtaggccgac aggctcatgc cggccgccgc cgccttttcc tcaatcgctc   22560
ttcgttcgtc tggaaggcag tacaccttga taggtgggct gcccttcctg gttggcttgg   22620
tttcatcagc catccgcttg ccctcatctg ttacgccggc ggtagccggc cagcctcgca   22680
gagcaggatt cccgttgagc accgccaggt gcgaataagg gacagtgaag aaggaacacc   22740
cgctcgcggg tgggcctact tcacctatcc tgcccggctg acgccgttgg atacaccaag   22800
gaaagtctac acgaacccct tggcaaaatc ctgtatatcg tgcgaaaaag gatggatata   22860
ccgaaaaaat cgctataatg accccgaagc agggttatgc agcggaaaag cgctgcttcc   22920
ctgctgtttt gtggaatatc taccgactgg aaacaggcaa atgcaggaaa ttactgaact   22980
gaggggacag gcgagagacg atgccaaaga gctacaccga cgagctggcc gagtgggttg   23040
aatcccgcgc ggccaagaag cgccggcgtg atgaggctgc ggttgcgttc ctggcggtga   23100
gggcggatgt cgaggcggcg ttagcgtccg gctatgcgct cgtcaccatt tgggagcaca   23160
tgcgggaaac ggggaaggtc aagttctcct acgagacgtt ccgctcgcac gccaggcggc   23220
acatcaaggc caagcccgcc gatgtgcccg caccgcaggc caaggctgcg gaacccgcgc   23280
cggcacccaa gacgccggag ccacggcggc cgaagcaggg gggcaaggct gaaaagccgg   23340
cccccgctgc ggccccgacc ggcttcacct tcaacccaac accggacaaa aaggatctac   23400
tgtaatggcg aaaattcaca tggttttgca gggcaagggc ggggtcggca agtcggccat   23460
cgccgcgatc attgcgcagt acaagatgga caaggggcag acaccccttgt gcatcgacac   23520
cgaccccggtg aacgcgacgt tcgagggcta caaggccctg aacgtccgcc ggctgaacat   23580
catggccggc gacgaaatta actcgcgcaa cttcgacacc ctggtcgagc tgattgcgcc   23640
gaccaaggat gacgtggtga tcgacaacgg tgccagctcg ttcgtgcctc tgtcgcatta   23700
cctcatcagc aaccaggtgc cggctctgct gcaagaaatg gggcatgagc tggtcatcca   23760
taccgtcgtc accggcggcc aggctctcct ggacacggtg agcggcttcg cccagctcgc   23820
cagccagttc ccggccgaag cgcttttcgt ggtctggctg aacccgtatt gggggcctat   23880
cgagcatgag gcaagagct ttgagcagat gaaggcgtac acggccaaca aggcccgcgt   23940
gtcgtccatc atccagattc cggccctcaa ggaagaaacc tacggccgcg atttcagcga   24000
catgctgcaa gagcggctga cgttcgacca ggcgctggcc gatgaatcgc tcacgatcat   24060
gacgcggcaa cgcctcaaga tcgtgcgcg cggcctgttt gaacagctcg acgcggcggc   24120
cgtgctatga cgaccagat tgaagagctg atccgggaga ttgcggccaa gcacggcatc   24180
gccgtcggcc gcgacgaccc ggtgctgatc ctgcatacca tcaacgcccg gctcatggcc   24240
gacagtgcgg ccaagcaaga ggaaatcctt gccgcgttca aggaagagct ggaagggatc   24300
```

```
gcccatcgtt ggggcgagga cgccaaggcc aaagcggagc ggatgctgaa cgcggccctg    24360
gcggccagca aggacgcaat ggcgaaggta atgaaggaca cgccgcgca ggcggccgaa     24420 gcgatccgca gggaaatcga cgacggcctt ggccgccagc tcgcggccaa ggtcgcggac    24480
gcgcggcgcg tggcgatgat gaacatgatc gccggcggca tggtgttgtt cgcggccgcc    24540
ctggtggtgt gggcctcgtt atgaatcgca gaggcgcaga tgaaaaagcc cggcgttgcc    24600
gggctttgtt tttgcgttag ctgggcttgt ttgacaggcc caagctctga ctgcgcccgc    24660
gctcgcgctc ctgggcctgt tcttctcct gctcctgctt gcgcatcagg gcctggtgcc     24720
gtcgggctgc ttcacgcatc gaatcccagt cgccggccag ctcgggatgc tccgcgcgca    24780
tcttgcgcgt cgccagttcc tcgatcttgg gcgcgtgaat gcccatgcct tccttgattt    24840
cgcgcaccat gtccagccgc gtgtgcaggg tctgcaagcg ggcttgctgt gggcctgct     24900 gctgctgcca ggcggccttt gtacgcggca gggacagcaa gccgggggca ttggactgta    24960
gctgctgcaa acgcgcctgc tgacggtcta cgagctgttc taggcggtcc tcgatgcgct    25020
ccacctggtc atgctttgcc tgcacgtaga gcgcaagggt ctgctggtag gtctgctcga    25080
tgggcgcgga ttctaagagg gcctgctgtt ccgtctcggc ctcctgggcc gcctgtagca    25140
aatcctcgcc gctgttgccg ctggactgct ttactgccgg ggactgctgt tgccctgctc    25200
gcgccgtcgt cgcagttcgg cttgccccca ctcgattgac tgcttcattt cgagccgcag    25260
cgatgcgatc tcggattgcg tcaacggacg gggcagcgcg gaggtgtccg gcttctcctt    25320
gggtgagtcg gtcgatgcca tagccaaagg tttccttcca aaatgcgtcc attgctggac    25380
cgtgtttctc attgatgccc gcaagcatct tcggcttgac cgccaggtca agcgcgcctt    25440
catgggcggt catgacggac gccgccatga ccttgccgcc gttgttctcg atgtagccgc    25500
gtaatgaggc aatggtgccg cccatcgtca gcgtgtcatc gacaacgatg tacttctggc    25560
cggggatcac ctccccctcg aaagtcgggt tgaacgccag gcgatgatct gaaccggctc    25620
cggttcgggc gaccttctcc cgctgcacaa tgtccgtttc gacctcaagg ccaaggcggt    25680
cggccagaac gaccgccatc atggccggaa tcttgttgtt ccccgccgcc tcgacggcga    25740
ggactggaac gatgcggggc ttgtcgtcgc cgatcagcgt cttgagctgg caacagtgt     25800 cgtccgaaat caggcgctcg accaaattaa gcgccgcttc cgcgtcgccc tgcttcgcag    25860
cctggtattc aggctcgttg gtcaaagaac caaggtcgcc gttgcgaacc accttcggga    25920
agtctcccca cggtgcgcgc tcggctctgc tgtagctgct caagacgcct ccctttttag    25980
ccgctaaaac tctaacgagt gcgcccgcga ctcaacttga cgctttcggc acttacctgt    26040
gccttgccac ttgcgtcata ggtgatgctt ttcgcactcc cgatttcagg tactttatcg    26100
aaatctgacc gggcgtgcat tacaaagttc ttccccacct gttggtaaat gctgccgcta    26160
tctgcgtgga cgatgctgcc gtcgtggcgc tgcgacttat cggcctttttg ggccatatag    26220 atgttgtaaa tgccaggttt cagggccccg gctttatcta ccttctggtt cgtccatgcg    26280
ccttggttct cggtctggac aattctttgc ccattcatga ccaggaggcg gtgtttcatt    26340
gggtgactcc tgacggttgc ctctggtgtt aaacgtgtcc tggtcgcttg ccggctaaaa    26400
aaaagccgac ctcggcagtt cgaggccggc tttcctaga gccgggcgcg tcaaggttgt     26460
tccatctatt ttagtgaact gcgttcgatt tatcagttac tttcctcccg ctttgtgttt    26520
cctcccactc gtttccgcgt ctagccgacc cctcaacata gcggcctctt cttgggctgc    26580 cttttgcctct tgccgcgctt cgtcacgctc ggcttgcacc gtcgtaaagc gctcggcctg    26640
cctggccgcc tcttgcgccg ccaacttcct ttgctcctgg tgggcctcgg cgtcggcctg    26700
```

```
cgccttcgct ttcaccgctg ccaactccgt gcgcaaactc tccgcttcgc gcctggtggc   26760
gtcgcgctcg ccgcgaagcg cctgcatttc ctggttggcc gcgtccaggg tcttgcggct   26820
ctcttctttg aatgcgcggg cgtcctggtg agcgtagtcc agctcggcgc gcagctcctg   26880
cgctcgacgc tccacctcgt cggcccgctg cgtcgccagc gcggcccgct gctcggctcc   26940
tgccagggcg gtgcgtgctt cggccagggc ttgccgctgg cgtgcggcca gctcggccgc   27000
ctcggcggcc tgctgctcta gcaatgtaac gcgcgcctgg gcttcttcca gctcgcgggc   27060
ctgcgcctcg aaggcgtcgg ccagctcccc gcgcacggct tccaactcgt tgcgctcacg   27120
atcccagccg gcttgcgctg cctgcaacga ttcattggca agggcctggg cggcttgcca   27180
gagggcggcc acggcctggt tgccggcctg ctgcaccgcg tccggcacct ggactgccag   27240
cggggcggcc tgcgccgtgc gctggcgtcg ccattcgcgc atgccggcgc tggcgtcgtt   27300
catgttgacg cgggcggcct tacgcactgc atccacggtc gggaagttct cccggtcgcc   27360
ttgctcgaac agctcgtccg cagccgcaaa aatgcggtcg cgcgtctctt tgttcagttc   27420
catgttggct ccggtaattg gtaagaataa taatactctt acctacctta tcagcgcaag   27480
agtttagctg aacagttctc gacttaacgg caggttttt agcggctgaa gggcaggcaa   27540
aaaaagcccc gcacggtcgg cgggggcaaa gggtcagcgg aagggggatt agcgggcgtc   27600
gggcttcttc atgcgtcggg gccgcgcttc ttgggatgga gcacgacgaa gcgcgcacgc   27660
gcatcgtcct cggccctatc ggcccgcgtc gcggtcagga acttgtcgcg cgctaggtcc   27720
tccctggtgg gcaccagggg catgaactcg gcctgctcga tgtaggtcca ctccatgacc   27780
gcatcgcagt cgaggccgcg ttccttcacc gtctcttgca ggtcgcggta cgcccgctcg   27840
ttgagcggct ggtaacgggc caattggtcg taaatggctg tcggccatga gcggcctttc   27900
ctgttgagcc agcagccgac gacgaagccg gcaatgcagg cccctggcac aaccaggccg   27960
acgccggggg caggggatgg cagcagctcg ccaaccagga accccgccgc gatgatgccg   28020
atgccggtca accagcccctt gaaactatcc ggccccgaaa caccccctgcg cattgcctgg   28080 atgctgcgcc ggatagcttg caacatcagg agccgtttct tttgttcgtc agtcatggtc   28140
cgccctcacc agttgttcgt atcggtgtcg gacgaactga aatcgcaaga gctgccggta   28200
tcggtccagc cgctgtccgt gtcgctgctg ccgaagcacg gcgaggggtc cgcgaacgcc   28260
gcagacggcg tatccggccg cagcgcatcg cccagcatgg ccccggtcag cgagccgccg   28320
gccaggtagc ccagcatggt gctgttggtc gccccggcca ccagggccga cgtgacgaaa   28380
tcgccgtcat tccctctgga ttgttcgctg ctcggcgggg cagtgcgccg cgccggcggc   28440
gtcgtggatg gctcgggttg gctggcctgc gacggccggc gaaaggtgcg cagcagctcg   28500
ttatcgaccg gctgcggcgt cggggccgcc gccttgcgct gcggtcggtg ttccttcttc   28560
ggctcgcgca gcttgaacag catgatcgcg gaaaccagca gcaacgccgc gcctacgcct   28620
cccgcgatgt agaacagcat cggattcatt cttcggtcct ccttgtagcg gaaccgttgt   28680
ctgtgcggcg cgggtggccc gcgccgctgt ctttgggat cagccctcga tgagcgcgac   28740
cagtttcacg tcggcaaggt tcgcctcgaa ctcctggccg tcgtcctcgt acttcaacca   28800
ggcatagcct tccgccggcg gccgacggtt gaggataagg cgggcagggc gctcgtcgtg   28860
ctcgacctgg acgatggcct ttttcagctt gtccgggtcc ggctccttcg cgcccttttc   28920
cttggcgtcc ttaccgtcct ggtcgccgtc ctcgccgtcc tggccgtcgc cggcctccgg   28980
gtcacgctcg gcatcagtct ggccgttgaa ggcatcgacg gtgttgggat cgcggccctt   29040
```

```
ctcgtccagg aactcgcgca gcagcttgac cgtgccgcgc gtgatttcct gggtgtcgtc    29100
gtcaagccac gcctcgactt cctccgggcg cttcttgaag gccgtcacca gctcgttcac    29160
cacggtcacg tcgcgcacgc ggccggtgtt aacgcatcg gcgatcttct ccggcaggtc    29220
cagcagcgtg acgtgctggg tgatgaacgc cggcgacttg ccgatttcct tggcgatatc    29280
gcctttcttc ttgcccttcg ccagctcgcg gccaatgaag tcggcaattt cgcgcggggt    29340
cagctcgttg cgttgcaggt tctcgataac ctggtcggct tcgttgtagt cgttgtcgat    29400
gaacgccggg atggacttct tgccggccca cttcgagcca cggtagcggc gggcgccgtg    29460
attgatgata tagcggcccg gctgctcctg gttctcgcgc accgaaatgg gtgacttcac    29520
cccgcgctct ttgatcgtgg caccgatttc cgcgatgctc tccggggaaa agccggggtt    29580
gtcggccgtc cgcggctgat gcggatcttc gtcgatcagg tccaggtcca gctcgatagg    29640
gccggaaccg ccctgagacg ccgcaggagc gtccaggagg ctcgacaggt cgccgatgct    29700
atccaacccc aggccggacg gctgcgccgc gcctgcggct tcctgagcgg ccgcagcggt    29760
gtttttcttg gtggtcttgg cttgagccgc agtcattggg aaatctccat cttcgtgaac    29820
acgtaatcag ccagggcgcg aacctctttc gatgccttgc gcgcggccgt tttcttgatc    29880
ttccagaccg gcacaccgga tgcgagggca tcggcgatgc tgctgcgcag ccaacggtg    29940 gccggaatca tcatcttggg gtacgcggcc agcagctcgg cttggtggcg cgcgtggcgc    30000
ggattccgcg catcgacctt gctgggcacc atgccaagga attgcagctt ggcgttcttc    30060
tggcgcacgt tcgcaatggt cgtgaccatc ttcttgatgc cctggatgct gtacgcctca    30120
agctcgatgg gggacagcac atagtcggcc gcgaagaggg cggccgccag gccgacgcca    30180
agggtcgggg ccgtgtcgat caggcacacg tcgaagcctt ggttcgccag ggccttgatg    30240
ttcgccccga acagctcgcg ggcgtcgtcc agcgacagcc gttcggcgtt cgccagtacc    30300
gggttggact cgatgagggc gaggcgcgcg gcctggccgt cgccggctgc gggtgcggtt    30360
tcggtccagc cgccggcagg gacagcgccg aacagcttgc ttgcatgcag gccggtagca    30420
aagtccttga gcgtgtagga cgcattgccc tggggtcca ggtcgatcac ggcaacccgc    30480
aagccgcgct cgaaaaagtc gaaggcaaga tgcacaaggg tcgaagtctt gccgacgccg    30540
cctttctggt tggccgtgac caaagttttc atcgtttggt ttcctgtttt tcttggcgt    30600 ccgcttccca cttccggacg atgtacgcct gatgttccgg cagaaccgcc gttaccgcg    30660 cgtacccctc gggcaagttc ttgtcctcga acgcggccca cacgcgatgc accgcttgcg    30720
acactgcgcc cctggtcagt cccagcgacg ttgcgaacgt cgcctgtggc ttcccatcga    30780
ctaagacgcc ccgcgctatc tcgatggtct gctgccccac ttccagcccc tggatcgcct    30840
cctggaactg gctttcggta agccgttct tcatggataa cacccataat ttgctccgcg    30900
ccttggttga acatagcggt gacagccgcc agcacatgag agaagtttag ctaaacattt    30960
ctcgcacgtc aacacccttta gccgctaaaa ctcgtccttg gcgtaacaaa acaaaagccc    31020
ggaaaccggg ctttcgtctc ttgccgctta tggctctgca cccggctcca tcaccaacag    31080
gtcgcgcacg cgcttcactc ggttgcggat cgacactgcc agcccaacaa agccggttgc    31140
cgccgccgcc aggatcgcgc cgatgatgcc ggccacaccg gccatcgccc accaggtcgc    31200
cgccttccgg ttccattcct gctggtactg cttcgcaatg ctggacctcg gctcaccata    31260
ggctgaccgc tcgatggcgt atgccgcttc tccccttggc gtaaacccca gcgccgcagg    31320
cggcattgcc atgctgcccg ccgctttccc gaccacgacg cgcgcaccag gcttgcggtc    31380
cagaccttcg gccacggcga gctgcgcaag gacataatca gccgccgact tggctccacg    31440
```

```
cgcctcgatc agctcttgca ctcgcgcgaa atccttggcc tccacggccg ccatgaatcg   31500
cgcacgcggc gaaggctccg cagggccggc gtcgtgatcg ccgccgagaa tgcccttcac   31560
caagttcgac gacacgaaaa tcatgctgac ggctatcacc atcatgcaga cggatcgcac   31620
gaacccgctg aattgaacac gagcacggca cccgcgacca ctatgccaag aatgcccaag   31680
gtaaaaattg ccggccccgc catgaagtcc gtgaatgccc cgacggccga agtgaagggc   31740
aggccgccac ccaggccgcc gccctcactg cccggcacct ggtcgctgaa tgtcgatgcc   31800
agcacctgcg gcacgtcaat gcttccgggc gtcgcgctcg ggctgatcgc ccatcccgtt   31860
actgccccga tcccggcaat ggcaaggact gccagcgctg ccattttggg ggtgaggccg   31920
ttcgcggccg aggggcgcag cccctggggg gatgggaggc ccgcgttagc gggccgggag   31980
ggttcgagaa gggggggcac ccccttcgg cgtgcgcggt cacgcgcaca gggcgcagcc   32040
ctggttaaaa acaaggttta taaatattgg tttaaaagca ggttaaaaga caggttagcg   32100
gtggccgaaa acgggcgga aacccttgca aatgctggat tttctgcctg tggacagccc   32160
ctcaaatgtc aataggtgcg cccctcatct gtcagcactc tgcccctcaa gtgtcaagga   32220
tcgcgcccct catctgtcag tagtcgcgcc cctcaagtgt caataccgca gggcacttat   32280
ccccaggctt gtccacatca tctgtgggaa actcgcgtaa aatcaggcgt tttcgccgat   32340
ttgcgaggct ggccagctcc acgtcgccgg ccgaaatcga gcctgcccct catctgtcaa   32400
cgccgcgccg ggtgagtcgg cccctcaagt gtcaacgtcc gcccctcatc tgtcagtgag   32460
ggccaagttt tccgcgaggt atccacaacg ccggcggccg cggtgtctcg cacacggctt   32520
cgacggcgtt tctggcgcgt ttgcagggcc atagacggcc gccagcccag cggcgagggc   32580
aaccagcccg gtgagcgtcg gaaaggcgct ggaagcccg tagcgacgcg gagaggggcg   32640
agacaagcca agggcgcagg ctcgatgcgc agcacgacat agccggttct cgcaaggacg   32700
agaatttccc tgcggtgccc ctcaagtgtc aatgaaagtt tccaacgcga gccattcgcg   32760
agagccttga gtccacgcta gatgagagct ttgttgtagg tggaccagtt ggtgattttg   32820
aacttttgct ttgccacgga acggtctgcg ttgtcgggaa gatgcgtgat ctgatccttc   32880
aactcagcaa aagttcgatt tattcaacaa agccacgttg tgtctcaaaa tctctgatgt   32940
tacattgcac aagataaaaa tatatcatca tgaacaataa aactgtctgc ttacataaac   33000
agtaatacaa ggggtgttat gagccatatt caacgggaaa cgtcttgctc gactctagag   33060
ctcgttcctc gaggcctcga ggcctcgagg aacggtacct gcgggaaagc ttacaataat   33120
gtgtgttgtt aagtcttgtt gcctgtcatc gtctgactga ctttcgtcat aaatcccggc   33180
ctccgtaacc cagctttggg caagctcacg gatttgatcc ggcggaacgg gaatatcgag   33240
atgccgggct gaacgctgca gttccagctt tccctttcgg gacaggtact ccagctgatt   33300
gattatctgc tgaagggtct tggttccacc tcctggcaca atgcgaatga ttacttgagc   33360
gcgatcgggc atccaatttt ctcccgtcag gtgcgtggtc aagtgctaca aggcacctt    33420 cagtaacgag cgaccgtcga tccgtcgccg ggatacggac aaaatggagc gcagtagtcc   33480
atcgagggcg gcgaaagcct cgccaaaagc aatacgttca tctcgcacag cctccagatc   33540
cgatcgaggg tcttcggcgt aggcagatag aagcatggat acattgcttg agagtattcc   33600
gatggactga agtatggctt ccatcttttc tcgtgtgtct gcatctattt cgagaaagcc   33660
cccgatgcgg cgcaccgcaa cgcgaattgc catactatcc gaaagtccca gcaggcgcgc   33720
ttgataggaa aaggtttcat actcggccga tcgcagacgg gcactcacga ccttgaaccc   33780
```

```
ttcaactttc agggatcgat gctggttgat ggtagtctca ctcgacgtgg ctctggtgtg   33840
ttttgacata gcttcctcca aagaaagcgg aaggtctgga tactccagca cgaaatgtgc   33900
ccgggtagac ggatggaagt ctagccctgc tcaatatgaa atcaacagta catttacagt   33960
caatactgaa tatacttgct acatttgcaa ttgtcttata acgaatgtga aataaaaata   34020
gtgtaacaac gcttttactc atcgataatc acaaaaacat ttatacgaac aaaaatacaa   34080
atgcactccg gtttcacagg ataggcggga tcagaatatg caacttttga cgttttgttc   34140
tttcaaaggg ggtgctggca aaaccaccgc actcatgggc ctttgcgctg ctttggcaaa   34200
tgacggtaaa cgagtggccc tctttgatgc cgacgaaaac cggcctctga cgcgatggag   34260
agaaaacgcc ttacaaagca gtactgggat cctcgctgtg aagtctattc cgccgacgaa   34320 atgcccttc ttgaagcagc ctatgaaaat gccgagctcg aaggatttga ttatgcgttg   34380
gccgatacgc gtggcggctc gagcgagctc aacaacacaa tcatcgctag ctcaaacctg   34440
cttctgatcc ccaccatgct aacgccgctc gacatcgatg aggcactatc tacctaccgc   34500
tacgtcatcg agctgctgtt gagtgaaaat ttggcaattc ctacagctgt tttgcgccaa   34560
cgcgtcccgg tcggccgatt gacaacatcg caacgcagga tgtcagagac gctagagagc   34620
cttccagttg taccgtctcc catgcatgaa agagatgcat ttgccgcgat gaagaacgc    34680 ggcatgttgc atcttacatt actaaacacg gaactgatc cgacgatgcg cctcatagag    34740
aggaatcttc ggattgcgat ggaggaagtc gtggtcattt cgaaactgat cagcaaaatc    34800
ttggaggctt gaagatggca attcgcaagc ccgcattgtc ggtcggcgaa gcacggcggc    34860
ttgctggtgc tcgacccgag atccaccatc ccaacccgac acttgttccc cagaagctgg    34920
acctccagca cttgcctgaa aaagccgacg agaaagacca gcaacgtgag cctctcgtcg    34980
ccgatcacat ttacagtccc gatcgacaac ttaagctaac tgtggatgcc cttagtccac    35040
ctccgtcccc gaaaaagctc caggttttc tttcagcgcg accgcccgcg cctcaagtgt     35100
cgaaaacata tgacaacctc gttcggcaat acagtccctc gaagtcgcta caaatgattt    35160
taaggcgcgc gttggacgat ttcgaaagca tgctggcaga tggatcattt cgcgtggccc    35220
cgaaaagtta tccgatccct tcaactacag aaaaatccgt tctcgttcag acctcacgca    35280
tgttcccggt tgcgttgctc gaggtcgctc gaagtcattt tgatccgttg gggttggaga    35340
ccgctcgagc tttcggccac aagctggcta ccgccgcgct cgcgtcattc tttgctggag    35400
agaagccatc gagcaattgg tgaagaggga cctatcggaa cccctcacca aatattgagt    35460
gtaggtttga ggccgctggc cgcgtcctca gtcaccttt gagccagata attaagagcc      35520
aaatgcaatt ggctcaggct gccatcgtcc ccccgtgcga aacctgcacg tccgcgtcaa    35580
agaaataacc ggcacctctt gctgttttta tcagttgagg gcttgacgga tccgcctcaa    35640
gtttgcggcg cagccgcaaa atgagaacat ctatactcct gtcgtaaacc tcctcgtcgc    35700
gtactcgact ggcaatgaga agttgctcgc gcgatagaac gtcgcggggt ttctctaaaa    35760
acgcgaggag aagattgaac tcacctgccg taagtttcac ctcaccgcca gcttcggaca    35820
tcaagcgacg ttgcctgaga ttaagtgtcc agtcagtaaa acaaaaagac cgtcggtctt     35880
tggagcggac aacgttgggg cgcacgcgca aggcaacccg aatgcgtgca agaaactctc    35940
tcgtactaaa cggcttagcg ataaaatcac ttgctcctag ctcgagtgca caactttat     36000 ccgtctcctc aaggcggtcg ccactgataa ttatgattgg aatatcagac tttgccgcca    36060
gatttcgaac gatctcaagc ccatcttcac gacctaaatt tagatcaaca accacgacat    36120
cgaccgtcgc ggaagagagt actctagtga actgggtgct gtcggctacc gcggtcactt     36180
```

```
tgaaggcgtg gatcgtaagg tattcgataa taagatgccg catagcgaca tcgtcatcga    36240
taagaagaac gtgtttcaac ggctcacctt tcaatctaaa atctgaaccc ttgttcacag    36300
cgcttgagaa attttcacgt gaaggatgta caatcatctc cagctaaatg ggcagttcgt    36360
cagaattgcg gctgaccgcg gatgacgaaa atgcgaacca agtatttcaa ttttatgaca    36420
aaagttctca atcgttgtta caagtgaaac gcttcgaggt tacagctact attgattaag    36480
gagatcgcct atggtctcgc cccggcgtcg tgcgtccgcc gcgagccaga tctcgcctac    36540
ttcataaacg tcctcatagg cacggaatgg aatgatgaca tcgatcgccg tagagagcat    36600
gtcaatcagt gtgcgatctt ccaagctagc accttgggcg ctactttga caagggaaaa    36660 cagtttcttg aatccttgga ttggattcgc gccgtgtatt gttgaaatcg atcccggatg    36720
tcccgagacg acttcactca gataagccca tgctgcatcg tcgcgcatct cgccaagcaa    36780
tatccggtcc ggccgcatac gcagacttgc ttggagcaag tgctcggcgc tcacagcacc    36840
cagcccagca ccgttcttgg agtagagtag tctaacatga ttatcgtgtg gaatgacgag    36900
ttcgagcgta tcttctatgg tgattagcct ttcctggggg gggatggcgc tgatcaaggt    36960
cttgctcatt gttgtcttgc cgcttccggt agggccacat agcaacatcg tcagtcggct    37020
gacgacgcat gcgtgcagaa acgcttccaa atccccgttg tcaaaatgct gaaggatagc    37080
ttcatcatcc tgattttggc gtttccttcg tgtctgccac tggttccacc tcgaagcatc    37140
ataacgggag gagacttctt taagaccaga aacacgcgag cttggccgtc gaatggtcaa    37200
gctgacggtg cccgagggaa cggtcggcgg cagacagatt tgtagtcgtt caccaccagg    37260
aagttcagtg gcgcagaggg ggttacgtgg tccgacatcc tgctttctca gcgcgcccgc    37320
taaaatagcg atatcttcaa gatcatcata agagacgggc aaaggcatct tggtaaaaat    37380
gccggcttgg cgcacaaatg cctctccagg tcgattgatc gcaatttctt cagtcttcgg    37440
gtcatcgagc cattccaaaa tcggcttcag aagaaagcgt agttgcggat ccacttccat    37500
ttacaatgta tcctatctct aagcggaaat ttgaattcat taagagcggc ggttcctccc    37560
ccgcgtggcg ccgccagtca ggcggagctg gtaaacacca aagaaatcga ggtcccgtgc    37620
tacgaaaatg gaaacggtgt caccctgatt cttcttcagg gttggcggta tgttgatggt    37680
tgccttaagg gctgtctcag ttgtctgctc accgttattt tgaaagctgt tgaagctcat    37740
cccgccaccc gagctgccgg cgtaggtgct agctgcctgg aaggcgcctt gaacaacact    37800
caagagcata gctccgctaa aacgctgcca gaagtggctg tcgaccgagc ccggcaatcc    37860
tgagcgaccg agttcgtccg cgcttggcga tgttaacgag atcatcgcat ggtcaggtgt    37920
ctcggcgcga tcccacaaca caaaaacgcg cccatctccc tgttgcaagc cacgctgtat    37980
ttcgccaaca acgtggtgc cacgatcaag aagcacgata ttgttcgttg ttccacgaat    38040
atcctgaggc aagacacact ttacatagcc tgccaaattt gtgtcgattg cggtttgcaa    38100
gatgcacgga attattgtcc cttgcgttac cataaaatcg gggtgcggca agagcgtggc    38160
gctgctgggc tgcagctcgg tgggtttcat acgtatcgac aaatcgttct cgccggacac    38220
ttcgccattc ggcaaggagt tgtcgtcacg cttgccttct tgtcttcggc ccgtgtcgcc    38280
ctgaatggcg cgtttgctga ccccttgatc gccgctgcta tatgcaaaaa tcggtgtttc    38340
ttccggccgt ggctcatgcc gctccggttc gcccctcggc ggtagaggag cagcaggctg    38400
aacagcctct tgaaccgctg gaggatccgg cggcacctca atcggagctg gatgaaatgg    38460
cttggtgttt gttgcgatca aagttgacgg cgatgcgttc tcattcacct tcttttggcg    38520
```

```
cccacctagc caaatgaggc ttaatgataa cgcgagaacg acacctccga cgatcaattt   38580
ctgagacccc gaaagacgcc ggcgatgttt gtcggagacc agggatccag atgcatcaac   38640
ctcatgtgcc gcttgctgac tatcgttatt catcccttcg cccccttcag gacgcgtttc   38700
acatcgggcc tcaccgtgcc cgtttgcggc ctttggccaa cgggatcgta agcggtgttc   38760
cagatacata gtactgtgtg gccatccctc agacgccaac ctcgggaaac cgaagaaatc   38820
tcgacatcgc tcccttaac tgaatagttg gcaacagctt ccttgccatc aggattgatg   38880
gtgtagatgg agggtatgcg tacattgccc ggaaagtgga ataccgtcgt aaatccattg   38940
tcgaagactt cgagtggcaa cagcgaacga tcgccttggg cgacgtagtg ccaattactg   39000
tccgccgcac caagggctgt gacaggctga tccaataaat tctcagcttt ccgttgatat   39060
tgtgcttccg cgtgtagtct gtccacaaca gccttctgtt gtgcctccct cgccgagcc   39120 gccgcatcgt cggcggggta ggcgaattgg acgctgtaat agagatcggg ctgctcttta   39180
tcgaggtggg acagagtctt ggaacttata ctgaaaacat aacggcgcat cccggagtcg   39240 cttgcgggtta gcacgattac tggctgaggc gtgaggacct ggcttgcctt gaaaaataga   39300
taatttcccc gcggtagggc tgctagatct ttgctatttg aaacggcaac cgctgtcacc   39360
gtttcgttcg tggcgaatgt tacgaccaaa gtagctccaa ccgccgtcga gaggcgcacc   39420
acttgatcgg gattgtaagc caaataacgc atgcgcggat ctagcttgcc cgccattgga   39480
gtgtcttcag cctccgcacc agtcgcagcg gcaaataaac atgctaaaat gaaaagtgct   39540
tttctgatca tggttcgctg tggcctacgt ttgaaacggt atcttccgat gtctgatagg   39600
aggtgacaac cagacctgcc gggttggtta gtctcaatct gccgggcaag ctggtcacct   39660
tttcgtagcg aactgtcgcg gtccacgtac tcaccacagg cattttgccg tcaacgacga   39720
gggtcctttt atagcgaatt tgctgcgtgc ttggagttac atcatttgaa gcgatgtgct   39780
cgacctccac cctgccgcgt ttgccaagaa tgacttgagg cgaactggga ttgggatagt   39840
tgaagaattg ctggtaatcc tggcgcactg ttggggcact gaagttcgat accaggtcgt   39900
aggcgtactg agcggtgtcg gcatcataac tctcgcgcag gcgaacgtac tcccacaatg   39960
aggcgttaac gacggcctcc tcttgagttg caggcaatcg cgagacagac acctcgctgt   40020
caacggtgcc gtccggccgt atccatagat atacgggcac aagcctgctc aacggcacca   40080
ttgtggctat agcgaacgct tgagcaacat ttcccaaaat cgcgatagct gcgacagctg   40140
caatgagttt ggagagacgt cgcgccgatt tcgctcgcgc ggtttgaaag gcttctactt   40200
ccttatagtg ctcggcaagg cttttcgcgcg ccactagcat ggcatattca ggccccgtca   40260
tagcgtccac ccgaattgcc gagctgaaga tctgacggag taggctgcca tcgccccaca   40320
ttcagcggga agatcgggcc tttgcagctc gctaatgtgt cgtttgtctg gcagccgctc   40380
aaagcgacaa ctaggcacag caggcaatac ttcatagaat tctccattga ggcgaatttt   40440
tgcgcgacct agcctcgctc aacctgagcg aagcgacggt acaagctgct ggcagattgg   40500
gttgcgccgc tccagtaact gcctccaatg ttgccggcga tcgccggcaa agcgacaatg   40560
agcgcatccc ctgtcagaaa aaacatatcg agttcgtaaa gaccaatgat cttggccgcg   40620
gtcgtaccgg cgaaggtgat tacaccaagc ataagggtga cgcagtcgc ttcggttagg   40680 atgacgatcg ttgccacgag gtttaagagg agaagcaaga gaccgtaggt gataagttgc   40740
ccgatccact tagctgcgat gtcccgcgtg cgatcaaaaa tatatccgac gaggatcaga   40800
ggcccgatcg cgagaagcac tttcgtgaga attccaacgg cgtcgtaaac tccgaaggca   40860
gaccagagcg tgccgtaaag gacccactgt gccccttgga aagcaaggat gtcctggtcg   40920
```

```
ttcatcggac cgatttcgga tgcgattttc tgaaaaacgg cctgggtcac ggcgaacatt    40980
gtatccaact gtgccggaac agtctgcaga ggcaagccgg ttacactaaa ctgctgaaca    41040
aagtttggga ccgtcttttc gaagatggaa accacatagt cttggtagtt agcctgccca    41100
acaattagag caacaacgat ggtgaccgtg atcacccgag tgataccgct acgggtatcg    41160
acttcgccgc gtatgactaa ataccctga acaataatcc aaagagtgac acaggcgatc     41220
aatggcgcac tcaccgcctc ctggatagtc tcaagcatcg agtccaagcc tgtcgtgaag    41280
gctacatcga agatcgtatg aatggccgta acggcgccg gaatcgtgaa attcatcgat     41340
tggacctgaa cttgactggt ttgtcgcata atgttggata aaatgagctc gcattcggcg    41400
aggatgcggg cggatgaaca aatcgcccag ccttagggga gggcaccaaa gatgacagcg    41460
gtcttttgat gctccttgcg ttgagcggcc gcctcttccg cctcgtgaag gccggcctgc    41520
gcggtagtca tcgttaatag gcttgtcgcc tgtacatttt gaatcattgc gtcatggatc    41580
tgcttgagaa gcaaaccatt ggtcacggtt gcctgcatga tattgcgaga tcgggaaagc    41640
tgagcagacg tatcagcatt cgccgtcaag cgtttgtcca tcgtttccag attgtcagcc    41700
gcaatgccag cgctgtttgc ggaaccggtg atctgcgatc gcaacaggtc cgcttcagca    41760
tcactaccca cgactgcacg atctgtatcg ctggtgatcg cacgtgccgt ggtcgacatt    41820
ggcattcgcg gcgaaaacat ttcattgtct aggtccttcg tcgaaggata ctgatttttc    41880
tggttgagcg aagtcagtag tccagtaacg ccgtaggccg acgtcaacat cgtaaccatc    41940
gctatagtct gagtgagatt ctccgcagtc gcgagcgcag tcgcgagcgt ctcagcctcc    42000
gttgccgggt cgctaacaac aaactgcgcc cgcgcgggct gaatatatag aaagctgcag    42060
gtcaaaactg ttgcaataag ttgcgtcgtc ttcatcgttt cctaccttat caatcttctg    42120
cctcgtggtg acgggccatg aattcgctga ccagccaga tgagttgcct tcttgtgcct     42180
cgcgtagtcg agttgcaaag cgcaccgtgt tggcacgccc cgaaagcacg gcgacatatt    42240
cacgcatatc ccgcagatca aattcgcaga tgacgcttcc actttctcgt ttaagaagaa    42300
acttacggct gccgaccgtc atgtcttcac ggatcgcctg aaattccttt tcggtacatt    42360
tcagtccatc gacataagcc gatcgatctg cggttggtga tggatagaaa atcttcgtca    42420
tacattgcgc aaccaagctg gctcctagcg gcgattccag aacatgctct ggttgctgcg    42480
ttgccagtat tagcatcccg ttgttttttc gaacggtcag gaggaatttg tcgacgacag    42540
tcgaaaattt agggtttaac aaataggcgc gaaactcatc gcagctcatc acaaaacggc    42600
ggccgtcgat catggctcca atccgatgca ggagatatgc tgcagcggga gcgcatactt    42660
cctcgtattc gagaagatgc gtcatgtcga agccggtaat cgacggatct aactttactt    42720
cgtcaacttc gccgtcaaat gcccagccaa gcgcatggcc ccggcaccag cgttggagcc    42780
gcgctcctgc gccttcggcg ggcccatgca acaaaaattc acgtaacccc gcgattgaac    42840
gcatttgtgg atcaaacgag agctgacgat ggataccacg gaccagacgg cggttctctt    42900
ccggagaaat cccaccccga ccatcactct cgatgagagc cacgatccat tcgcgcagaa    42960
aatcgtgtga ggctgctgtg ttttctaggc cacgcaacgg cgccaacccg ctgggtgtgc    43020
ctctgtgaag tgccaaatat gttcctcctg tggcgcgaac cagcaattcg ccaccccggt    43080
ccttgtcaaa gaacacgacc gtacctgcac ggtcgaccat gctctgttcg agcatggcta    43140
gaacaaacat catgagcgtc gtcttacccc tcccgatagg cccgaatatt gccgtcatgc    43200
caacatcgtg ctcatgcggg atatagtcga aaggcgttcc gccattggta cgaaatcggg    43260
```

```
caatcgcgtt gccccagtgg cctgagctgg cgccctctgg aaagttttcg aaagagacaa    43320
accctgcgaa attgcgtgaa gtgattgcgc cagggcgtgt gcgccactta aaattccccg    43380
gcaattggga ccaataggcc gcttccatac caataccttc ttggacaacc acggcacctg    43440
catccgccat tcgtgtccga gcccgcgcgc ccctgtcccc aagactattg agatcgtctg    43500
catagacgca aaggctcaaa tgatgtgagc ccataacgaa ttcgttgctc gcaagtgcgt    43560
cctcagcctc ggataatttg ccgatttgag tcacggcttt atcgccggaa ctcagcatct    43620
ggctcgattt gaggctaagt ttcgcgtgcg cttgcgggcg agtcaggaac gaaaaactct    43680
gcgtgagaac aagtggaaaa tcgagggata gcagcgcgtt gagcatgccc ggccgtgttt    43740
ttgcagggta ttcgcgaaac gaatagatgg atccaacgta actgtctttt ggcgttctga    43800
tctcgagtcc tcgcttgccg caaatgactc tgtcggtata aatcgaagcg ccgagtgagc    43860
cgctgacgac cggaaccggt gtgaaccgac cagtcatgat caaccgtagc gcttcgccaa    43920
tttcggtgaa gagcacaccc tgcttctcgc ggatgccaag acgatgcagg ccatacgctt    43980
taagagagcc agcgacaaca tgccaaagat cttccatgtt cctgatctgg cccgtgagat    44040
cgttttccct ttttccgctt agcttggtga acctcctctt taccttccct aaagccgcct    44100
gtgggtagac aatcaacgta aggaagtgtt cattgcggag gagttggccg agagcacgc     44160
gctgttcaaa agcttcgttc aggctagcgg cgaaaacact acggaagtgt cgcggcgccg    44220
atgatggcac gtcggcatga cgtacgaggt gagcatatat tgacacatga tcatcagcga    44280
tattgcgcaa cagcgtgttg aacgcacgac aacgcgcatt gcgcatttca gtttcctcaa    44340
gctcgaatgc aacgccatca attctcgcaa tggtcatgat cgatccgtct tcaagaagga    44400
cgatatggtc gctgaggtgg ccaatataag ggagatagat ctcaccggat ctttcggtcg    44460
ttccactcgc gccgagcatc acaccattcc tctccctcgt gggggaaccc taattggatt    44520
tgggctaaca gtagcgcccc cccaaactgc actatcaatg cttcttcccg cggtccgcaa    44580
aaatagcagg acgacgctcg ccgcattgta gtctcgctcc acgatgagcc gggctgcaaa    44640
ccataacggc acgagaacga cttcgtagag cgggttctga acgataacga tgacaaagcc    44700
ggcgaacatc atgaataacc ctgccaatgt cagtggcacc ccaagaaaca atgcgggccg    44760
tgtggctgcg aggtaaaggg tcgattcttc caaacgatca gccatcaact accgccagtg    44820
agcgtttggc cgaggaagct cgccccaaac atgataacaa tgccgccgac gacgccggca    44880
accagcccaa gcgaagcccg cccgaacatc caggagatcc cgatagcgac aatgccgaga    44940
acagcgagtg actggccgaa cggaccaagg ataaacgtgc atatattgtt aaccattgtg    45000
gcggggtcag tgccgccacc cgcagattgc gctgcggcgg gtccggatga ggaaatgctc    45060
catgcaattg caccgcacaa gcttggggcg cagctcgata tcacgcgcat catcgcattc    45120
gagagcgaga ggcgatttag atgtaaacgg tatctctcaa agcatcgcat caatgcgcac    45180
ctccttagta taagtcgaat aagacttgat tgtcgtctgc ggatttgccg ttgtcctggt    45240
gtggcggtgg cggagcgatt aaaccgccag cgccatcctc ctgcgagcgg cgctgatatg    45300
accccccaaac atcccacgtc tcttcggatt ttagcgcctc gtgatcgtct tttggaggct    45360
cgattaacgc gggcaccagc gattgagcag ctgtttcaac ttttcgcacg tagccgtttg    45420
caaaaccgcc gatgaaatta ccggtgttgt aagcggagat cgcccgacga agcgcaaatt    45480
gcttctcgtc aatcgttttcg ccgcctgcat aacgactttt cagcatgttt gcagcggcag    45540
ataatgatgt gcacgcctgg agcgcaccgt caggtgtcag accagagcata gaaaaatttc    45600
gagagtttat ttgcatgagg ccaacatcca gcgaatgccg tgcatcgaga cggtgcctga    45660
```

```
cgacttgggt tgcttggctg tgatcttgcc agtgaagcgt ttcgccggtc gtgttgtcat   45720
gaatcgctaa aggatcaaag cgactctcca ccttagctat cgccgcaagc gtagatgtcg   45780
caactgatgg ggcacacttg cgagcaacat ggtcaaactc agcagatgag agtggcgtgg   45840
caaggctcga cgaacagaag gagaccatca aggcaagaga aagcgacccc gatctcttaa   45900 gcataccttta tctccttagc tcgcaactaa caccgcctct cccgttggaa gaagtgcgtt   45960
gttttatgtt gaagattatc gggagggtcg gttactcgaa aattttcaat tgcttctttta  46020 tgatttcaat tgaagcgaga aacctcgccc ggcgtcttgg aacgcaacat ggaccgagaa   46080
ccgcgcatcc atgactaagc aaccggatcg acctattcag gccgcagttg gtcaggtcag   46140
gctcagaacg aaaatgctcg gcgaggttac gctgtctgta aacccattcg atgaacggga   46200
agcttccttc cgattgctct tggcaggaat attgggcccat gcctgcttgc gctttgcaaa   46260
tgctcttatc gcgttggtat catatgcctt gtccgccagc agaaacgcac tctaagcgat   46320
tatttgtaaa aatgtttcgg tcatgcgcg gtcatgggct tgacccgctg tcagcgcaag   46380
acggatcggt caaccgtcgg catcgacaac agcgtgaatc ttggtggtca aaccgccacg   46440
ggaacgtccc atacagccat cgtcttgatc ccgctgtttc ccgtcgccgc atgttggtgg   46500
acgcggacac aggaactgtc aatcatgacg acattctatc gaaagccttg gaaatcacac   46560
tcagaatatg atcccagacg tctgcctcac gccatcgtac aaagcgattg tagcaggttg   46620
tacaggaacc gtatcgatca ggaacgtctg cccagggcgg gcccgtccgg aagcgccaca   46680
agatgacatt gatcacccgc gtcaacgcgc ggcacgcgac gcggcttatt tgggaacaaa   46740
ggactgaaca acagtccatt cgaaatcggt gacatcaaag cggggacggg ttatcagtgg   46800
cctccaagtc aagcctcaat gaatcaaaat cagaccgatt tgcaaacctg atttatgagt   46860
gtgcggccta aatgatgaaa tcgtccttct agatcgcctc cgtggtgtag caacacctcg   46920
cagtatcgcc gtgctgacct tggccaggga attgactggc aagggtgctt tcacatgacc   46980
gctcttttgg ccgcgataga tgatttcgtt gctgcttttgg gcacgtagaa ggagagaagt   47040
catatcggag aaattcctcc tggcgcgaga gcctgctcta tcgcgacggc atcccactgt   47100
cgggaacaga ccggatcatt cacgaggcga aagtcgtcaa cacatgcgtt ataggcatct   47160
tcccttgaag gatgatcttg ttgctgccaa tctggaggtg cggcagccgc aggcagatgc   47220
gatctcagcg caacttgcgg caaaacatct cactcacctg aaaaccacta gcgagtctcg   47280
cgatcagacg aaggccttt acttaacgac acaatatccg atgtctgcat cacaggcgtc   47340
gctatcccag tcaatactaa agcggtgcag gaactaaaga ttactgatga cttaggcgtg   47400
ccacgaggcc tgagacgacg cgcgtagaca gttttttgaa atcattatca aagtgatggc   47460
ctccgctgaa gcctatcacc tctgcgccgg tctgtcggag agatgggcaa gcattattac   47520
ggtcttcgcg cccgtacatg cattggacga ttgcagggtc aatggatctg agatcatcca   47580
gaggattgcc gcccttacct tccgtttcga gttggagcca gcccctaaat gagacgacat   47640
agtcgacttg atgtgacaat gccaagagag agatttgctt aacccgattt ttttgctcaa   47700
gcgtaagcct attgaagctt gccggcatga cgtccgcgcc gaaagaatat cctacaagta   47760
aaacattctg cacaccgaaa tgcttggtgt agacatcgat tatgtgacca agatccttag   47820
cagtttcgct tggggaccgc tccgaccaga aataccgaag tgaactgacg ccaatgacag   47880
gaatcccttc cgtctgcaga taggtaccat cgatagatct gctgcctcgc gcgtttcggt   47940
gatgacggtg aaaacctctg acacatgcag ctcccggaga cggtcacagc ttgtctgtaa   48000
```

```
gcggatgccg ggagcagaca agcccgtcag ggcgcgtcag cgggtgttgg cgggtgtcgg    48060
ggcgcagcca tgacccagtc acgtagcgat agcggagtgt atactggctt aactatgcgg    48120
catcagagca gattgtactg agagtgcacc atatgcggtg tgaaataccg cacagatgcg    48180
taaggagaaa ataccgcatc aggcgctctt ccgcttcctc gctcactgac tcgctgcgct    48240
cggtcgttcg gctgcggcga gcggtatcag ctcactcaaa ggcggtaata cggttatcca    48300
cagaatcagg ggataacgca ggaaagaaca tgtgagcaaa aggccagcaa aaggccagga    48360
accgtaaaaa ggccgcgttg ctggcgtttt tccataggct ccgcccccct gacgagcatc    48420
acaaaaatcg acgctcaagt cagaggtggc gaaacccgac aggactataa agataccagg    48480
cgtttccccc tggaagctcc ctcgtgcgct ctcctgttcc gaccctgccg cttaccggat    48540
acctgtccgc ctttctccct tcgggaagcg tggcgctttc tcatagctca cgctgtaggt    48600
atctcagttc ggtgtaggtc gttcgctcca agctgggctg tgtgcacgaa ccccccgttc    48660
agcccgaccg ctgcgcctta tccggtaact atcgtcttga gtccaacccg gtaagacacg    48720
acttatcgcc actggcagca gccactggta acaggattag cagagcgagg tatgtaggcg    48780
gtgctacaga gttcttgaag tggtggccta actacggcta cactagaagg acagtatttg    48840
gtatctgcgc tctgctgaag ccagttacct tcggaaaaag agttggtagc tcttgatccg    48900
gcaaacaaac caccgctggt agcggtggtt tttttgtttg caagcagcag attacgcgca    48960
gaaaaaaagg atctcaagaa gatcctttga tcttttctac ggggtctgac gctcagtgga    49020
acgaaaactc acgttaaggg attttggtca tgagattatc aaaaaggatc ttcacctaga    49080
tccttttaaa ttaaaaatga agttttaaat caatctaaag tatatatgag taaacttggt    49140
ctgacagtta ccaatgctta atcagtgagg cacctatctc agcgatctgt ctatttcgtt    49200
catccatagt tgcctgactc cccgtcgtgt agataactac gatacgggag ggcttaccat    49260
ctggccccag tgctgcaatg ataccgcgag acccacgctc accggctcca gatttatcag    49320
caataaacca gccagccgga agggccgagc gcagaagtgg tcctgcaact ttatccgcct    49380
ccatccagtc tattaattgt tgccgggaag ctagagtaag tagttcgcca gttaatagtt    49440
tgcgcaacgt tgttgccatt gctgcagggg ggggggggg ggggacttc cattgttcat    49500 tccacggaca aaacagaga aggaaacga cagaggccaa aaagcctcgc tttcagcacc    49560
tgtcgtttcc tttcttttca gagggtattt taaataaaaa cattaagtta tgacgaagaa    49620
gaacggaaac gccttaaacc ggaaaatttt cataaatagc gaaaaccgc gaggtcgccg    49680 ccccgtaacc tgtcggatca ccggaaagga cccgtaaagt gataatgatt atcatctaca    49740
tatcacaacg tgcgtggagg ccatcaaacc acgtcaaata atcaattatg acgcaggtat    49800
cgtattaatt gatctgcatc aacttaacgt aaaaacaact tcagacaata caaatcagcg    49860
acactgaata cggggcaacc tcatgtcccc cccccccc cccctgcagg catcgtggtg    49920
tcacgctcgt cgtttggtat ggcttcattc agctccggtt cccaacgatc aaggcgagtt    49980
acatgatccc ccatgttgtg caaaaaagcg gttagctcct tcggtcctcc gatcgttgtc    50040
agaagtaagt tggccgcagt gttatcactc atggttatgg cagcactgca taattctctt    50100
actgtcatgc catccgtaag atgcttttct gtgactggtg agtactcaac caagtcattc    50160
tgagaatagt gtatgcggcg accgagttgc tcttgcccgg cgtcaacacg ggataatacc    50220
gcgccacata gcagaacttt aaaagtgctc atcattggaa aacgttcttc ggggcgaaaa    50280
ctctcaagga tcttaccgct gttgagatcc agttcgatgt aacccactcg tgcacccaac    50340
tgatcttcag catcttttac tttcaccagc gtttctgggt gagcaaaaac aggaaggcaa    50400
```

| | | | |
|---|---|---|---|
| aatgccgcaa aaaagggaat aagggcgaca cggaaatgtt gaatactcat actcttcctt | 50460 |
| tttcaatatt attgaagcat ttatcagggt tattgtctca tgagcggata catatttgaa | 50520 |
| tgtatttaga aaaataaaca aatagggggtt ccgcgcacat ttccccgaaa agtgccacct | 50580 |
| gacgtctaag aaaccattat tatcatgaca ttaacctata aaaataggcg tatcacgagg | 50640 |
| cccttcgtc ttcaagaatt ggtcgacgat cttgctgcgt tcggatattt tcgtggagtt | 50700 |
| cccgccacag acccggattg aaggcgagat ccagcaactc gcgccagatc atcctgtgac | 50760 |
| ggaactttgg cgcgtgatga ctggccagga cgtcggccga agagcgaca agcagatcac | 50820 |
| gcttttcgac agcgtcggat ttgcgatcga ggattttcg gcgctgcgct acgtccgcga | 50880 |
| ccgcgttgag ggatcaagcc acagcagccc actcgacctt ctagccgacc cagacgagcc | 50940 |
| aagggatctt tttggaatgc tgctccgtcg tcaggctttc cgacgtttgg gtggttgaac | 51000 |
| agaagtcatt atcgtacgga atgccaagca ctcccgaggg gaaccctgtg gttggcatgc | 51060 |
| acatacaaat ggacgaacgg ataaaccttt tcacgcccct ttaaatatcc gttattctaa | 51120 |
| taaacgctct tttctcttag gtttacccgc caatatatcc tgtcaaacac tgatagttta | 51180 |
| aactgaaggc gggaaacgac aatctgatca tgagcggaga attaagggag tcacgttatg | 51240 |
| accccgccg atgacgcggg acaagccgtt ttacgtttgg aactgacaga accgcaacgt | 51300 |
| tgaaggagcc actcagcaag ctggtacgat tgtaatacga ctcactatag ggcgaattga | 51360 |
| gcgctgttta acgctcttc aactggaaga gcggttacta ccggttaagt gactagggtc | 51420 |

<210> SEQ ID NO 7
<211> LENGTH: 50751
<212> TYPE: DNA
<213> ORGANISM: artificial sequence
<220> FEATURE:
<223> OTHER INFORMATION: PHP34005 test vector

<400> SEQUENCE: 7

| | |
|---|---|
| acgtgaccct agtcacttag gttaccagag ctggtcacct ttgtccacca agatggaact | 60 |
| gcggccgctc attaattaag tcaggcgcgc ctctagttga agacacgttc atgtcttcat | 120 |
| cgtaagaaga cactcagtag tcttcggcca gaatggccat ctggattcag caggcctaga | 180 |
| aggccattta atcctgagg atctggtctt cctaaggacc cgggatatcg ctatcaactt | 240 |
| tgtatagaaa agttgggccg aattcgagct cggtacggcc agaatggccc ggaccgggtt | 300 |
| accgaattcg agctcggtac cactagtaag cttgccgcaa ttcgcaaaac acacctagac | 360 |
| tagatttgtt ttgctaaccc aattgatatt aattatatat gattaatatt tatatgtata | 420 |
| tggatttggt taatgaaatg catctggttc atcaaagaat tataaagaca cgtgacattc | 480 |
| atttaggata agaaatatgg atgatctctt tctcttttat tcagataact agtaattaca | 540 |
| cataacacac aactttgatg cccacattat agtgattagc atgtcactat gtgtgcatcc | 600 |
| ttttatttca tacattaatt aagttggcca atccagaaga tggacaagtc tggatcttca | 660 |
| ttgtttgcct ccctgctgcg gttttcacc gaagttcatg ccagtccagc gttttgcag | 720 |
| cagaaaagcc gccgacttcg gtttgcggtc gcgagtgaag atcccttct tgttaccgcc | 780 |
| aacgcgcaat atgccttgcg aggtcgcaaa atcggcgaaa ttccatacct gttcaccgac | 840 |
| gacggcgctg acgcgatcaa agacgcggtg atacatatcc agccatgcac actgatactc | 900 |
| ttcactccac atgtcggtgt acattgagtg cagcccggct aacgtatcca cgccgtattc | 960 |
| ggtgatgata atcggctgat gcagtttctc ctgccaggcc agaagttctt tttccagtac | 1020 |

```
cttctctgcc gtttccaaat cgccgctttg gacataccat ccgtaataac ggttcaggca    1080
cagcacatca aagagatcgc taatggtatc ggtgtgagcg tcgcagaaca ttacattgac    1140
gcaggtgatc ggacgcgtcg ggtcgagttt acgcgttgct tccgccagtg gcgcgaaata    1200
ttcccgtgca ccttgcggac gggtatccgg ttcgttggca atactccaca tcaccacgct    1260
tgggtggttt ttgtcacgcg ctatcagctc tttaatcgcc tgtaagtgcg cttgctgagt    1320
ttccccgttg actgcctctt cgctgtacag ttctttcggc ttgttgcccg cttcgaaacc    1380
aatccctaaa gagaggttaa agccgacagc agcagtttca tcaatcacca cgatgccatg    1440
ttcatctgcc cagtcgagca tctcttcagc gtaagggtaa tgcgaggtac ggtaggagtt    1500
ggccccaatc cagtccatta atgcgtggtc gtgcaccatc agcacgttat cgaatccttt    1560
gccacgcaag tccgcatctt catgacgacc aaagccagta agtagaacg gtttgtggtt     1620 aatcaggaac tgttggccct tcactgccac tgaccggatg ccgacgcgaa gcgggtagat    1680
atcacactct gtctggcttt tggctgtgac gcacagttca tagagataac cttcacccgg    1740
ttgccagagg tgcggattca ccacttgcaa agtcccgcta gtgccttgtc cagttgcaac    1800
cacctgttga tccgcatcac gcagttcaac gctgacatca ccattggcca ccacctgcca    1860
gtcaacagac gcgtggttac agtcttgcgc gacatgcgtc accacggtga tatcgtccac    1920
ccaggtgttc ggcgtggtgt agagcattac gctgcgatgg attccggcat agttaaagaa    1980
atcatggaag taagactgct tttcttgcc gttttcgtcg gtaatcacca ttcccggcgg     2040
gatagtctgc cagttcagtt cgttgttcac acaaacggtg atacctgcac atcaacaaat    2100
tttggtcata tattagaaaa gttataaatt aaaatataca cacttataaa ctacagaaaa    2160
gcaattgcta tatactacat tcttttattt tgaaaaaaat atttgaaata ttatattact    2220
actaattaat gataattatt atatatatat caaaggtaga agcagaaact tacgtacact    2280
tttcccggca ataacatacg gcgtgacatc ggcttcaaat ggcgtatagc cgccctgatg    2340
ctccatcact tcctgattat tgacccacac tttgccgtaa tgagtgaccg catcgaaacg    2400
cagcacgata cgctggcctg cccaaccttt cggtataaag acttcgcgct gataccagac    2460
gttgcccgca taattacgaa tatctgcatc ggcgaactga tcgttaaaac tgcctggcac    2520
agcaattgcc cggctttctt gtaacgcgct ttcccaccaa cgctgatcaa ttccacagtt    2580
ttcgcgatcc agactgaatg cccacaggcc gtcgagtttt ttgatttcac gggttggggt    2640
ttctacagga cggaccatgg tgtcgtgtgg atccaaattg tatgcaaggt gaatgacttt    2700
cttttcgtaa actagatagg agtactcctc caggatgctt aacccgtatt gacgtacaga    2760
ggtctatgat cctttgtttt ataaaggagc ttgtagttca gtcagtctta tcttcacga    2820 tgcccatgtt tctatatagg atattatctt ggctttgtaa gtacttcacg caggttatgt    2880
tctgtttcta ggatattatc ctcatacatg cgaagaacca attttcccc cattctcttc     2940 gggtactttt tcttgggtag gcatgctctc ttggaccaac tagcataaaa cataatcatt    3000
tttccctaca gccttgacca gctataatcg aaatcatgct cattttcta agaaagactg      3060 aatacagctc caatttaaac aatttaaatc ataaacttgt aactcaatta gagaaaagca    3120
gagcccttcg gctcctatct aaaggaatta ccccatgaaa gccataaaaa cgaaccttgc    3180
tctgatacca gacgggtcta cgctcgcgga actaggatct tgcgctctac tcgcacaaag    3240
tgaactcgca caaagtgtgt tcaagcaca gaagttttta tttctcaaat caggagtaaa     3300
ctcgcgttgt ggtgcgtgtt tgcaacctga atacaaggcc ccttatatag agagttgtgg    3360
agctttctgg catcgttagg tggcatccac caataatgca gataagcatc atcacatgtc    3420
```

```
tctggcctaa caactttgcg taagaatcct gcaaagttac taaaggtcat cgtgcgtgac    3480
tagacaacgc acaccgacaa acttaaaata aagagacatt atactttgtc tcctctttac    3540
ataaagtgag tggtatccag ctcactccgc atcttatcag tcttcacacc ggttggtatc    3600
aacacgtggt aggggtccgc cacttccgct tcagtcatca ttactgatat ccagcagatc    3660
tagagcatct tcaataagat attcttgttc tgcacgcaga ttttcttgct ccctcagtaa    3720
ttcctcccac agtgagtctt ctgatatttc ttcaagtttc ttctcccatc tgatcttttc    3780
ctgcacaaac gagtcaattt ggtctttcca gacccaagta aaacaagtgt tagtttcaca    3840
ggagtaaaac tccctgtcag gatttctgga tgttctggag atcttcagtt ttgctggttt    3900
attgcatcca catttgaaaa ccggctcttc acttagtgtt agcacattga tttgatgcaa    3960
cctgtagcct ttgctcaacc agtcttcata tcttttttaca acatcattaa ctctctgttt    4020
tgcatcggtg tttcccttgt gaaataccctc ctccactgca ttgatcaaca caccttcaga    4080
ttgatgcttt tccggatgga gaataatctt taccagtctt gacagagtgt ctgctaaaac    4140
gttgtccttt ccgtcaatgt gttcaaactt aatctcaaga cctgtcccgg taatgtaatc    4200
tgtgaaggca agccatctga ctcttgatgg tttatgatca ctgcttttct tgtaaaagct    4260
cactattgct tgactgtcag ttctgattat gagctctttg taagcttggt cacccggtcc    4320
gggcctagaa ggccagcttc ggccgccccg ggcaacttta ttatacaaag ttgatagata    4380
tcggaccgat taaactttaa ttcggtccga agcttgcatg cctgcagtgc agcgtgaccc    4440
ggtcgtgccc ctctctagag ataatgagca ttgcatgtct aagttataaa aaattaccac    4500 atatttttt tgtcacactt gtttgaagtg cagtttatct atctttatac atatatttaa    4560 acttactct acgaataata taatctatag tactacaata atatcagtgt tttagagaat    4620
catataaatg aacagttaga catggtctaa aggacaattg agtattttga caacaggact    4680
ctacagtttt atcttttag tgtgcatgtg ttctcctttt tttttgcaaa tagcttcacc    4740
tatataatac ttcatccatt ttattagtac atccatttag ggtttagggt taatggtttt    4800
tatagactaa tttttttagt acatctattt tattctattt tagcctctaa attaagaaaa    4860
ctaaaactct attttagttt ttttatttaa taatttagat ataaaataga ataaaataaa    4920
gtgactaaaa attaaacaaa tacccttttaa gaaattaaaa aaactaagga aacattttc    4980 ttgtttcgag tagataatgc cagcctgtta acgccgtcg acgagtctaa cggacaccaa    5040
ccagcgaacc agcagcgtcg cgtcgggcca agcgaagcag acggcacggc atctctgtcg    5100
ctgcctctgg accccctctcg agagttccgc tccaccgttg gacttgctcc gctgtcggca    5160
tccagaaatt gcgtggcgga gcggcagacg tgagccggca cggcaggcgg cctcctcctc    5220
ctctcacggc accggcagct acgggggatt ccttccccac cgctccttcg ctttcccttc    5280
ctcgcccgcc gtaataaata gacaccccct ccacaccctc tttccccaac ctcgtgttgt    5340
tcggagcgca cacacacaca accagatctc ccccaaatcc acccgtcggc acctccgctt    5400
caaggtacgc cgctcgtcct ccccccccccc cctctctacc ttctctagat cggcgttccg    5460
gtccatgcat ggttagggcc cggtagttct acttctgttc atgtttgtgt tagatccgtg    5520
tttgtgttag atccgtgctg ctagcgttcg tacacggatg cgacctgtac gtcagacacg    5580
ttctgattgc taacttgcca gtgtttctct ttggggaatc ctgggatggc tctagccgtt    5640
ccgcagacgg gatcgatttc atgattttt ttgtttcgtt gcatagggtt tggtttgccc    5700 ttttcctta tttcaatata tgccgtgcac ttgtttgtcg ggtcatcttt tcatgctttt    5760
```

```
ttttgtcttg gttgtgatga tgtggtctgg ttgggcggtc gttctagatc ggagtagaat    5820
tctgtttcaa actacctggt ggatttatta attttggatc tgtatgtgtg tgccatacat    5880
attcatagtt acgaattgaa gatgatggat ggaaatatcg atctaggata ggtatacatg    5940
ttgatgcggg ttttactgat gcatatacag agatgctttt tgttcgcttg gttgtgatga    6000
tgtggtgtgg ttgggcggtc gttcattcgt tctagatcgg agtagaatac tgtttcaaac    6060
tacctggtgt atttattaat tttggaactg tatgtgtgtg tcatacatct tcatagttac    6120
gagtttaaga tggatggaaa tatcgatcta ggataggtat acatgttgat gtgggtttta    6180
ctgatgcata tacatgatgg catatgcagc atctattcat atgctctaac cttgagtacc    6240
tatctattat aataaacaag tatgttttat aattattttg atcttgatat acttggatga    6300
tggcatatgc agcagctata tgtggatttt tttagccctg ccttcatacg ctatttattt    6360
gcttggtact gtttcttttg tcgatgctca ccctgttgtt tggtgttact tctgcaggtc    6420
gactttaact tagcctagga tccacacgac accatgtccc ccgagcgccg ccccgtcgag    6480
atccgcccgg ccaccgccgc cgacatggcc gccgtgtgcg acatcgtgaa ccactacatc    6540
gagacctcca ccgtgaactt ccgcaccgag ccgcagaccc gcaggagtg gatcgacgac    6600
ctggagcgcc tccaggaccg ctacccgtgg ctcgtggccg aggtggaggg cgtggtggcc    6660
ggcatcgcct acgccggccc gtggaaggcc cgcaacgcct acgactggac cgtggagtcc    6720
accgtgtacg tgtcccaccg ccaccagcgc ctcggcctcg gctccaccct ctacacccac    6780
ctcctcaaga gcatggaggc ccagggcttc aagtccgtgg tggccgtgat cggcctcccg    6840
aacgacccgt ccgtgcgcct ccacgaggcc ctcggctaca ccgcccgcgg cacccttccgc   6900
gccgccggct acaagcacgg cggctggcac gacgtcggct tctggcagcg cgacttcgag    6960
ctgccggccc cgccgcgccc ggtgcgcccg gtgacgcaga tctgagtcga acctagact     7020
tgtccatctt ctggattggc caacttaatt aatgtatgaa ataaaggat gcacacatag     7080
tgacatgcta atcactataa tgtgggcatc aaagttgtgt gttatgtgta attactagtt    7140
atctgaataa aagagaaaga gatcatccat atttcttatc ctaaatgaat gtcacgtgtc    7200
tttataattc tttgatgaac cagatgcatt tcattaacca aatccatata catataaata    7260
ttaatcatat ataattaata tcaattgggt tagcaaaaca aatctagtct aggtgtgttt    7320
tgcgaatgcg gccgataagt gactagggtc acgtgaccct agtcacttag gtaccgagct    7380
cgaattcatt ccgattaatc gtggcctctt gctcttcagg atgaagagct atgtttaaac    7440
gtgcaagcgc tactagacaa ttcagtacat taaaaacgtc cgcaatgtgt tattaagttg    7500
tctaagcgtc aatttgttta caccacaata tatcctgcca ccagccagcc aacagctccc    7560
cgaccggcag ctcggcacaa aatcaccact cgatacaggc agcccatcag tccgggacgg    7620
cgtcagcggg agagccgttg taaggcggca gactttgctc atgttaccga tgctattcgg    7680
aagaacggca actaagctgc cgggtttgaa acacgatga tctcgcggag ggtagcatgt    7740
tgattgtaac gatgacagag cgttgctgcc tgtgatcaaa tatcatctcc ctcgcagaga    7800
tccgaattat cagccttctt attcatttct cgcttaaccg tgacaggctg tcgatcttga    7860
gaactatgcc gacataatag gaaatcgctg ataaagccg ctgaggaagc tgagtggcgc     7920
tatttcttta gaagtgaacg ttgacgatcg tcgaccgtac cccgatgaat taattcggac    7980
gtacgttctg aacacagctg gatacttact tgggcgattg tcatacatga catcaacaat    8040
gtacccgttt gtgtaaccgt ctcttggagg ttcgtatgac actagtggtt cccctcagct    8100
tgcgactaga tgttgaggcc taacatttta ttagagagca ggctagttgc ttagatacat    8160
```

```
gatcttcagg ccgttatctg tcagggcaag cgaaaattgg ccatttatga cgaccaatgc   8220
cccgcagaag ctcccatctt tgccgccata dacgccgcgc ccccttttg gggtgtagaa    8280 catccttttg ccagatgtgg aaaagaagtt cgttgtccca ttgttggcaa tgacgtagta   8340
gccggcgaaa gtgcgagacc catttgcgct atatataagc ctacgatttc cgttgcgact   8400
attgtcgtaa ttggatgaac tattatcgta gttgctctca gagttgtcgt aatttgatgg   8460
actattgtcg taattgctta tggagttgtc gtagttgctt ggagaaatgt cgtagttgga   8520
tggggagtag tcatagggaa gacgagcttc atccactaaa acaattggca ggtcagcaag   8580
tgcctgcccc gatgccatcg caagtacgag gcttagaacc accttcaaca gatcgcgcat   8640
agtcttcccc agctctctaa cgcttgagtt aagccgcgcc gcgaagcggc gtcggcttga   8700
acgaattgtt agacattatt tgccgactac cttggtgatc tcgcctttca cgtagtgaac   8760
aaattcttcc aactgatctg cgcgcgaggc caagcgatct tcttgtccaa gataagcctg   8820
cctagcttca agtatgacgg gctgatactg ggccggcagg cgctccattg cccagtcggc   8880
agcgacatcc ttcggcgcga ttttgccggt tactgcgctg taccaaatgc gggacaacgt   8940
aagcactaca tttcgctcat cgccagccca gtcgggcggc gagttccata gcgttaaggt   9000
ttcatttagc gcctcaaata gatcctgttc aggaaccgga tcaaagagtt cctccgccgc   9060
tggacctacc aaggcaacgc tatgttctct tgcttttgtc agcaagatag ccagatcaat   9120
gtcgatcgtg gctggctcga agatacctgc aagaatgtca ttgcgctgcc attctccaaa   9180
ttgcagttcg cgcttagctg gataacgcca cggaatgatg tcgtcgtgca caacaatggt   9240
gacttctaca gcgcggagaa tctcgctctc tccagggaaa gccgaagttt ccaaaaggtc   9300
gttgatcaaa gctcgccgcg ttgtttcatc aagccttaca gtcaccgtaa ccagcaaatc   9360
aatatcactg tgtggcttca ggccgccatc cactgcggag ccgtacaaat gtacggccag   9420
caacgtcggt tcgagatggc gctcgatgac gccaactacc tctgatagtt gagtcgatac   9480
ttcggcgatc accgcttccc tcatgatgtt taactcctga attaagccgc ccgcgaagc   9540 ggtgtcggct tgaatgaatt gttaggcgtc atcctgtgct cccgagaacc agtaccagta   9600
catcgctgtt tcgttcgaga cttgaggtct agttttatac gtgaacaggt caatgccgcc   9660
gagagtaaag ccacattttg cgtacaaatt gcaggcaggt acattgttcg tttgtgtctc   9720
taatcgtatg ccaaggagct gtctgcttag tgcccacttt ttcgcaaatt cgatgagact   9780
gtgcgcgact cctttgcctc ggtgcgtgtg cgacacaaca atgtgttcga tagaggctag   9840
atcgttccat gttgagttga gttcaatctt cccgacaagc tcttggtcga tgaatgcgcc   9900
atagcaagca gagtcttcat cagagtcatc atccgagatg taatccttcc ggtagggct    9960 cacacttctg gtagatagtt caaagccttg gtcggatagg tgcacatcga acacttcacg   10020
aacaatgaaa tggttctcag catccaatgt ttccgccacc tgctcaggga tcaccgaaat   10080
cttcatatga cgcctaacgc ctggcacagc ggatcgcaaa cctggcgcgg cttttggcac   10140
aaaaggcgtg acaggtttgc gaatccgttg ctgccacttg ttaacccttt tgccagattt   10200
ggtaactata atttatgtta gaggcgaagt cttgggtaaa aactggccta aaattgctgg   10260
ggatttcagg aaagtaaaca tcaccttccg gctcgatgtc tattgtagat atatgtagtg   10320
tatctacttg atcgggggat ctgctgcctc gcgcgtttcg gtgatgacgg tgaaaacctc   10380
tgacacatgc agctcccgga gacggtcaca gcttgtctgt aagcggatgc cgggagcaga   10440
caagcccgtc agggcgcgtc agcgggtgtt ggcgggtgtc ggggcgcagc catgacccag   10500
```

```
tcacgtagcg atagcggagt gtatactggc ttaactatgc ggcatcagag cagattgtac   10560
tgagagtgca ccatatgcgg tgtgaaatac cgcacagatg cgtaaggaga aaataccgca   10620
tcaggcgctc ttccgcttcc tcgctcactg actcgctgcg ctcggtcgtt cggctgcggc   10680
gagcggtatc agctcactca aaggcggtaa tacggttatc cacagaatca ggggataacg   10740
caggaaagaa catgtgagca aaaggccagc aaaaggccag gaaccgtaaa aaggccgcgt   10800
tgctggcgtt tttccatagg ctccgccccc ctgacgagca tcacaaaaat cgacgctcaa   10860
gtcagaggtg gcgaaacccg acaggactat aaagatacca ggcgtttccc cctggaagct   10920
ccctcgtgcg ctctcctgtt ccgaccctgc cgcttaccgg atacctgtcc gcctttctcc   10980
cttcgggaag cgtggcgctt tctcatagct cacgctgtag gtatctcagt tcggtgtagg   11040
tcgttcgctc caagctgggc tgtgtgcacg aaccccccgt tcagcccgac cgctgcgcct   11100
tatccggtaa ctatcgtctt gagtccaacc cggtaagaca cgacttatcg ccactggcag   11160
cagccactgg taacaggatt agcagagcga ggtatgtagg cggtgctaca gagttcttga   11220
agtggtggcc taactacggc tacactagaa ggacagtatt tggtatctgc gctctgctga   11280
agccagttac cttcggaaaa agagttggta gctcttgatc cggcaaacaa accaccgctg   11340
gtagcggtgg ttttttgtt tgcaagcagc agattacgcg cagaaaaaaa ggatctcaag   11400
aagatccttt gatcttttct acggggtctg acgctcagtg gaacgaaaac tcacgttaag   11460
ggattttggt catgagatta tcaaaaagga tcttcaccta gatcctttta aattaaaaat   11520
gaagttttaa atcaatctaa agtatatatg agtaaacttg gtctgacagt taccaatgct   11580
taatcagtga ggcacctatc tcagcgatct gtctatttcg ttcatccata gttgcctgac   11640
tccccgtcgt gtagataact acgatacggg agggcttacc atctggcccc agtgctgcaa   11700
tgataccgcg agacccacgc tcaccggctc cagatttatc agcaataaac cagccagccg   11760
gaagggccga gcgcagaagt ggtcctgcaa ctttatccgc ctccatccag tctattaatt   11820
gttgccggga agctagagta agtagttcgc cagttaatag tttgcgcaac gttgttgcca   11880
ttgctgcagg gggggggggg ggggggttcc attgttcatt ccacggacaa aaacagagaa   11940
aggaaacgac agaggccaaa aagctcgctt tcagcacctg tcgttccttt cttttcaga   12000
gggtatttta aataaaaaca ttaagttatg acgaagaaga acggaaacgc cttaaaccgg   12060
aaaatttca taaatagcga aaacccgcga ggtcgccgcc ccgtaacctg tcggatcacc   12120
ggaaaggacc cgtaaagtga taatgattat catctacata tcacaacgtg cgtggaggcc   12180
atcaaaccac gtcaaataat caattatgac gcaggtatcg tattaattga tctgcatcaa   12240
cttaacgtaa aaacaacttc agacaataca aatcagcgac actgaatacg ggcaaccctc   12300
atgtccccc ccccccccc cctgcaggca tcgtggtgtc acgctcgtcg tttggtatgg   12360
cttcattcag ctccggttcc caacgatcaa ggcgagttac atgatccccc atgttgtgca   12420
aaaaagcggt tagctccttc ggtcctccga tcgttgtcag aagtaagttg gccgcagtgt   12480
tatcactcat ggttatggca gcactgcata attctcttac tgtcatgcca tccgtaagat   12540
gcttttctgt gactggtgag tactcaacca agtcattctg agaatagtgt atgcggcgac   12600
cgagttgctc ttgcccggcg tcaacacggg ataataccgc gccacatagc agaactttaa   12660
aagtgctcat cattggaaaa cgttcttcgg ggcgaaaact ctcaaggatc ttaccgctgt   12720
tgagatccag ttcgatgtaa cccactcgtg cacccaactg atcttcagca tcttttactt   12780
tcaccagcgt ttctgggtga gcaaaaacag gaaggcaaaa tgccgcaaaa aagggaataa   12840
gggcgacacg gaaatgttga atactcatac tcttcctttt tcaatattat tgaagcattt   12900
```

```
atcagggtta ttgtctcatg agcggataca tatttgaatg tatttagaaa aataaacaaa   12960 tagggttcc  gcgcacattt ccccgaaaag tgccacctga cgtctaagaa accattatta   13020
tcatgacatt aacctataaa aataggcgta tcacgaggcc ctttcgtctt caagaattcg   13080
gagcttttgc cattctcacc ggattcagtc gtcactcatg gtgatttctc acttgataac   13140 cttattttg  acgagggaa  attaataggt tgtattgatg ttggacgagt cggaatcgca   13200
gaccgatacc aggatcttgc catcctatgg aactgcctcg gtgagttttc tccttcatta   13260
cagaaacggc tttttcaaaa atatggtatt gataatcctg atatgaataa attgcagttt   13320
catttgatgc tcgatgagtt tttctaatca gaattggtta attggttgta acactggcag   13380
agcattacgc tgacttgacg ggacggcggc tttgttgaat aaatcgaact tttgctgagt   13440
tgaaggatca gatcacgcat cttcccgaca acgcagaccg ttccgtggca agcaaaagt    13500 tcaaaatcac caactggtcc acctacaaca aagctctcat caaccgtggc tccctcactt   13560
tctggctgga tgatggggcg attcaggcct ggtatgagtc agcaacacct tcttcacgag   13620
gcagacctca gcgccagaag gccgccagag aggccgagcg cggccgtgag gcttggacgc   13680
tagggcaggg catgaaaaag cccgtagcgg gctgctacgg gcgtctgacg cggtggaaag   13740
ggggagggga tgttgtctac atggctctgc tgtagtgagt gggttgcgct ccggcagcgg   13800
tcctgatcaa tcgtcaccct ttctcggtcc ttcaacgttc ctgacaacga gcctccttt    13860 cgccaatcca tcgacaatca ccgcgagtcc ctgctcgaac gctgcgtccg gaccggcttc   13920
gtcgaaggcg tctatcgcgg cccgcaacag cggcgagagc ggagcctgtt caacggtgcc   13980
gccgcgctcg ccggcatcgc tgtcgccggc ctgctcctca agcacggccc caacagtgaa   14040
gtagctgatt gtcatcagcg cattgacggc gtccccggcc gaaaaacccg cctcgcagag   14100
gaagcgaagc tgcgcgtcgg ccgtttccat ctgcggtgcg cccggtcgcg tgccggcatg   14160
gatgcgcgcg ccatcgcggt aggcgagcag cgcctgcctg aagctgcggg cattcccgat   14220
cagaaatgag cgccagtcgt cgtcggctct cggcaccgaa tgcgtatgat tctccgccag   14280
catggcttcg gccagtgcgt cgagcagcgc ccgcttgttc ctgaagtgcc agtaaagcgc   14340
cggctgctga accccaacc  gttccgccag tttgcgtgtc gtcagaccgt ctacgccgac   14400
ctcgttcaac aggtccaggg cggcacggat cactgtattc ggctgcaact tgtcatgct    14460 tgacacttta tcactgataa acataatatg tccaccaact tatcagtgat aaagaatccg   14520
cgcgttcaat cggaccagcg gaggctggtc cggaggccag acgtgaaacc caacataccc   14580
ctgatcgtaa ttctgagcac tgtcgcgctc gacgctgtcg gcatcggcct gattatgccg   14640
gtgctgccgg gcctcctgcg cgatctggtt cactcgaacg acgtcaccgc ccactatggc   14700
attctgctgg cgctgtatgc gttggtgcaa tttgcctgcg cacctgtgct gggcgcgctg   14760
tcggatcgtt tcgggcggcg gccaatcttg ctcgtctcgc tggccggcgc cactgtcgac   14820
tacgccatca tggcgacagc gccttttcctt tgggttctct atatcgggcg gatcgtggcc   14880
ggcatcaccg gggcgactgg ggcggtagcc ggcgcttata ttgccgatat cactgatggc   14940
gatgagcgcg cgcggcactt cggcttcatg agcgcctgtt tcgggttcgg gatggtcgcg   15000
ggacctgtgc tcggtgggct gatgggcggt ttctccccc  acgctccgtt cttcgccgcg   15060
gcagccttga acggcctcaa tttcctgacg ggctgtttcc ttttgccgga gtcgcacaaa   15120
ggcgaacgcc ggccgttacg cccgggaggct ctcaacccgc tcgcttcgtt ccggtgggcc   15180
cggggcatga ccgtcgtcgc cgccctgatg gcggtcttct tcatcatgca acttgtcgga   15240
```

```
caggtgccgg ccgcgctttg ggtcattttc ggcgaggatc gctttcactg ggacgcgacc   15300
acgatcggca tttcgcttgc cgcatttggc attctgcatt cactcgccca ggcaatgatc   15360
accggccctg tagccgcccg gctcggcgaa aggcgggcac tcatgctcgg aatgattgcc   15420
gacggcacag gctacatcct gcttgccttc gcgacacggg gatggatggc gttcccgatc   15480
atggtcctgc ttgcttcggg tggcatcgga atgccggcgc tgcaagcaat gttgtccagg   15540
caggtggatg aggaacgtca ggggcagctg caaggctcac tggcggcgct caccagcctg   15600
acctcgatcg tcggaccect cctcttcacg gcgatctatg cggcttctat aacaacgtgg   15660
aacgggtggg catggattgc aggcgctgcc ctctacttgc tctgcctgcc ggcgctgcgt   15720
cgcgggcttt ggagcggcgc agggcaacga gccgatcgct gatcgtggaa acgataggcc   15780
tatgccatgc gggtcaaggc gacttccggc aagctatacg cgccctagga gtgcggttgg   15840
aacgttggcc cagccagata ctcccgatca cgagcaggac gccgatgatt tgaagcgcac   15900
tcagcgtctg atccaagaac aaccatccta gcaacacggc ggtccccggg ctgagaaagc   15960
ccagtaagga aacaactgta ggttcgagtc gcgagatccc ccggaaccaa aggaagtagg   16020
ttaaacccgc tccgatcagg ccgagccacg ccaggccgag aacattggtt cctgtaggca   16080
tcgggattgg cggatcaaac actaaagcta ctggaacgag cagaagtcct ccggccgcca   16140
gttgccaggc ggtaaaggtg agcagaggca cgggaggttg ccacttgcgg gtcagcacgg   16200
ttccgaacgc catggaaacc gccccgcca ggcccgctgc gacgccgaca ggatctagcg   16260
ctgcgtttgg tgtcaacacc aacagcgcca cgcccgcagt tccgcaaata gcccccagga   16320
ccgccatcaa tcgtatcggg ctacctagca gagcggcaga gatgaacacg accatcagcg   16380
gctgcacagc gcctaccgtc gccgcgaccc cgcccggcag gcggtagacc gaaataaaca   16440
acaagctcca gaatagcgaa atattaagtg cgccgaggat gaagatgcgc atccaccaga   16500
ttcccgttgg aatctgtcgg acgatcatca cgagcaataa acccgccggc aacgcccgca   16560
gcagcatacc ggcgaccect cggcctcgct gttcgggctc cacgaaaacg ccggacagat   16620
gcgccttgtg agcgtccttg gggccgtcct cctgtttgaa gaccgacagc ccaatgatct   16680
cgccgtcgat gtaggcgccg aatgccacgg catctcgcaa ccgttcagcg aacgcctcca   16740
tgggcttttt ctcctcgtgc tcgtaaacgg acccgaacat ctctggagct ttcttcaggg   16800
ccgacaatcg gatctcgcgg aaatcctgca cgtcggccgc tccaagccgt cgaatctgag   16860
ccttaatcac aattgtcaat tttaatcctc tgtttatcgg cagttcgtag agcgcgccgt   16920
gcgtcccgag cgatactgag cgaagcaagt gcgtcgagca gtgcccgctt gttcctgaaa   16980
tgccagtaaa gcgctggctg ctgaaccccc agccggaact gaccccacaa ggccctagcg   17040
tttgcaatgc accaggtcat cattgaccca ggcgtgttcc accaggccgc tgcctcgcaa   17100
ctcttcgcag gcttcgccga cctgctcgcg ccacttcttc acgcgggtgg aatccgatcc   17160
gcacatgagg cggaaggttt ccagcttgag cgggtacggc tcccggtgcg agctgaaata   17220
gtcgaacatc cgtcgggccg tcggcgacag cttgcggtac ttctcccata tgaatttcgt   17280
gtagtggtcg ccagcaaaca gcacgacgat ttcctcgtcg atcaggacct ggcaacggga   17340
cgttttcttg ccacggtcca ggacgcgaa gcggtgcagc agcgacaccg attccaggtg   17400
cccaacgcgg tcggacgtga agcccatcgc cgtcgcctgt aggcgcgaca ggcattcctc   17460
ggccttcgtg taataccggc cattgatcga ccagccagg tcctggcaaa gctcgtagaa   17520
cgtgaaggtg atcggctcgc cgatagggt gcgcttcgcg tactccaaca cctgctgcca   17580
caccagttcg tcatcgtcgg cccgcagctc gacgccggtg taggtgatct tcacgtcctt   17640
```

```
gttgacgtgg aaaatgacct tgttttgcag cgcctcgcgc gggatttttct tgttgcgcgt    17700
ggtgaacagg gcagagcggg ccgtgtcgtt tggcatcgct cgcatcgtgt ccggccacgg    17760
cgcaatatcg aacaaggaaa gctgcatttc cttgatctgc tgcttcgtgt gtttcagcaa    17820
cgcggcctgc ttggcctcgc tgacctgttt tgccaggtcc tcgccggcgg ttttttcgctt   17880
cttggtcgtc atagttcctc gcgtgtcgat ggtcatcgac ttcgccaaac ctgccgcctc    17940
ctgttcgaga cgacgcgaac gctccacggc ggccgatggc gcgggcaggg caggggagc     18000
cagttgcacg ctgtcgcgct cgatcttggc cgtagcttgc tggaccatcg agccgacgga    18060
ctggaaggtt tcgcggggcg cacgcatgac ggtgcggctt gcgatggttt cggcatcctc    18120
ggcggaaaac cccgcgtcga tcagttcttg cctgtatgcc ttccggtcaa acgtccgatt    18180
cattcaccct ccttgcggga ttgccccgac tcacgccggg gcaatgtgcc cttattcctg    18240
atttgacccg cctggtgcct tggtgtccag ataatccacc ttatcggcaa tgaagtcggt    18300
cccgtagacc gtctggccgt ccttctcgta cttggtattc cgaatcttgc cctgcacgaa    18360
taccagcgac cccttgccca aatacttgcc gtgggcctcg gcctgagagc caaaacactt    18420
gatgcggaag aagtcggtgc gctcctgctt gtcgccggca tcgttgcgcc actcttcatt    18480
aaccgctata tcgaaaattg cttgcggctt gttagaattg ccatgacgta cctcggtgtc    18540
acgggtaaga ttaccgataa actgaactg attatggctc atatcgaaag tctccttgag    18600
aaaggagact ctagtttagc taaacattgg ttccgctgtc aagaacttta gcggctaaaa    18660
ttttgcgggc cgcgaccaaa ggtgcgaggg gcggcttccg ctgtgtacaa ccagatattt    18720
ttcaccaaca tccttcgtct gctcgatgag cggggcatga cgaaacatga gctgtcggag    18780
agggcagggg tttcaatttc gtttttatca gacttaacca acggtaaggc caaccccctcg   18840
ttgaaggtga tggaggccat tgccgacgcc ctggaaactc ccctacctct tctcctggag    18900
tccaccgacc ttgaccgcga ggcactcgcg gagattgcgg gtcatccttt caagagcagc    18960
gtgccgcccg gatacgaacg catcagtgtg gttttgccgt cacataaggc gtttatcgta    19020
aagaaatggg gcgacgacac ccgaaaaaag ctgcgtggaa ggctctgacg ccaagggtta    19080
gggcttgcac ttccttcttt agccgctaaa acggccccctt ctctgcgggc cgtcggctcg   19140
cgcatcatat cgacatcctc aacggaagcc gtgccgcgaa tggcatcggg cgggtgcgct    19200
ttgacagttg ttttctatca gaacccctac gtcgtgcggt tcgattagct gttttgtcttg   19260
caggctaaac actttcggta tatcgtttgc ctgtgcgata atgttgctaa tgatttgttg    19320
cgtaggggtt actgaaaagt gagcgggaaa gaagagtttc agaccatcaa ggagcgggcc    19380
aagcgcaagc tggaacgcga catgggtgcg gacctgttgg ccgcgctcaa cgacccgaaa    19440
accgttgaag tcatgctcaa cgcggacggc aaggtgtggc acgaacgcct tggcgagccg    19500
atgcggtaca tctgcgacat gcggcccagc cagtcgcagg cgattataga aacggtggcc    19560
ggattccacg gcaaagaggt cacgcggcat tcgcccatcc tggaaggcga gttccccttg    19620
gatggcagcc gctttgccgg ccaattgccg ccggtcgtgg ccgcgccaac ctttgcgatc    19680
cgcaagcgcg cggtcgccat cttcacgctg gaacagtacg tcgaggcggg catcatgacc    19740
cgcgagcaat acgaggtcat taaaagcgcc gtcgcggcgc atcgaaacat cctcgtcatt    19800
ggcggtactg gctcgggcaa gaccacgctc gtcaacgcga tcatcaatga aatggtcgcc    19860
ttcaacccgt ctgagcgcgt cgtcatcatc gaggacaccg gcgaaatcca gtgcgccgca    19920
gagaacgccg tccaatacca caccagcatc gacgtctcga tgacgctgct gctcaagaca    19980
```

```
acgctgcgta tgcgccccga ccgcatcctg gtcggtgagg tacgtggccc cgaagccctt   20040
gatctgttga tggcctggaa caccgggcat gaaggaggtg ccgccaccct gcacgcaaac   20100
aaccccaaag cgggcctgag ccggctcgcc atgcttatca gcatgcaccc ggattcaccg   20160
aaacccattg agccgctgat tggcgaggcg gttcatgtgg tcgtccatat cgccaggacc   20220
cctagcggcc gtcgagtgca agaaattctc gaagttcttg gttacgagaa cggccagtac   20280
atcaccaaaa ccctgtaagg agtatttcca atgacaacgg ctgttccgtt ccgtctgacc   20340
atgaatcgcg gcattttgtt ctaccttgcc gtgttcttcg ttctcgctct cgcgttatcc   20400
gcgcatccgg cgatggcctc ggaaggcacc ggcggcagct tgccatatga gagctggctg   20460
acgaacctgc gcaactccgt aaccggcccg gtggccttcg cgctgtccat catcggcatc   20520
gtcgtcgccg gcggcgtgct gatcttcggc ggcgaactca acgccttctt ccgaaccctg   20580
atcttcctgg ttctggtgat ggcgctgctg gtcggcgcgc agaacgtgat gagcaccttc   20640
ttcggtcgtg gtgccgaaat cgcggccctc ggcaacgggg cgctgcacca ggtgcaagtc   20700
gcggcggcgg atgccgtgcg tgcggtagcg gctggacggc tcgcctaatc atggctctgc   20760
gcacgatccc catccgtcgc gcaggcaacc gagaaaacct gttcatgggt ggtgatcgtg   20820
aactggtgat gttctcgggc ctgatggcgt ttgcgctgat tttcagcgcc caagagctgc   20880
gggccaccgt ggtcggtctg atcctgtggt tcggggcgct ctatgcgttc gaatcatgg    20940 cgaaggccga tccgaagatg cggttcgtgt acctgcgtca ccgccggtac aagccgtatt   21000
acccggcccg ctcgaccccg ttccgcgaga acaccaatag ccaagggaag caataccgat   21060
gatccaagca attgcgattg caatcgcggg cctcggcgcg cttctgttgt tcatcctctt   21120
tgcccgcatc cgcgcggtcg atgccgaact gaaactgaaa aagcatcgtt ccaaggacgc   21180
cggcctggcc gatctgctca actacgccgc tgtcgtcgat gacggcgtaa tcgtgggcaa   21240
gaacggcagc tttatggctg cctggctgta caagggcgat gacaacgcaa gcagcaccga   21300
ccagcagcgc gaagtagtgt ccgcccgcat caaccaggcc ctcgcgggcc tgggaagtgg   21360
gtggatgatc catgtggacg ccgtgcggcg tcctgctccg aactacgcgg agcggggcct   21420
gtcggcgttc cctgaccgtc tgacggcagc gattgaagaa gagcgctcgg tcttgccttg   21480
ctcgtcggtg atgtacttca ccagctccgc gaagtcgctc ttcttgatgg agcgcatggg   21540
gacgtgcttg gcaatcacgc gcaccccccg gccgttttag cggctaaaaa agtcatggct   21600
ctgccctcgg gcggaccacg cccatcatga ccttgccaag ctcgtcctgc ttctcttcga   21660
tcttcgccag cagggcgagg atcgtggcat caccgaaccg cgccgtgcgc gggtcgtcgg   21720
tgagccagag tttcagcagg ccgcccaggc ggcccaggtc gccattgatg cgggccagct   21780
cgcggacgtg ctcatagtcc acgacgcccg tgattttgta gccctggccg acggccagca   21840
ggtaggccga caggctcatg ccggccgccg ccgccttttc ctcaatcgct cttcgttcgt   21900
ctggaaggca gtacaccttg ataggtgggc tgcccttcct ggttggcttg gtttcatcag   21960
ccatccgctt gccctcatct gttacgccgg cggtagccgg ccagcctcgc agagcaggat   22020
tcccgttgag caccgccagg tgcgaataag ggacagtgaa gaaggaacac ccgctcgcgg   22080
gtgggcctac ttcacctatc ctgcccggct gacgccgttg gataccaccaa ggaaagtcta   22140 cacgaaccct ttggcaaaat cctgtatatc gtgcgaaaaa ggatggatat accgaaaaaa   22200
tcgctataat gaccccgaag cagggttatg cagcggaaaa gcgctgcttc cctgctgttt   22260
tgtggaatat ctaccgactg gaaacaggca aatgcaggaa attactgaac tgaggggaca   22320
ggcgagagac gatgccaaag agctacaccg acgagctggc cgagtgggtt gaatcccgcg   22380
```

```
cggccaagaa gcgccggcgt gatgaggctg cggttgcgtt cctggcggtg agggcggatg  22440
tcgaggcggc gttagcgtcc ggctatgcgc tcgtcaccat ttgggagcac atgcgggaaa  22500
cggggaaggt caagttctcc tacgagacgt tccgctcgca cgccaggcgg cacatcaagg  22560
ccaagcccgc cgatgtgccc gcaccgcagg ccaaggctgc ggaacccgcg ccggcaccca  22620
agacgccgga gccacggcgg ccgaagcagg ggggcaaggc tgaaaagccg gcccccgctg  22680 cggcccccgac cggcttcacc ttcaacccaa caccggacaa aaaggatcta ctgtaatggc  22740
gaaaattcac atggttttgc agggcaaggg cggggtcggc aagtcggcca tcgccgcgat  22800
cattgcgcag tacaagatgg acaagggggca gacacccttg tgcatcgaca ccgacccggt  22860
gaacgcgacg ttcgagggct acaaggccct gaacgtccgc cggctgaaca tcatggccgg  22920
cgacgaaatt aactcgcgca acttcgacac cctggtcgag ctgattgcgc cgaccaagga  22980
tgacgtggtg atcgacaacg gtgccagctc gttcgtgcct ctgtcgcatt acctcatcag  23040
caaccaggtg ccggctctgc tgcaagaaat ggggcatgag ctggtcatcc ataccgtcgt  23100
caccggcggc caggctctcc tggacacggt gagcggcttc gcccagctcg ccagccagtt  23160
cccggccgaa gcgcttttcg tggtctggct gaacccgtat tgggggccta tcgagcatga  23220
gggcaagagc tttgagcaga tgaaggcgta cacggccaac aaggcccgcg tgtcgtccat  23280
catccagatt ccgccctca aggaagaaac ctacggccgc gatttcagcg acatgctgca  23340
agagcggctg acgttcgacc aggcgctggc cgatgaatcg ctcacgatca tgacgcggca  23400
acgcctcaag atcgtgcggc gcggcctgtt tgaacagctc gacgcggcgg ccgtgctatg  23460
agcgaccaga ttgaagagct gatccgggag attgcggcca agcacggcat cgccgtcggc  23520
cgcgacgacc cggtgctgat cctgcatacc atcaacgccc ggctcatggc cgacagtgcg  23580
gccaagcaag aggaaatcct tgccgcgttc aaggaagagc tggaagggat cgcccatcgt  23640
tggggcgagg acgccaaggc caaagcggag cggatgctga acgcggccct ggcggccagc  23700
aaggacgcaa tggcgaaggt aatgaaggac agcgccgcgc aggcggccga agcgatccgc  23760
agggaaatcg acgacggcct tggccgccag ctcgcggcca aggtcgcgga cgcgcggcgc  23820
gtggcgatga tgaacatgat cgccggcggc atggtgttgt tcgcggccgc cctggtggtg  23880
tgggcctcgt tatgaatcgc agaggcgcag atgaaaaagc ccggcgttgc cgggctttgt  23940
ttttgcgtta gctgggcttg tttgacaggc ccaagctctg actgcgcccg cgctcgcgct  24000
cctgggcctg tttcttctcc tgctcctgct tgcgcatcag ggcctggtgc cgtcgggctg  24060
cttcacgcat cgaatcccag tcgccggcca gctcggatg ctccgcgcgc atcttgcgcg  24120
tcgccagttc ctcgatcttg ggcgcgtgaa tgcccatgcc ttccttgatt tcgcgcacca  24180
tgtccagccg cgtgtgcagg gtctgcaagc gggcttgctg ttgggcctgc tgctgctgcc  24240
aggcggcctt tgtacgcggc agggacagca agccgggggc attggactgt agctgctgca  24300
aacgcgcctg ctgacggtct acgagctgtt ctagccggtc ctcgatgcgc tccacctggt  24360
catgctttgc ctgcacgtag agcgcaaggg tctgctggta ggtctgctcg atgggcgcgg  24420
attctaagag ggcctgctgt tccgtctcgg cctcctgggc cgcctgtagc aaatcctcgc  24480
cgctgttgcc gctggactgc tttactgccg gggactgctg ttgccctgct cgcgccgtcg  24540
tcgcagttcg gcttgccccc actcgattga ctgcttcatt tcgagccgca gcgatgcgat  24600
ctcggattgc gtcaacggac ggggcagcgc ggaggtgtcc ggcttctcct tgggtgagtc  24660
ggtcgatgcc atagccaaag gtttccttcc aaaatgcgtc cattgctgga ccgtgtttct  24720
```

```
cattgatgcc cgcaagcatc ttcggcttga ccgccaggtc aagcgcgcct tcatgggcgg   24780
tcatgacgga cgccgccatg accttgccgc cgttgttctc gatgtagccg cgtaatgagg   24840
caatggtgcc gcccatcgtc agcgtgtcat cgacaacgat gtacttctgg ccgggatca   24900 cctccccctc gaaagtcggg ttgaacgcca ggcgatgatc tgaaccggct ccggttcggg   24960
cgaccttctc ccgctgcaca atgtccgttt cgacctcaag gccaaggcgg tcggccagaa   25020
cgaccgccat catggccgga atcttgttgt tccccgccgc ctcgacggcg aggactggaa   25080
cgatgcgggg cttgtcgtcg ccgatcagcg tcttgagctg ggcaacagtg tcgtccgaaa   25140
tcaggcgctc gaccaaatta agcgccgctt ccgcgtcgcc ctgcttcgca gcctggtatt   25200
caggctcgtt ggtcaaagaa ccaaggtcgc cgttgcgaac caccttcggg aagtctcccc   25260
acggtgcgcg ctcggctctg ctgtagctgc tcaagacgcc tcccttttta gccgctaaaa   25320
ctctaacgag tgcgcccgcg actcaacttg acgctttcgg cacttacctg tgccttgcca   25380
cttgcgtcat aggtgatgct tttcgcactc ccgatttcag gtactttatc gaaatctgac   25440
cgggcgtgca ttacaaagtt cttccccacc tgttggtaaa tgctgccgct atctgcgtgg   25500
acgatgctgc cgtcgtggcg ctgcgactta tcggccttt gggccatata gatgttgtaa   25560
atgccaggtt tcagggcccc ggctttatct accttctggt tcgtccatgc gccttggttc   25620
tcggtctgga caattctttg cccattcatg accaggaggc ggtgtttcat tgggtgactc   25680
ctgacggttg cctctggtgt taaacgtgtc ctggtcgctt ccggctaaa aaaaagccga   25740 cctcggcagt tcgaggccgg ctttccctag agccgggcgc gtcaaggttg ttccatctat   25800
tttagtgaac tgcgttcgat ttatcagtta ctttcctccc gctttgtgtt tcctcccact   25860
cgtttccgcg tctagccgac ccctcaacat agcggcctct tcttgggctg cctttgcctc   25920
ttgccgcgct tcgtcacgct cggcttgcac cgtcgtaaag cgctcggcct gcctggccgc   25980
ctcttgcgcc gccaacttcc tttgctcctg gtgggcctcg gcgtcggcct gcgccttcgc   26040
tttcaccgct gccaactccg tgcgcaaact ctccgcttcg cgcctggtgg cgtcgcgctc   26100
gccgcgaagc gcctgcattt cctggttggc cgcgtccagg gtcttgcggc tctcttcttt   26160
gaatgcgcgg gcgtcctggt gagcgtagtc cagctcggcg cgcagctcct gcgctcgacg   26220
ctccacctcg tcggcccgct gcgtcgccag cgcggcccgc tgctcggctc ctgccagggc   26280
ggtgcgtgct tcgccagggg cttgccgctg cgtgcggcc agctcggccg cctcggcggc   26340
ctgctgctct agcaatgtaa cgcgcgcctg ggcttcttcc agctcgcggg cctgcgcctc   26400
gaaggcgtcg gccagctccc cgcgcacggc ttccaactcg ttgcgctcac gatcccagcc   26460
ggcttgcgct gcctgcaacg attcattggc aagggcctgg gcggcttgcc agagggcggc   26520
cacgccctgg ttgccggcct gctgcaccgc gtccggcacc tggactgcca gcggggcggc   26580
ctgcgccgtg cgctggcgtc gccattcgcg catgccggcg ctggcgtcgt tcatgttgac   26640
gcgggcggcc ttacgcactg catccacggt cgggaagttc tcccggtcgc cttgctcgaa   26700
cagctcgtcc gcagccgcaa aaatgcggtc gcgcgtctct ttgttcagtt ccatgttggc   26760
tccggtaatt ggtaagaata ataatactct tacctacctt atcagcgcaa gagtttagct   26820
gaacagttct cgacttaacg gcaggttttt tagcggctga agggcaggca aaaaaagccc   26880
cgcacggtcg gcgggggcaa agggtcagcg ggaagggat tagcgggcgt cgggcttctt   26940
catgcgtcgg ggccgcgctt cttgggatgg agcacgacga agcgcgcacg cgcatcgtcc   27000
tcggccctat cggcccgcgt cgcggtcagg aacttgtcgc gcgctaggtc ctccctggtg   27060
ggcaccaggg gcatgaactc ggcctgctcg atgtaggtcc actccatgac cgcatcgcag   27120
```

```
tcgaggccgc gttccttcac cgtctcttgc aggtcgcggt acgcccgctc gttgagcggc  27180
tggtaacggg ccaattggtc gtaaatggct gtcggccatg agcggccttt cctgttgagc  27240
cagcagccga cgacgaagcc ggcaatgcag gcccctggca caaccaggcc gacgccgggg  27300 gcagggatg gcagcagctc gccaaccagg aaccccgccg cgatgatgcc gatgccggtc  27360
aaccagccct tgaaactatc cggccccgaa acacccctgc gcattgcctg gatgctgcgc  27420
cggatagctt gcaacatcag gagccgtttc ttttgttcgt cagtcatggt ccgccctcac  27480
cagttgttcg tatcggtgtc ggacgaactg aaatcgcaag agctgccggt atcggtccag  27540
ccgctgtccg tgtcgctgct gccgaagcac ggcgagggt ccgcgaacgc cgcagacggc  27600
gtatccggcc gcagcgcatc gcccagcatg gccccggtca gcgagccgcc ggccaggtag  27660
cccagcatgg tgctgttggt cgccccggcc accagggccg acgtgacgaa atcgccgtca  27720
ttccctctgg attgttcgct gctcggcggg gcagtgcgcc gcgccggcgg cgtcgtggat  27780
ggctcgggtt ggctggcctg cgacggccgg cgaaaggtgc gcagcagctc gttatcgacc  27840
ggctgcggcg tcggggccgc cgccttgcgc tgcggtcggt gttccttctt cggctcgcgc  27900
agcttgaaca gcatgatcgc ggaaaccagc agcaacgccg cgcctacgcc tcccgcgatg  27960
tagaacagca tcggattcat tcttcggtcc tccttgtagc ggaaccgttg tctgtgcggc  28020
gcgggtggcc cgcgccgctg tctttgggga tcagccctcg atgagcgcga ccagtttcac  28080
gtcggcaagg ttcgcctcga actcctggcc gtcgtcctcg tacttcaacc aggcatagcc  28140
ttccgccggc ggccgacggt tgaggataag gcgggcaggg cgctcgtcgt gctcgacctg  28200
gacgatggcc ttttttcagct tgtccgggtc cggctccttc gcgcccttttt ccttggcgtc  28260 cttaccgtcc tggtcgccgt cctcgccgtc ctggccgtcg ccggcctccg cgtcacgctc  28320
ggcatcagtc tggccgttga aggcatcgac ggtgttggga tcgcggccct tctcgtccag  28380
gaactcgcgc agcagcttga ccgtgccgcg cgtgatttcc tgggtgtcgt cgtcaagcca  28440
cgcctcgact tcctccgggc gcttcttgaa ggccgtcacc agctcgttca ccacggtcac  28500
gtcgcgcacg cggccggtgt tgaacgcatc ggcgatcttc tccggcaggt ccagcagcgt  28560
gacgtgctgg gtgatgaacg ccggcgactt gccgatttcc ttggcgatat cgcctttctt  28620
cttgcccttc gccagctcgc ggccaatgaa gtcggcaatt tcgcgcgggg tcagctcgtt  28680
gcgttgcagg ttctcgataa cctggtcggc ttcgttgtag tcgttgtcga tgaacgccgg  28740
gatggacttc ttgccggccc acttcgagcc acggtagcgg cgggcgccgt gattgatgat  28800
atagcggccc ggctgctcct ggttctcgcg caccgaaatg ggtgacttca ccccgcgctc  28860
tttgatcgtg gcaccgattt ccgcgatgct ctccgggaa aagccggggt tgtcggccgt  28920
ccgcggctga tgcggatctt cgtcgatcag gtccaggtcc agctcgatag ggccggaacc  28980
gccctgagac gccgcaggag cgtccaggag gctcgacagg tcgccgatgc tatccaaccc  29040
caggccggac ggctgcgccg cgcctgcggc ttcctgagcg gccgcagcgg tgttttcctt  29100
ggtggtcttg gcttgagccg cagtcattgg gaaatctcca tcttcgtgaa cacgtaatca  29160
gccagggcgc gaacctcttt cgatgccttg cgcgcggccg ttttcttgat cttccagacc  29220
ggcacaccgg atgcgagggc atcggcgatg ctgctgcgca ggccaacggt ggccggaatc  29280
atcatcttgg ggtacgcggc cagcagctcg gcttggtggc gcgcgtggcg cggattccgc  29340
gcatcgacct tgctgggcac catgccaagg aattgcagct tggcgttctt ctggcgcacg  29400
ttcgcaatgg tcgtgaccat cttcttgatg ccctggatgc tgtacgcctc aagctcgatg  29460
```

-continued

| | |
|---|---|
| ggggacagca catagtcggc cgcgaagagg gcggccgcca ggccgacgcc aagggtcggg | 29520 |
| gccgtgtcga tcaggcacac gtcgaagcct tggttcgcca gggccttgat gttcgccccg | 29580 |
| aacagctcgc gggcgtcgtc cagcgacagc cgttcggcgt tcgccagtac cgggttggac | 29640 |
| tcgatgaggg cgaggcgcgc ggcctggccg tcgccggctg cgggtgcggt ttcggtccag | 29700 |
| ccgccggcag ggacagcgcc gaacagcttg cttgcatgca ggccggtagc aaagtccttg | 29760 |
| agcgtgtagg acgcattgcc ctgggggtcc aggtcgatca cggcaacccg caagccgcgc | 29820 |
| tcgaaaaagt cgaaggcaag atgcacaagg gtcgaagtct tgccgacgcc gccttctgg | 29880 |
| ttggccgtga ccaaagtttt catcgtttgg tttcctgttt tttcttggcg tccgcttccc | 29940 |
| acttccggac gatgtacgcc tgatgttccg gcagaaccgc cgttacccgc gcgtacccct | 30000 |
| cgggcaagtt cttgtcctcg aacgcggccc acacgcgatg caccgcttgc gacactgcgc | 30060 |
| ccctggtcag tcccagcgac gttgcgaacg tcgcctgtgg cttcccatcg actaagacgc | 30120 |
| cccgcgctat ctcgatggtc tgctgcccca cttccagccc ctggatcgcc tcctggaact | 30180 |
| ggctttcggt aagccgtttc ttcatggata cacccataa tttgctccgc gccttggttg | 30240 |
| aacatagcgg tgacagccgc cagcacatga gagaagttta gctaaacatt tctcgcacgt | 30300 |
| caacacctt agccgctaaa actcgtcctt ggcgtaacaa aacaaagcc cggaaaccgg | 30360 |
| gctttcgtct cttgccgctt atggctctgc acccggctcc atcaccaaca ggtcgcgcac | 30420 |
| gcgcttcact cggttgcgga tcgacactgc cagcccaaca aagccggttg ccgccgcgc | 30480 |
| caggatcgcg ccgatgatgc cggccacacc ggccatcgcc caccaggtcg ccgccttccg | 30540 |
| gttccattcc tgctggtact gcttcgcaat gctggacctc ggctcaccat aggctgaccg | 30600 |
| ctcgatggcg tatgccgctt ctccccttgg cgtaaaaccc agcgccgcag gcggcattgc | 30660 |
| catgctgccc gccgctttcc cgaccacgac gcgcgcacca ggcttgcggt ccagaccttc | 30720 |
| ggccacggcg agctgcgcaa ggacataatc agccgccgac ttggctccac gcgcctcgat | 30780 |
| cagctcttgc actcgcgcga atccttggc ctccacggcc gccatgaatc gcgcacgcgg | 30840 |
| cgaaggctcc gcagggccgg cgtcgtgatc gccgccgaga atgcccttca ccaagttcga | 30900 |
| cgacacgaaa atcatgctga cggctatcac catcatgcag acggatcgca cgaacccgct | 30960 |
| gaattgaaca cgagcacggc acccgcgacc actatgccaa gaatgcccaa ggtaaaaatt | 31020 |
| gccggccccg ccatgaagtc cgtgaatgcc ccgacggccg aagtgaaggg caggccgcca | 31080 |
| cccaggccgc cgccctcact gcccggcacc tggtcgctga atgtcgatgc cagcacctgc | 31140 |
| ggcacgtcaa tgcttccggg cgtcgcgctc gggctgatcg cccatcccgt tactgccccg | 31200 |
| atcccggcaa tggcaaggac tgccagcgct gccatttttg gggtgaggcc gttcgcggcc | 31260 |
| gaggggcgca gccctgggg ggatgggagg cccgcgttag cgggccggga gggttcgaga | 31320 |
| aggggggca ccccccttcg gcgtgcgcgg tcacgcgcac agggcgcagc cctggttaaa | 31380 |
| aacaaggttt ataaatattg gtttaaaagc aggttaaaag acaggttagc ggtggccgaa | 31440 |
| aaacgggcgg aaacccttgc aaatgctgga ttttctgcct gtggacagcc cctcaaatgt | 31500 |
| caataggtgc gcccctcatc tgtcagcact ctgcccctca agtgtcaagg atcgcgcccc | 31560 |
| tcatctgtca gtagtcgcgc ccctcaagtg tcaataccgc agggcactta tcccaggct | 31620 |
| tgtccacatc atctgtggga aactcgcgta aaatcaggcg ttttcgccga tttgcgaggc | 31680 |
| tggccagctc cacgtcgccg gccgaaatcg agcctgcccc tcatctgtca acgccgcgcc | 31740 |
| gggtgagtcg gcccctcaag tgtcaacgtc cgccctcat ctgtcagtga ggccaagtt | 31800 |
| ttccgcgagg tatccacaac gccggcggcc gcggtgtctc gcacacggct tcgacggcgt | 31860 |

```
ttctggcgcg tttgcagggc catagacggc cgccagccca gcggcgaggg caaccagccc  31920
ggtgagcgtc ggaaaggcgc tggaagcccc gtagcgacgc ggagagggc gagacaagcc   31980 aagggcgcag gctcgatgcg cagcacgaca tagccggttc tcgcaaggac gagaatttcc  32040
ctgcggtgcc cctcaagtgt caatgaaagt ttccaacgcg agccattcgc gagagccttg  32100
agtccacgct agatgagagc tttgttgtag gtggaccagt tggtgatttt gaacttttgc  32160
tttgccacgg aacggtctgc gttgtcggga agatgcgtga tctgatcctt caactcagca  32220
aaagttcgat ttattcaaca aagccacgtt gtgtctcaaa atctctgatg ttacattgca  32280
caagataaaa atatatcatc atgaacaata aaactgtctg cttacataaa cagtaataca  32340
aggggtgtta tgagccatat tcaacgggaa acgtcttgct cgactctaga gctcgttcct  32400
cgaggcctcg aggcctcgag gaacggtacc tgcggggaag cttacaataa tgtgtgttgt  32460
taagtcttgt tgcctgtcat cgtctgactg actttcgtca taaatcccgg cctccgtaac  32520
ccagctttgg gcaagctcac ggatttgatc cggcggaacg ggaatatcga gatgccgggc  32580
tgaacgctgc agttccagct ttcccttcg ggacaggtac tccagctgat tgattatctg    32640
ctgaagggtc ttggttccac ctcctggcac aatgcgaatg attacttgag cgcgatcggg  32700
catccaattt tctcccgtca ggtgcgtggt caagtgctac aaggcacctt tcagtaacga  32760
gcgaccgtcg atccgtcgcc gggatacgga caaaatggag cgcagtagtc catcgagggc  32820
ggcgaaagcc tcgccaaaag caatacgttc atctcgcaca gcctccagat ccgatcgagg  32880
gtcttcggcg taggcagata gaagcatgga tacattgctt gagagtattc cgatggactg  32940
aagtatggct tccatctttt ctcgtgtgtc tgcatctatt tcgagaaagc ccccgatgcg  33000
gcgcaccgca acgcgaattg ccatactatc cgaaagtccc agcaggcgcg cttgatagga  33060
aaaggtttca tactcggccg atcgcagacg ggcactcacg accttgaacc cttcaacttt  33120
cagggatcga tgctggttga tggtagtctc actcgacgtg gctctggtgt gttttgacat  33180
agcttcctcc aaagaaagcg gaaggtctgg atactccagc acgaaatgtg cccgggtaga  33240
cggatggaag tctagccctg ctcaatatga aatcaacagt acatttacag tcaatactga  33300
atatacttgc tacatttgca attgtcttat aacgaatgtg aaataaaaat agtgtaacaa  33360
cgcttttact catcgataat cacaaaaaca tttatacgaa caaaaataca aatgcactcc  33420
ggtttcacag gataggcggg atcagaatat gcaacttttg acgttttgtt ctttcaaagg  33480
gggtgctggc aaaaccaccg cactcatggg cctttgcgct gctttggcaa atgacggtaa  33540
acgagtggcc ctctttgatg ccgacgaaaa ccggcctctg acgcgatgga gagaaaacgc  33600
cttacaaagc agtactggga tcctcgctgt gaagtctatt ccgccgacga aatgccccctt  33660 cttgaagcag cctatgaaaa tgccgagctc gaaggatttg attatgcgtt ggccgatacg  33720
cgtggcggct cgagcgagct caacaacaca atcatcgcta gctcaaacct gcttctgatc  33780
cccaccatgc taacgccgct cgacatcgat gaggcactat ctacctaccg ctacgtcatc  33840
gagctgctgt tgagtgaaaa tttggcaatt cctacagctg ttttgcgcca acgcgtcccg  33900
gtcggccgat tgacaacatc gcaacgcagg atgtcagaga cgctagagag ccttccagtt  33960
gtaccgtctc ccatgcatga aagagatgca tttgccgcga tgaaagaacg cggcatgttg  34020
catcttacat tactaaacac gggaactgat ccgacgatgc gcctcataga gaggaatctt  34080
cggattgcga tggaggaagt cgtggtcatt tcgaaactga tcagcaaaat cttggaggct  34140
tgaagatggc aattcgcaag cccgcattgt cggtcggcga agcacggcgg cttgctggtg  34200
```

```
ctcgacccga gatccaccat cccaacccga cacttgttcc ccagaagctg gacctccagc    34260
acttgcctga aaaagccgac gagaaagacc agcaacgtga gcctctcgtc gccgatcaca    34320
tttacagtcc cgatcgacaa cttaagctaa ctgtggatgc ccttagtcca cctccgtccc    34380
cgaaaaagct ccaggttttt ctttcagcgc gaccgcccgc gcctcaagtg tcgaaaacat    34440
atgacaacct cgttcggcaa tacagtccct cgaagtcgct acaaatgatt ttaaggcgcg    34500
cgttggacga tttcgaaagc atgctggcag atggatcatt tcgcgtggcc ccgaaaagtt    34560
atccgatccc ttcaactaca gaaaaatccg ttctcgttca gacctcacgc atgttcccgg    34620
ttgcgttgct cgaggtcgct cgaagtcatt ttgatccgtt ggggttggag accgctcgag    34680
ctttcggcca caagctggct accgccgcgc tcgcgtcatt ctttgctgga gagaagccat    34740
cgagcaattg gtgaagaggg acctatcgga acccctcacc aaatattgag tgtaggtttg    34800
aggccgctgg ccgcgtcctc agtcacctt tgagccagat aattaagagc caaatgcaat     34860
tggctcaggc tgccatcgtc ccccgtgcg aaacctgcac gtccgcgtca aagaaataac      34920
cggcacctct tgctgttttt atcagttgag ggcttgacgg atccgcctca gtttgcggc     34980 gcagccgcaa aatgagaaca tctatactcc tgtcgtaaac ctcctcgtcg cgtactcgac    35040
tggcaatgag aagttgctcg cgcgatagaa cgtcgcgggg tttctctaaa aacgcgagga    35100
gaagattgaa ctcacctgcc gtaagtttca cctcaccgcc agcttcggac atcaagcgac    35160
gttgcctgag attaagtgtc cagtcagtaa acaaaaaga ccgtcggtct ttggagcgga     35220
caacgttggg gcgcacgcgc aaggcaaccc gaatgcgtgc aagaaactct ctcgtactaa    35280
acggcttagc gataaaatca cttgctccta gctcgagtgc aacaacttta tccgtctcct    35340
caaggcggtc gccactgata attatgattg gaatatcaga cttgtccgcc agatttcgaa    35400
cgatctcaag cccatcttca cgacctaaat ttagatcaac aaccacgaca tcgaccgtcg    35460
cggaagagag tactctagtg aactgggtgc tgtcggctac cgcggtcact ttgaaggcgt    35520
ggatcgtaag gtattcgata ataagatgcc gcatagcgac atcgtcatcg ataagaagaa    35580
cgtgtttcaa cggctcacct ttcaatctaa aatctgaacc cttgttcaca gcgcttgaga    35640
aattttcacg tgaaggatgt acaatcatct ccagctaaat gggcagttcg tcagaattgc    35700
ggctgaccgc ggatgacgaa aatgcgaacc aagtatttca atttatgac aaaagttctc     35760 aatcgttgtt acaagtgaaa cgcttcgagg ttacagctac tattgattaa ggagatcgcc    35820
tatggtctcg ccccggcgtc gtgcgtccgc cgcgagccag atctcgccta cttcataaac    35880
gtcctcatag gcacggaatg gaatgatgac atcgatcgcc gtagagagca tgtcaatcag    35940
tgtgcgatct tccaagctag caccttgggc gctacttttg acaagggaaa acagtttctt    36000
gaatccttgg attggattcg cgccgtgtat tgttgaaatc gatcccggat gtcccgagac    36060
gacttcactc agataagccc atgctgcatc gtcgcgcatc tcgccaagca atatccggtc    36120
cggccgcata cgcagacttg cttggagcaa gtgctcggcg ctcacagcac ccagcccagc    36180
accgttcttg gagtagagta gtctaacatg attatcgtgt ggaatgacga gttcgagcgt    36240
atcttctatg gtgattagcc tttcctgggg ggggatggcg ctgatcaagg tcttgctcat    36300
tgttgtcttg ccgcttccgg tagggccaca tagcaacatc gtcagtcggc tgacgacgca    36360
tgcgtgcaga aacgcttcca aatccccgtt gtcaaaatgc tgaaggatag cttcatcatc    36420
ctgattttgg cgtttccttc gtgtctgcca ctggttccac ctcgaagcat cataacggga    36480
ggagacttct ttaagaccag aaacacgcga gcttggccgt cgaatggtca agctgacggt    36540
gcccgaggga acggtcggcg gcagacagat ttgtagtcgt tcaccaccag gaagttcagt    36600
```

```
ggcgcagagg gggttacgtg gtccgacatc ctgctttctc agcgcgcccg ctaaaatagc   36660
gatatcttca agatcatcat aagagacggg caaaggcatt ttggtaaaaa tgccggcttg   36720
gcgcacaaat gcctctccag gtcgattgat cgcaatttct tcagtcttcg ggtcatcgag   36780
ccattccaaa atcggcttca gaagaaagcg tagttgcgga tccacttcca tttacaatgt   36840
atcctatctc taagcggaaa tttgaattca ttaagagcgg cggttcctcc ccgcgtggc    36900 gccgccagtc aggcggagct ggtaaacacc aaagaaatcg aggtcccgtg ctacgaaaat   36960
ggaaacggtg tcaccctgat tcttcttcag ggttggcggt atgttgatgg ttgccttaag   37020
ggctgtctca gttgtctgct caccgttatt ttgaaagctg ttgaagctca tcccgccacc   37080
cgagctgccg gcgtaggtgc tagctgcctg gaaggcgcct tgaacaacac tcaagagcat   37140
agctccgcta aaacgctgcc agaagtggct gtcgaccgag cccggcaatc ctgagcgacc   37200
gagttcgtcc gcgcttggcg atgttaacga gatcatcgca tggtcaggtg tctcggcgcg   37260
atcccacaac acaaaaacgc gcccatctcc ctgttgcaag ccacgctgta tttcgccaac   37320
aacggtggtg ccacgatcaa gaagcacgat attgttcgtt gttccacgaa tatcctgagg   37380
caagacacac tttacatagc ctgccaaatt tgtgtcgatt gcggtttgca agatgcacgg   37440
aattattgtc ccttgcgtta ccataaaatc ggggtgcggc aagagcgtgg cgctgctggg   37500
ctgcagctcg gtgggtttca tacgtatcga caaatcgttc tcgccggaca cttcgccatt   37560
cggcaaggag ttgtcgtcac gcttgccttc ttgtcttcgg cccgtgtcgc cctgaatggc   37620
gcgtttgctg accccttgat cgccgctgct atatgcaaaa atcggtgttt cttccggccg   37680
tggctcatgc cgctccggtt cgcccctcgg cggtagagga gcagcaggct gaacagcctc   37740
ttgaaccgct ggaggatccg gcggcacctc aatcggagct ggatgaaatg gcttggtgtt   37800
tgttgcgatc aaagttgacg gcgatgcgtt ctcattcacc ttcttttggc gcccacctag   37860
ccaaatgagg cttaatgata acgcgagaac gacacctccg acgatcaatt tctgagaccc   37920
cgaaagacgc cggcgatgtt tgtcggagac cagggatcca gatgcatcaa cctcatgtgc   37980
cgcttgctga ctatcgttat tcatcccttc gcccccttca ggacgcgttt cacatcgggc   38040
ctcaccgtgc ccgtttgcgg ccttttggcca acgggatcgt aagcggtgtt ccagatacat   38100
agtactgtgt ggccatccct cagacgccaa cctcgggaaa ccgaagaaat ctcgacatcg   38160 ctcccttta ctgaatagtt ggcaacagct tccttgccat caggattgat ggtgtagatg     38220
gagggtatgc gtacattgcc cggaaagtgg aataccgtcg taaatccatt gtcgaagact   38280
tcgagtggca acagcgaacg atcgccttgg gcgacgtagt gccaattact gtccgccgca   38340
ccaagggctg tgacaggctg atccaataaa ttctcagctt tccgttgata ttgtgcttcc   38400
gcgtgtagtc tgtccacaac agccttctgt tgtgcctccc ttcgccgagc cgccgcatcg   38460
tcggcggggt aggcgaattg gacgctgtaa tagagatcgg gctgctcttt atcgaggtgg   38520
gacagagtct tggaacttat actgaaaaca taacggcgca tcccggagtc gcttgcggtt   38580
agcacgatta ctggctgagg cgtgaggacc tggcttgcct tgaaaaatag ataatttccc   38640
cgcggtaggg ctgctagatc tttgctattt gaaacggcaa ccgctgtcac cgtttcgttc   38700
gtggcgaatg ttacgaccaa agtagctcca accgccgtcg agaggcgcac cacttgatcg   38760
ggattgtaag ccaaataacg catgcgcgga tctagcttgc ccgccattgg agtgtcttca   38820
gcctccgcac cagtcgcagc ggcaaataaa catgctaaaa tgaaagtgc ttttctgatc    38880 atggttcgct gtggcctacg tttgaaacgg tatcttccga tgtctgatag gaggtgacaa   38940
```

```
ccagacctgc cgggttggtt agtctcaatc tgccgggcaa gctggtcacc ttttcgtagc    39000
gaactgtcgc ggtccacgta ctcaccacag gcattttgcc gtcaacgacg agggtccttt    39060
tatagcgaat ttgctgcgtg cttggagtta catcatttga agcgatgtgc tcgacctcca    39120
ccctgccgcg tttgccaaga atgacttgag gcgaactggg attgggatag ttgaagaatt    39180
gctggtaatc ctggcgcact gttggggcac tgaagttcga taccaggtcg taggcgtact    39240
gagcggtgtc ggcatcataa ctctcgcgca ggcgaacgta ctcccacaat gaggcgttaa    39300
cgacggcctc ctcttgagtt gcaggcaatc gcgagacaga cacctcgctg tcaacggtgc    39360
cgtccgccg tatccataga tatacgggca caagcctgct caacggcacc attgtggcta    39420
tagcgaacgc ttgagcaaca tttcccaaaa tcgcgatagc tgcgacagct gcaatgagtt    39480
tggagagacg tcgcgccgat ttcgctcgcg cggtttgaaa ggcttctact tccttatagt    39540
gctcggcaag gctttcgcgc gccactagca tggcatattc aggccccgtc atagcgtcca    39600
cccgaattgc cgagctgaag atctgacgga gtaggctgcc atcgcccac attcagcggg    39660
aagatcgggc ctttgcagct cgctaatgtg tcgtttgtct ggcagccgct caaagcgaca    39720
actaggcaca gcaggcaata cttcatagaa ttctccattg aggcgaattt ttgcgcgacc    39780
tagcctcgct caacctgagc gaagcgacgg tacaagctgc tggcagattg ggttgcgccg    39840
ctccagtaac tgcctccaat gttgccggcg atcgccggca aagcgacaat gagcgcatcc    39900
cctgtcagaa aaaacatatc gagttcgtaa agaccaatga tcttggccgc ggtcgtaccg    39960
gcgaaggtga ttacaccaag cataagggtg agcgcagtcg cttcggttag gatgacgatc    40020
gttgccacga ggtttaagag gagaagcaag agaccgtagg tgataagttg cccgatccac    40080
ttagctgcga tgtcccgcgt gcgatcaaaa atatatccga cgaggatcag aggcccgatc    40140
gcgagaagca ctttcgtgag aattccaacg gcgtcgtaaa ctccgaaggc agaccagagc    40200
gtgccgtaaa ggacccactg tgcccctggg aaagcaagga tgtcctggtc gttcatcgga    40260
ccgatttcgg atgcgatttt ctgaaaaacg gcctgggtca cggcgaacat tgtatccaac    40320
tgtgccggaa cagtctgcag aggcaagccg gttacactaa actgctgaac aaagtttggg    40380
accgtctttt cgaagatgga aaccacatag tcttggtagt tagcctgccc aacaattaga    40440
gcaacaacga tggtgaccgt gatcacccga gtgataccgc tacgggtatc gacttcgccg    40500
cgtatgacta aaatacctg aacaataatc caaagagtga cacaggcgat caatggcgca    40560
ctcaccgcct cctggatagt ctcaagcatc gagtccaagc ctgtcgtgaa ggctacatcg    40620
aagatcgtat gaatggccgt aaacggcgcc ggaatcgtga aattcatcga ttggacctga    40680
acttgactgg tttgtcgcat aatgttggat aaaatgagct cgcattcggc gaggatgcgg    40740
gcggatgaac aaatcgccca gccttagggg agggcaccaa agatgacagc ggtcttttga    40800
tgctccttgc gttgagcggc cgcctcttcc gcctcgtgaa ggccggcctg cgcggtagtc    40860
atcgttaata ggcttgtcgc ctgtacattt tgaatcattg cgtcatggat ctgcttgaga    40920
agcaaaccat tggtcacggt tgcctgcatg atattgcgag atcgggaaag ctgagcagac    40980
gtatcagcat tcgccgtcaa gcgtttgtcc atcgtttcca gattgtcagc cgcaatgcca    41040
gcgctgtttg cggaaccggt gatctgcgat cgcaacaggt ccgcttcagc atcactaccc    41100
acgactgcac gatctgtatc gctggtgatc gcacgtgccg tggtcgacat tggcattcgc    41160
ggcgaaaaca tttcattgtc taggtccttc gtcgaaggat actgattttt ctggttgagc    41220
gaagtcagta gtccagtaac gccgtaggcc gacgtcaaca tcgtaaccat cgctatagtc    41280
tgagtgagat tctccgcagt cgcgagcgca gtcgcgagcg tctcagcctc cgttgccggg    41340
```

```
tcgctaacaa caaactgcgc ccgcgcgggc tgaatatata gaaagctgca ggtcaaaact   41400
gttgcaataa gttgcgtcgt cttcatcgtt tcctacctta tcaatcttct gcctcgtggt   41460
gacgggccat gaattcgctg agccagccag atgagttgcc ttcttgtgcc tcgcgtagtc   41520
gagttgcaaa gcgcaccgtg ttggcacgcc ccgaaagcac ggcgacatat tcacgcatat   41580
cccgcagatc aaattcgcag atgacgcttc cactttctcg tttaagaaga aacttacggc   41640
tgccgaccgt catgtcttca cggatcgcct gaaattcctt ttcggtacat ttcagtccat   41700
cgacataagc cgatcgatct gcggttggtg atggatagaa aatcttcgtc atacattgcg   41760
caaccaagct ggctcctagc ggcgattcca gaacatgctc tggttgctgc gttgccagta   41820
ttagcatccc gttgttttt cgaacggtca ggaggaattt gtcgacgaca gtcgaaaatt   41880
tagggtttaa caaataggcg cgaaactcat cgcagctcat cacaaaacgg cggccgtcga   41940
tcatggctcc aatccgatgc aggagatatg ctgcagcggg agcgcatact tcctcgtatt   42000
cgagaagatg cgtcatgtcg aagccggtaa tcgacggatc taactttact tcgtcaactt   42060
cgccgtcaaa tgcccagcca agcgcatggc cccggcacca gcgttggagc gcgctcctg    42120
cgccttcggc gggcccatgc aacaaaaatt cacgtaaccc cgcgattgaa cgcatttgtg   42180
gatcaaacga gagctgacga tggataccac ggaccagacg gcggttctct tccggagaaa   42240
tcccacccg accatcactc tcgatgagag ccacgatcca ttcgcgcaga aaatcgtgtg    42300
aggctgctgt gtttctagg ccacgcaacg gcgccaaccc gctgggtgtg cctctgtgaa    42360
gtgccaaata tgttcctcct gtggcgcgaa ccagcaattc gccacccgg tccttgtcaa    42420
agaacacgac cgtacctgca cggtcgacca tgctctgttc gagcatggct agaacaaaca   42480
tcatgagcgt cgtcttaccc ctcccgatag gcccgaatat tgccgtcatg ccaacatcgt   42540
gctcatgcgg gatatagtcg aaaggcgttc cgccattggt acgaaatcgg gcaatcgcgt   42600
tgccccagtg gcctgagctg gcgccctctg gaaagttttc gaaagagaca aaccctgcga   42660
aattgcgtga agtgattgcg ccaggcgtg tgcgccactt aaaattcccc ggcaattggg    42720
accaataggc cgcttccata ccaataccrt cttggacaac cacggcacct gcatccgcca   42780
ttcgtgtccg agcccgcgcg cccctgtccc caagactatt gagatcgtct gcatagacgc   42840
aaaggctcaa atgatgtgag cccataacga attcgttgct cgcaagtgcg tcctcagcct   42900
cggataattt gccgatttga gtcacggctt tatcgccgga actcagcatc tggctcgatt   42960
tgaggctaag tttcgcgtgc gcttgcgggc gagtcaggaa cgaaaaactc tgcgtgagaa   43020
caagtggaaa atcgagggat agcagcgcgt tgagcatgcc cggccgtgtt tttgcagggt   43080
attcgcgaaa cgaatagatg gatccaacgt aactgtcttt tggcgttctg atctcgagtc   43140
ctcgcttgcc gcaaatgact ctgtcggtat aaatcgaagc gccgagtgag ccgctgacga   43200
ccggaaccgg tgtgaaccga ccagtcatga tcaaccgtag cgcttcgcca atttcggtga   43260
agagcacacc ctgcttctcg cggatgccaa gacgatgcag gccatacgct ttaagagagc   43320
cagcgacaac atgccaaaga tcttccatgt tcctgatctg gcccgtgaga tcgttttccc   43380
ttttttccgct tagcttggtg aacctcctct ttaccttccc taaagccgcc tgtgggtaga   43440
caatcaacgt aaggaagtgt tcattgcgga ggagttggcc ggagagcacg cgctgttcaa   43500
aagcttcgtt caggctagcg gcgaaaacac tacggaagtg tcgcggcgcc gatgatggca   43560
cgtcggcatg acgtacgagg tgagcatata ttgacacatg atcatcagcg atattgcgca   43620
acagcgtgtt gaacgcacga caacgcgcat tgcgcatttc agtttcctca agctcgaatg   43680
```

```
caacgccatc aattctcgca atggtcatga tcgatccgtc ttcaagaagg acgatatggt    43740
cgctgaggtg gccaatataa gggagataga tctcaccgga tctttcggtc gttccactcg    43800
cgccgagcat cacaccattc ctctccctcg tgggggaacc ctaattggat ttgggctaac    43860
agtagcgccc ccccaaactg cactatcaat gcttcttccc gcggtccgca aaaatagcag    43920
gacgacgctc gccgcattgt agtctcgctc cacgatgagc cgggctgcaa accataacgg    43980
cacgagaacg acttcgtaga gcgggttctg aacgataacg atgacaaagc cggcgaacat    44040
catgaataac cctgccaatg tcagtggcac cccaagaaac aatgcgggcc gtgtggctgc    44100
gaggtaaagg gtcgattctt ccaaacgatc agccatcaac taccgccagt gagcgtttgg    44160
ccgaggaagc tcgccccaaa catgataaca atgccgccga cgacgccggc aaccagccca    44220
agcgaagccc gcccgaacat ccaggagatc ccgatagcga caatgccgag aacagcgagt    44280
gactggccga acgaccaag  gataaacgtg catatattgt taaccattgt ggcggggtca    44340
gtgccgccac ccgcagattg cgctgcggcg ggtccggatg aggaaatgct ccatgcaatt    44400
gcaccgcaca agcttggggc gcagctcgat atcacgcgca tcatcgcatt cgagagcgag    44460
aggcgattta gatgtaaacg gtatctctca aagcatcgca tcaatgcgca cctccttagt    44520
ataagtcgaa taagacttga ttgtcgtctg cggatttgcc gttgtcctgg tgtggcggtg    44580
gcggagcgat taaccgcca  gcgccatcct cctgcgagcg gcgctgatat gaccccaaa    44640
catcccacgt ctcttcggat tttagcgcct cgtgatcgtc ttttggaggc tcgattaacg    44700
cgggcaccag cgattgagca gctgtttcaa cttttcgcac gtagccgttt gcaaaaccgc    44760
cgatgaaatt accggtgttg taagcggaga tcgcccgacg aagcgcaaat tgcttctcgt    44820
caatcgtttc gccgcctgca taacgacttt tcagcatgtt tgcagcggca gataatgatg    44880
tgcacgcctg gagcgcaccg tcaggtgtca gaccgagcat agaaaaattt cgagagttta    44940
tttgcatgag gccaacatcc agcgaatgcc gtgcatcgag acggtgcctg acgacttggg    45000
ttgcttggct gtgatcttgc cagtgaagcg tttcgccggt cgtgttgtca tgaatcgcta    45060
aaggatcaaa gcgactctcc accttagcta tcgccgcaag cgtagatgtc gcaactgatg    45120
gggcacactt gcgagcaaca tggtcaaact cagcagatga gagtggcgtg gcaaggctcg    45180
acgaacagaa ggagaccatc aaggcaagag aaagcgaccc cgatctctta agcatacctt    45240
atctccttag ctcgcaacta acaccgcctc tcccgttgga agaagtgcgt tgttttatgt    45300
tgaagattat cgggagggtc ggttactcga aaattttcaa ttgcttcttt atgatttcaa    45360
ttgaagcgag aaacctcgcc cggcgtcttg gaacgcaaca tggaccgaga accgcgcatc    45420
catgactaag caaccggatc gacctattca ggccgcagtt ggtcaggtca ggctcagaac    45480
gaaaatgctc ggcgaggtta cgctgtctgt aaacccattc gatgaacggg aagcttcctt    45540
ccgattgctc ttggcaggaa tattggccca tgcctgcttg cgctttgcaa atgctcttat    45600
cgcgttggta tcatatgcct tgtccgccag cagaaacgca ctctaagcga ttatttgtaa    45660
aaatgtttcg gtcatgcggc ggtcatgggc ttgacccgct gtcagcgcaa gacggatcgg    45720
tcaaccgtcg gcatcgacaa cagcgtgaat cttggtggtc aaaccgccac gggaacgtcc    45780
catacagcca tcgtcttgat cccgctgttt ccgtcgccg  catgttggtg gacgcggaca    45840
caggaactgt caatcatgac gacattctat cgaaagcctt ggaaatcaca ctcagaatat    45900
gatcccagac gtctgcctca cgccatcgta caaagcgatt gtagcaggtt gtacaggaac    45960
cgtatcgatc aggaacgtct gcccagggcg ggcccgtccg gaagcgccac aagatgcat   46020
tgatcacccg cgtcaacgcg cggcacgcga cgcggcttat ttgggaacaa aggactgaac    46080
```

```
aacagtccat tcgaaatcgg tgacatcaaa gcggggacgg gttatcagtg gcctccaagt   46140
caagcctcaa tgaatcaaaa tcagaccgat ttgcaaacct gatttatgag tgtgcggcct   46200
aaatgatgaa atcgtccttc tagatcgcct ccgtggtgta gcaacacctc gcagtatcgc   46260
cgtgctgacc ttggccaggg aattgactgg caagggtgct ttcacatgac cgctcttttg   46320
gccgcgatag atgatttcgt tgctgctttg ggcacgtaga aggagagaag tcatatcgga   46380
gaaattcctc ctggcgcgag agcctgctct atcgcgacgg catcccactg tcgggaacag   46440
accggatcat tcacgaggcg aaagtcgtca acacatgcgt tataggcatc ttcccttgaa   46500
ggatgatctt gttgctgcca atctggaggt gcggcagccg caggcagatg cgatctcagc   46560
gcaacttgcg gcaaaacatc tcactcacct gaaaaccact agcgagtctc gcgatcagac   46620
gaaggccttt tacttaacga cacaatatcc gatgtctgca tcacaggcgt cgctatccca   46680
gtcaatacta aagcggtgca ggaactaaag attactgatg acttaggcgt gccacgaggc   46740
ctgagacgac gcgcgtagac agttttttga aatcattatc aaagtgatgg cctccgctga   46800
agcctatcac ctctgcgccg gtctgtcgga gagatgggca agcattatta cggtcttcgc   46860
gcccgtacat gcattggacg attgcagggt caatggatct gagatcatcc agaggattgc   46920
cgcccttacc ttccgtttcg agttggagcc agcccctaaa tgagacgaca tagtcgactt   46980
gatgtgacaa tgccaagaga gagatttgct taacccgatt tttttgctca agcgtaagcc   47040
tattgaagct tgccggcatg acgtccgcgc cgaaagaata tcctacaagt aaaacattct   47100
gcacaccgaa atgcttggtg tagacatcga ttatgtgacc aagatcctta gcagtttcgc   47160
ttggggaccg ctccgaccag aaataccgaa gtgaactgac gccaatgaca ggaatccctt   47220
ccgtctgcag ataggtacca tcgatagatc tgctgcctcg cgcgtttcgg tgatgacggt   47280
gaaaacctct gacacatgca gctcccggag acggtcacag cttgtctgta agcggatgcc   47340
gggagcagac aagcccgtca gggcgcgtca gcgggtgttg gcgggtgtcg gggcgcagcc   47400
atgacccagt cacgtagcga tagcggagtg tatactggct taactatgcg gcatcagagc   47460
agattgtact gagagtgcac catatgcggt gtgaaatacc gcacagatgc gtaaggagaa   47520
aataccgcat caggcgctct tccgcttcct cgctcactga ctcgctgcgc tcggtcgttc   47580
ggctgcggcg agcggtatca gctcactcaa aggcggtaat acggttatcc acagaatcag   47640
gggataacgc aggaaagaac atgtgagcaa aaggccagca aaaggccagg aaccgtaaaa   47700
aggccgcgtt gctggcgttt ttccataggc tccgcccccc tgacgagcat cacaaaaatc   47760
gacgctcaag tcagaggtgg cgaaacccga caggactata aagataccag gcgtttcccc   47820
ctggaagctc cctcgtgcgc tctcctgttc cgaccctgcc gcttaccgga tacctgtccg   47880
cctttctccc ttcgggaagc gtggcgcttt ctcatagctc acgctgtagg tatctcagtt   47940
cggtgtaggt cgttcgctcc aagctgggct gtgtgcacga acccccgtt cagcccgacc   48000 gctgcgcctt atccggtaac tatcgtcttg agtccaaccc ggtaagacac gacttatcgc   48060
cactggcagc agccactggt aacaggatta gcagagcgag gtatgtaggc ggtgctacag   48120
agttcttgaa gtggtggcct aactacggct acactagaag gacagtattt ggtatctgcg   48180
ctctgctgaa gccagttacc ttcggaaaaa gagttggtag ctcttgatcc ggcaaacaaa   48240
ccaccgctgg tagcggtggt ttttttgttt gcaagcagca gattacgcgc agaaaaaaag   48300
gatctcaaga agatcctttg atcttttcta cggggtctga cgctcagtgg aacgaaaact   48360
cacgttaagg gattttggtc atgagattat caaaaaggat cttcacctag atccttttaa   48420
```

```
attaaaaatg aagttttaaa tcaatctaaa gtatatatga gtaaacttgg tctgacagtt    48480
accaatgctt aatcagtgag gcacctatct cagcgatctg tctatttcgt tcatccatag    48540
ttgcctgact ccccgtcgtg tagataacta cgatacggga gggcttacca tctggcccca    48600
gtgctgcaat gataccgcga gacccacgct caccggctcc agatttatca gcaataaacc    48660
agccagccgg aagggccgag cgcagaagtg gtcctgcaac tttatccgcc tccatccagt    48720
ctattaattg ttgccgggaa gctagagtaa gtagttcgcc agttaatagt ttgcgcaacg    48780
ttgttgccat tgctgcaggg gggggggggg gggggactt ccattgttca ttccacggac     48840
aaaaacagag aaaggaaacg acagaggcca aaaagcctcg ctttcagcac ctgtcgtttc    48900
cttctttc agagggtatt ttaaataaaa acattaagtt atgacgaaga agaacggaaa      48960
cgccttaaac cggaaaattt tcataaatag cgaaaacccg cgaggtcgcc gccccgtaac    49020
ctgtcggatc accggaaagg acccgtaaag tgataatgat tatcatctac atatcacaac   49080
gtgcgtggag gccatcaaac cacgtcaaat aatcaattat gacgcaggta tcgtattaat    49140
tgatctgcat caacttaacg taaaaacaac ttcagacaat acaaatcagc gacactgaat    49200
acggggcaac ctcatgtccc cccccccccc cccctgcag gcatcgtggt gtcacgctcg     49260
tcgtttggta tggcttcatt cagctccggt tcccaacgat caaggcgagt tacatgatcc    49320
cccatgttgt gcaaaaaagc ggttagctcc ttcggtcctc cgatcgttgt cagaagtaag    49380
ttggccgcag tgttatcact catggttatg gcagcactgc ataattctct tactgtcatg    49440
ccatccgtaa gatgctttc tgtgactggt gagtactcaa ccaagtcatt ctgagaatag     49500
tgtatgcggc gaccgagttg ctcttgcccg gcgtcaacac gggataatac cgcgccacat    49560
agcagaactt taaaagtgct catcattgga aaacgttctt cggggcgaaa actctcaagg    49620
atcttaccgc tgttgagatc cagttcgatg taacccactc gtgcacccaa ctgatcttca    49680
gcatctttta ctttcaccag cgtttctggg tgagcaaaaa caggaaggca aaatgccgca    49740
aaaaagggaa taagggcgac acggaaatgt tgaatactca tactcttcct ttttcaatat   49800
tattgaagca tttatcaggg ttattgtctc atgagcggat acatatttga atgtatttag   49860
aaaaataaac aaataggggt tccgcgcaca tttccccgaa aagtgccacc tgacgtctaa    49920
gaaaccatta ttatcatgac attaacctat aaaaataggc gtatcacgag gccctttcgt   49980
cttcaagaat tggtcgacga tcttgctgcg ttcggatatt ttcgtggagt tcccgccaca    50040
gacccggatt gaaggcgaga tccagcaact cgcgccagat catcctgtga cggaactttg    50100
gcgcgtgatg actggccagg acgtcggccg aaagagcgac aagcagatca cgcttttcga    50160
cagcgtcgga tttgcgatcg aggatttttc ggcgctgcgc tacgtccgcg accgcgttga    50220
gggatcaagc cacagcagcc cactcgacct tctagccgac ccagacgagc caagggatct    50280
ttttggaatg ctgctccgtc gtcaggcttt ccgacgtttg ggtggttgaa cagaagtcat    50340
tatcgtacgg aatgccaagc actcccgagg ggaaccctgt ggttggcatg cacatacaaa    50400
tggacgaacg gataaacctt ttcacgcccct tttaaatatc cgttattcta ataaacgctc   50460
ttttctctta ggtttacccg ccaatatatc ctgtcaaaca ctgatagttt aaactgaagg    50520
cgggaaacga caatctgatc atgagcggag aattaaggga gtcacgttat gacccccgcc    50580
gatgacgcgg gacaagccgt tttacgtttg gaactgacag aaccgcaacg ttgaaggagc    50640
cactcagcaa gctggtacga ttgtaatacg actcactata gggcgaattg agcgctgttt    50700
aaacgctctt caactggaag agcggttact accggttaag tgactagggt c             50751
```

```
<210> SEQ ID NO 8
<211> LENGTH: 20
<212> TYPE: DNA
<213> ORGANISM: Artificial Sequence
<220> FEATURE:
<223> OTHER INFORMATION: Forward primer for GUS expression

<400> SEQUENCE: 8
cggaagcaac gcgtaaactc                                           20

<210> SEQ ID NO 9
<211> LENGTH: 21
<212> TYPE: DNA
<213> ORGANISM: Artificial Sequence
<220> FEATURE:
<223> OTHER INFORMATION: reverse primer for GUS expression

<400> SEQUENCE: 9
tgtgagcgtc gcagaacatt a                                         21

<210> SEQ ID NO 10
<211> LENGTH: 20
<212> TYPE: DNA
<213> ORGANISM: Artificial Sequence
<220> FEATURE:
<223> OTHER INFORMATION: Probe sequence for GUS expression

<400> SEQUENCE: 10
cgcgtccgat cacctgcgtc                                           20

<210> SEQ ID NO 11
<211> LENGTH: 23
<212> TYPE: DNA
<213> ORGANISM: Artificial Sequence
<220> FEATURE:
<223> OTHER INFORMATION: TERM F primer

<400> SEQUENCE: 11
ctgtcagttc caaacgtaaa acg                                       23

<210> SEQ ID NO 12
<211> LENGTH: 25
<212> TYPE: DNA
<213> ORGANISM: Artificial Sequence
<220> FEATURE:
<223> OTHER INFORMATION: TERM R primer

<400> SEQUENCE: 12
aatctgatca tgagcggaga attaa                                     25

<210> SEQ ID NO 13
<211> LENGTH: 20
<212> TYPE: DNA
<213> ORGANISM: Artificial Sequence
<220> FEATURE:
<223> OTHER INFORMATION: TERM F primer

<400> SEQUENCE: 13
tcccgggtcc ttaggaagac                                           20

<210> SEQ ID NO 14
<211> LENGTH: 21
<212> TYPE: DNA
<213> ORGANISM: Artificial Sequence
<220> FEATURE:
<223> OTHER INFORMATION: TERM R primer
```

```
<400> SEQUENCE: 14
tggattcagc aggcctagaa g                                              21

<210> SEQ ID NO 15
<211> LENGTH: 18
<212> TYPE: DNA
<213> ORGANISM: Artificial Sequence
<220> FEATURE:
<223> OTHER INFORMATION: TERM P-probe

<400> SEQUENCE: 15
tcctcaggat ttaaatgg                                                  18

<210> SEQ ID NO 16
<211> LENGTH: 20
<212> TYPE: DNA
<213> ORGANISM: Artificial Sequence
<220> FEATURE:
<223> OTHER INFORMATION: ActinFwd primer

<400> SEQUENCE: 16
cttcgaatgc ccagcaatgt                                                20

<210> SEQ ID NO 17
<211> LENGTH: 21
<212> TYPE: DNA
<213> ORGANISM: Artificial Sequence
<220> FEATURE:
<223> OTHER INFORMATION: Actin rev primer

<400> SEQUENCE: 17
gttcgcccac tagcgtacaa c                                              21

<210> SEQ ID NO 18
<211> LENGTH: 15
<212> TYPE: DNA
<213> ORGANISM: Artificial Sequence
<220> FEATURE:
<223> OTHER INFORMATION: Actin probe

<400> SEQUENCE: 18
tcgaggctgt tcttt                                                     15

<210> SEQ ID NO 19
<211> LENGTH: 406
<212> TYPE: DNA
<213> ORGANISM: Sorghum bicolor

<400> SEQUENCE: 19
gtttttctca gacagttttc taaaaaaagg gcgtttctgg ggaagttcga gatggttcgt     60
aaggtgttac tggctcctgt gaaccaatac atgatactgc catgataagg gttataatta    120
gtcaagcaga gtaagaagaa ataacagtag cagtgactcc gattcctgaa gatgagtcat    180
atttgtcttg tgctcctgct gtatgaaatg gatcgcatgt gtatattcgt cgccgcgccg    240
cactggtgta acctgttgcc tcagagtttg cttttagctg gttctgtttt aaaaataagt    300
actgtttttt ggttggctgc aagccattct gaacttcagt ttaccaattg ttttatgtt     360 gtggttgaat attttaattt tttatttaat gtttggttct tttttt                   406

<210> SEQ ID NO 20
<211> LENGTH: 1835
<212> TYPE: DNA
<213> ORGANISM: sorghum bicolor
```

```
<400> SEQUENCE: 20
cgggaccagt cccgcgcggc ccgtcaggcc gtcgtcacgc tcgcagcacc ggccggtttc      60
tacgggcggt gcagtggacg cactagtctc ttcgaagacg gcggcggcgt gtggtataaa     120
cccgggggccg cccgtcacgc cgccccgtcc gtgcgtttcc ttttgtttct tgctttgctt    180
cttttcgagt gcttgccgtc cgtcactgct cgccgatcga gttttctccg gattccagca    240
gagaggcccc gaacgaagcg atcatcgccg cacctctctt cgagcagaat agttgagaat    300
ggctgacgag gatattcagc ctatcgtatg cgacaatggc actggaatgg tcaaggccgg    360
ttttgctggt gatgatgcac caagagctgt cttccccagc attgtgggaa gaccgcgcca    420
taccggtgtc atggttggca tgggccaaaa ggatgcctat gtaggtgatg aggctcaggc    480
caagagaggc atcctgacac tgaagtaccc aattgagcat ggcattgtca acaactggga    540
tgacatggag aaaatctggc atcacacctt ctacaacgag ctccgtgttg cgcctgaaga    600
tcaccctgta ctgctgaccg aggctcctct caacccccaag gccaacagag agaaaatgac   660
acagattatg tttgaaacct ttgaatgccc agcaatgtat gttgctatcc aggctgttct    720
ttccttgtat gctagtgggc gaacaactgg tattgtgatg gactccggtg atggtgtgag    780
ccacacagtt ccaatatacg aaggatacac acttcctcat gctattctcc gtttggatct    840
tgcgggcgt gacctcaccg accacctaat gaagatcctc acagagagag ggtactccct     900
cactacgagc gctgagcgag aaattgtcag ggacataaag gagaagctcg cctatgttgc    960
ccttgattat gaacaggagc tggaaacagc caggagcagc tcctctgttg agaagagcta   1020
cgagatgcct gatggtcagg tcatcaccat tgggtcagaa aggttcaggt gccccgaggt   1080
gctgttccag ccatctcttg ttggtatgga atcgcctggc gtacatgaag ccacatacaa   1140
ctccatcatg aagtgtgatg ttgatatcag gaaggatttg tatggtaatg ttgtcctcag   1200
tggaggatct accatgttcc ctgggattgc tgatcgaatg agcaaggaga tcacgtccct   1260
ggctcctagc agcatgaaga ttaaagtgat tgcaccacct gaaaggaaat acagtgtctg   1320
gattggtggc tctatttgg cttctctcag cacttttcag cagatgtgga tctcgaaggc   1380
agagtatgat gaaaccggtc caggcattgt ccacatgaag tgcttctaag ttttctcag    1440
acagttttct aaaaaaaggg cgtttctggg gaagttcgag atggttcgta aggtgttact   1500
ggctcctgtg aaccaataca tgatactgcc atgataaggg ttataattag tcaagcagag   1560
taagaagaaa taacagtagc agtgactccg attcctgaag atgagtcata tttgtcttgt   1620
gctcctgctg tatgaaatgg atcgcatgtg tatattcgtc gccgcgccgc actggtgtaa   1680
cctgttgcct cagagtttgc ttttagctgg ttctgttta aaaataagta ctgtttttg    1740
gttggctgca agccattctg aacttcagtt taccaattgt ttttatgttg tggttgaata   1800
ttttaatttt ttatttaatg tttggttctt ttttt                              1835
```